US012605473B2

(12) United States Patent
Kelly et al.

(10) Patent No.: US 12,605,473 B2
(45) **Date of Patent: *Apr. 21, 2026**

(54) METHODS FOR MAKING RADIOLABELED ANTI-MET BINDING PROTEINS

(71) Applicant: Regeneron Pharmaceuticals, Inc., Tarrytown, NY (US)

(72) Inventors: Marcus Kelly, New York, NY (US); Dangshe Ma, Millwood, NY (US); William Olson, Yorktown Heights, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/400,943

(22) Filed: Dec. 29, 2023

(65) Prior Publication Data

US 2024/0307563 A1 Sep. 19, 2024

Related U.S. Application Data

(63) Continuation of application No. 17/021,497, filed on Sep. 15, 2020, now Pat. No. 11,896,682.

(60) Provisional application No. 62/901,003, filed on Sep. 16, 2019.

(51) Int. Cl.
*A61K 51/10* (2006.01)
*C07K 16/28* (2006.01)

(52) U.S. Cl.
CPC ........ *A61K 51/103* (2013.01); *C07K 16/2863* (2013.01); *C07K 2317/21* (2013.01); *C07K 2317/31* (2013.01); *C07K 2317/565* (2013.01); *C07K 2317/77* (2013.01); *C07K 2317/92* (2013.01); *C07K 2317/94* (2013.01)

(58) Field of Classification Search
CPC .............. A61K 51/103; A61K 51/1093; C07K 16/2863; C07K 2317/21; C07K 2317/31; C07K 2317/565; C07K 2317/77; C07K 2317/92; C07K 2317/94; G01N 2333/71; G01N 33/534; A61P 35/00
See application file for complete search history.

(56) References Cited

U.S. PATENT DOCUMENTS

| | | | |
|---|---|---|---|
| 4,680,338 | A | 7/1987 | Sundoro |
| 5,208,020 | A | 5/1993 | Chari et al. |
| 5,332,567 | A | 7/1994 | Goldenberg |
| 5,639,879 | A | 6/1997 | Mease et al. |
| 5,646,036 | A | 7/1997 | Schwall et al. |
| 5,686,292 | A | 11/1997 | Schwall et al. |
| 5,707,624 | A | 1/1998 | Nickoloff et al. |
| 5,714,586 | A | 2/1998 | Kunstmann et al. |
| 6,099,841 | A | 8/2000 | Hillan et al. |
| 6,207,152 | B1 | 3/2001 | Schwall et al. |
| 6,214,344 | B1 | 4/2001 | Schwall et al. |
| 6,468,529 | B1 | 10/2002 | Schwall et al. |
| 7,087,411 | B2 | 8/2006 | Daly et al. |
| 7,476,724 | B2 | 1/2009 | Dennis et al. |
| 7,498,420 | B2 | 3/2009 | Michaud et al. |
| 7,556,804 | B2 | 7/2009 | Prat |
| 7,615,529 | B2 | 11/2009 | Kong-Beltran et al. |
| 7,714,016 | B2 | 5/2010 | Gangwar et al. |
| 7,718,174 | B2 | 5/2010 | Chung et al. |
| 7,750,116 | B1 | 7/2010 | Doronina et al. |
| 7,754,681 | B2 | 7/2010 | Feng |
| 7,892,550 | B2 | 2/2011 | Dennis et al. |
| 7,892,770 | B2 | 2/2011 | Cao et al. |
| 8,039,598 | B2 | 10/2011 | Cao |
| 8,101,727 | B2 | 1/2012 | Stover et al. |
| 8,133,867 | B2 | 3/2012 | Otsuka et al. |
| 8,163,280 | B2 | 4/2012 | Michaud et al. |
| 8,217,148 | B2 | 7/2012 | Davies et al. |
| 8,309,315 | B2 | 11/2012 | Cao et al. |
| 8,329,173 | B2 | 12/2012 | Goetsch |
| 8,388,958 | B2 | 3/2013 | Comoglio et al. |
| 8,398,974 | B2 | 3/2013 | Davies et al. |
| 8,455,623 | B2 | 6/2013 | Van Der Horst et al. |
| 8,501,917 | B2 | 8/2013 | Kim et al. |
| 8,536,118 | B2 | 9/2013 | Kong-Beltran et al. |
| 8,545,839 | B2 | 10/2013 | Goetsch et al. |
| 8,546,544 | B2 | 10/2013 | Cheong et al. |
| 8,562,985 | B2 | 10/2013 | Michaud et al. |
| 8,563,696 | B2 | 10/2013 | Cheong et al. |
| 8,623,359 | B2 | 1/2014 | Goetsch |
| 8,637,027 | B2 | 1/2014 | Hultberg et al. |

(Continued)

FOREIGN PATENT DOCUMENTS

| | | | |
|---|---|---|---|
| EP | 1636593 | B9 | 12/2009 |
| EP | 2127683 | A1 | 12/2009 |

(Continued)

OTHER PUBLICATIONS

Paul, WE (1993) Fundamental Immunology, 3rd ed. Raven Press, NY, Chap. 9, pp. 292-295.*
Rudikoff, S et al. (1982) Proc. Natl. Acad. Sci. USA, 79:1979-1983 (doi: 10.1073/pnas.79.6.1979).*
Colman, PM (1994) Research in Immunology, Elsevier, NY, 145(1):33-36.*
Bendig M. M. (1995) Methods: A Companion to Methods in Enzymology, 8:83-93.*
MacCallum et al. (Oct. 11, 1996) J. Mol. Biol., 262(5):732-745. (doi: 10.1006/jmbi.1996.0548).*

(Continued)

*Primary Examiner* — Robert S Landsman
(74) *Attorney, Agent, or Firm* — FisherBroyles, LLP; Cara L. Crowley-Weber; Casey Donahoe

(57) ABSTRACT

Radiolabeled anti-MET antibodies and MET×MET bispecific antibodies and their use in immuno-PET imaging are provided herein. Included are methods of detecting the presence of MET proteins in a subject or sample and methods of monitoring efficacy of treatment of a Met expressing tumor.

28 Claims, 12 Drawing Sheets

Specification includes a Sequence Listing.

(56) References Cited

U.S. PATENT DOCUMENTS

| | | | |
|---|---|---|---|
| 8,673,302 | B2 | 3/2014 | Goetsch et al. |
| 8,741,290 | B2 | 6/2014 | Goetsch et al. |
| 8,747,850 | B2 | 6/2014 | Goetsch et al. |
| 8,765,128 | B2 | 7/2014 | Goetsch et al. |
| 8,771,966 | B2 | 7/2014 | Dennis et al. |
| 8,821,869 | B2 | 9/2014 | Michaud et al. |
| 8,871,909 | B2 | 10/2014 | Goetsch |
| 8,871,910 | B2 | 10/2014 | Goetsch |
| 8,889,832 | B2 | 11/2014 | Goetsch |
| 8,900,582 | B2 | 12/2014 | Cheong et al. |
| 9,011,865 | B2 | 4/2015 | Goetsch |
| 9,062,104 | B2 | 6/2015 | Garcia-Martinez et al. |
| 9,068,011 | B2 | 6/2015 | Neijssen et al. |
| 9,101,610 | B2 | 8/2015 | Cheong et al. |
| 9,107,907 | B2 | 8/2015 | Goetsch |
| 9,120,852 | B2 | 9/2015 | Jouhanneaud |
| 9,150,655 | B2 | 10/2015 | Wu et al. |
| 9,169,329 | B2 | 10/2015 | Johns et al. |
| 9,192,666 | B2 | 11/2015 | Kim et al. |
| 9,201,074 | B2 | 12/2015 | Davies et al. |
| 9,213,031 | B2 | 12/2015 | Lee et al. |
| 9,233,155 | B2 | 1/2016 | Kim et al. |
| 9,249,221 | B2 | 2/2016 | Lee et al. |
| 9,260,531 | B2 | 2/2016 | Beuerlein et al. |
| 9,296,817 | B2 | 3/2016 | Kim et al. |
| 9,328,173 | B2 | 5/2016 | Aldaz et al. |
| 9,359,437 | B2 | 6/2016 | Davis et al. |
| 9,364,556 | B2 | 6/2016 | Park et al. |
| 9,375,425 | B2 | 6/2016 | Goetsch |
| 9,394,367 | B2 | 7/2016 | Cheong et al. |
| 9,429,584 | B2 | 8/2016 | Matsumura et al. |
| 9,458,245 | B2 | 10/2016 | Harms et al. |
| 9,469,691 | B2 | 10/2016 | Cheong et al. |
| 9,475,874 | B2 | 10/2016 | Sawada et al. |
| 9,481,725 | B2 | 11/2016 | Dutzar et al. |
| 9,487,589 | B2 | 11/2016 | Demeule et al. |
| 9,505,843 | B2 | 11/2016 | Kim et al. |
| 9,535,055 | B2 | 1/2017 | Kim et al. |
| 9,546,206 | B2 | 1/2017 | Ring et al. |
| 9,556,275 | B2 | 1/2017 | Jeong et al. |
| 9,567,641 | B2 | 2/2017 | Kim et al. |
| 9,572,878 | B2 | 2/2017 | Lee et al. |
| 9,580,508 | B2 | 2/2017 | Chiu et al. |
| 9,593,164 | B2 | 3/2017 | Chiu et al. |
| 9,631,020 | B2 | 4/2017 | Park et al. |
| 9,631,027 | B2 | 4/2017 | Hultberg et al. |
| 9,637,541 | B2 | 5/2017 | Kim et al. |
| 9,650,443 | B2 | 5/2017 | Song et al. |
| 9,657,104 | B2 | 5/2017 | Cho et al. |
| 9,657,107 | B2 | 5/2017 | Neijssen et al. |
| 9,688,773 | B2 | 6/2017 | Hultberg et al. |
| 9,695,228 | B2 | 7/2017 | Mark et al. |
| 9,717,715 | B2 | 8/2017 | Lee et al. |
| 9,725,497 | B2 | 8/2017 | Anderson et al. |
| 9,730,926 | B2 | 8/2017 | Lin et al. |
| 9,732,150 | B2 | 8/2017 | Garcia-Martinez et al. |
| 9,783,603 | B2 | 10/2017 | Garcia-Martinez et al. |
| 9,808,507 | B2 | 11/2017 | Oh et al. |
| 9,884,917 | B2 | 2/2018 | Hultberg et al. |
| 9,902,776 | B2 | 2/2018 | Cho et al. |
| 9,931,400 | B2 | 4/2018 | Jeong et al. |
| 9,950,076 | B2 | 4/2018 | Nittoli et al. |
| 9,975,960 | B2 | 5/2018 | Cho et al. |
| 9,994,644 | B2 | 6/2018 | Wong et al. |
| 10,000,569 | B2 | 6/2018 | Cheong et al. |
| 10,100,108 | B2 | 10/2018 | Dutzar et al. |
| 10,106,622 | B2 | 10/2018 | Yoo et al. |
| 10,143,749 | B2 | 12/2018 | Cho et al. |
| 10,214,593 | B2 | 2/2019 | Jung et al. |
| 10,246,507 | B2 | 4/2019 | Lee et al. |
| 10,570,151 | B2 | 2/2020 | Nittoli et al. |
| 10,730,944 | B2 | 8/2020 | Giurleo et al. |
| 10,736,976 | B2 | 8/2020 | Kelly et al. |
| 10,738,130 | B2 | 8/2020 | Haber et al. |
| 10,905,784 | B2 | 2/2021 | Kelly et al. |
| 11,142,578 | B2 | 10/2021 | Babb et al. |
| 11,511,001 | B2 | 11/2022 | Kelly et al. |
| 11,525,001 | B2 | 12/2022 | Giurleo et al. |
| 11,896,682 | B2 | 2/2024 | Kelly et al. |
| 12,053,534 | B2 | 8/2024 | Kelly et al. |
| 12,077,587 | B2 | 9/2024 | Giurleo et al. |
| 2004/0018557 | A1 | 1/2004 | Qu et al. |
| 2004/0166544 | A1 | 8/2004 | Morton et al. |
| 2005/0233960 | A1 | 10/2005 | Kong-Beltran et al. |
| 2007/0258987 | A1 | 11/2007 | Francisco et al. |
| 2007/0280945 | A1 | 12/2007 | Stevens et al. |
| 2008/0193376 | A1 | 8/2008 | Tawakol et al. |
| 2008/0260650 | A1 | 10/2008 | Tawakol et al. |
| 2008/0305497 | A1 | 12/2008 | Kosmeder et al. |
| 2009/0068179 | A1 | 3/2009 | Nayeri et al. |
| 2009/0142354 | A1 | 6/2009 | Papadopoulos et al. |
| 2009/0226443 | A1 | 9/2009 | Filvaroff et al. |
| 2009/0226455 | A1 | 9/2009 | Filvaroff |
| 2009/0297439 | A1 | 12/2009 | Comoglio et al. |
| 2010/0016241 | A1 | 1/2010 | Kong-Beltran et al. |
| 2010/0111856 | A1 | 5/2010 | Gill et al. |
| 2010/0129314 | A1 | 5/2010 | Singh et al. |
| 2010/0254988 | A1 | 10/2010 | Bossenmaier et al. |
| 2010/0256339 | A1 | 10/2010 | Bossenmaier et al. |
| 2011/0027286 | A1 | 2/2011 | Thurston et al. |
| 2011/0104161 | A1 | 5/2011 | Burgess et al. |
| 2011/0104166 | A1 | 5/2011 | Stankovic et al. |
| 2011/0229469 | A1 | 9/2011 | Johns |
| 2011/0239316 | A1 | 9/2011 | Goetsch et al. |
| 2011/0287003 | A1 | 11/2011 | Patel et al. |
| 2012/0134996 | A1 | 5/2012 | Comoglio et al. |
| 2012/0171210 | A1 | 7/2012 | Kong-Beltran et al. |
| 2012/0237524 | A1 | 9/2012 | Boccaccio et al. |
| 2013/0089542 | A1 | 4/2013 | Lee et al. |
| 2013/0101546 | A1 | 4/2013 | Yurkovetskiy et al. |
| 2013/0102494 | A1 | 4/2013 | Jouhanneaud |
| 2013/0109840 | A1 | 5/2013 | Goetsch et al. |
| 2013/0129718 | A1 | 5/2013 | Wong et al. |
| 2013/0143813 | A1 | 6/2013 | Kirchhofer et al. |
| 2013/0156772 | A1 | 6/2013 | Bossenmaier et al. |
| 2013/0164281 | A1 | 6/2013 | Cheong et al. |
| 2013/0171063 | A1 | 7/2013 | Johns et al. |
| 2013/0209365 | A1 | 8/2013 | Wu et al. |
| 2013/0216548 | A1 | 8/2013 | Neijssen et al. |
| 2013/0315895 | A1 | 11/2013 | Farrell et al. |
| 2013/0316450 | A1 | 11/2013 | Van Der Horst et al. |
| 2014/0349310 | A1 | 11/2014 | Davies et al. |
| 2014/0377174 | A1 | 12/2014 | Houthoff et al. |
| 2015/0017170 | A1 | 1/2015 | Oh et al. |
| 2015/0050275 | A1 | 2/2015 | Wong et al. |
| 2015/0182622 | A1 | 7/2015 | Lashkari |
| 2015/0191543 | A1 | 7/2015 | Wu et al. |
| 2015/0197542 | A1 | 7/2015 | Kim et al. |
| 2015/0284808 | A1 | 10/2015 | Chung et al. |
| 2015/0299133 | A1 | 10/2015 | Osterkamp et al. |
| 2015/0299326 | A1 | 10/2015 | Wu et al. |
| 2016/0000946 | A1 | 1/2016 | Cheng et al. |
| 2016/0151515 | A1 | 6/2016 | Joubert et al. |
| 2016/0222115 | A1 | 8/2016 | Huang et al. |
| 2016/0354482 | A1 | 12/2016 | Nittoli |
| 2016/0375147 | A1 | 12/2016 | Nittoli |
| 2017/0029507 | A1 | 2/2017 | Ho et al. |
| 2017/0119913 | A1 | 5/2017 | Osterkamp et al. |
| 2017/0137539 | A1 | 5/2017 | Fu et al. |
| 2017/0209591 | A1 | 7/2017 | Nittoli et al. |
| 2017/0233489 | A1 | 8/2017 | Shim et al. |
| 2017/0258948 | A1 | 9/2017 | Morin et al. |
| 2017/0281796 | A1 | 10/2017 | Zhu et al. |
| 2017/0283442 | A1 | 10/2017 | D'Souza et al. |
| 2017/0283501 | A1 | 10/2017 | Swanson et al. |
| 2017/0348429 | A1 | 12/2017 | Reilly et al. |
| 2018/0015154 | A1 | 1/2018 | Weichert et al. |
| 2018/0043041 | A1 | 2/2018 | Bansal et al. |
| 2018/0055947 | A1 | 3/2018 | Van Dongen et al. |
| 2018/0078662 | A1 | 3/2018 | Agnew et al. |
| 2018/0110875 | A1 | 4/2018 | Liu et al. |
| 2018/0126012 | A1 | 5/2018 | Weichert et al. |
| 2018/0134794 | A1 | 5/2018 | Babb et al. |
| 2018/0250418 | A1 | 9/2018 | Afar et al. |

(56) References Cited

U.S. PATENT DOCUMENTS

| | | | |
|---|---|---|---|
| 2018/0280531 A1 | 10/2018 | Zhu et al. | |
| 2018/0326085 A1 | 11/2018 | Doerner et al. | |
| 2018/0327500 A1 | 11/2018 | Bouquin et al. | |
| 2022/0040319 A1 | 2/2022 | Schwartz et al. | |
| 2022/0049001 A1 | 2/2022 | Babb et al. | |
| 2023/0270894 A1 | 8/2023 | Kelly et al. | |
| 2024/0299601 A1 | 9/2024 | Cheung et al. | |
| 2024/0335572 A1 | 10/2024 | Kelly et al. | |
| 2024/0409637 A1 | 12/2024 | Giurleo et al. | |
| 2025/0250342 A2 | 8/2025 | Babb et al. | |

FOREIGN PATENT DOCUMENTS

| | | | |
|---|---|---|---|
| EP | 0922102 | B1 | 4/2010 |
| EP | 1641828 | B1 | 4/2010 |
| EP | 1773885 | B1 | 4/2010 |
| EP | 2188312 | | 5/2010 |
| EP | 2316484 | | 5/2011 |
| EP | 1981981 | B1 | 6/2011 |
| EP | 2336178 | A1 | 6/2011 |
| EP | 2575879 | B1 | 6/2011 |
| EP | 1997511 | B1 | 7/2011 |
| EP | 2367008 | A2 | 9/2011 |
| EP | 1957102 | B1 | 1/2012 |
| EP | 2195345 | B1 | 5/2012 |
| EP | 2004693 | B1 | 6/2012 |
| EP | 2500036 | A1 | 9/2012 |
| EP | 2535356 | | 12/2012 |
| EP | 2787008 | A1 | 10/2014 |
| EP | 1868648 | B1 | 4/2015 |
| EP | 2358755 | | 9/2015 |
| EP | 2963058 | A1 | 1/2016 |
| EP | 2635603 | B1 | 3/2016 |
| EP | 2611928 | B1 | 4/2016 |
| EP | 3266465 | A1 | 7/2016 |
| EP | 2635602 | B1 | 9/2016 |
| EP | 2370468 | B1 | 4/2017 |
| EP | 2824113 | B1 | 5/2017 |
| EP | 2588497 | | 6/2017 |
| EP | 2870178 | B1 | 7/2017 |
| EP | 3196211 | A1 | 7/2017 |
| EP | 2786764 | B1 | 8/2017 |
| EP | 2832748 | B1 | 9/2017 |
| EP | 2784091 | B1 | 11/2017 |
| EP | 2784092 | B1 | 12/2017 |
| EP | 2467402 | B1 | 1/2018 |
| EP | 2963058 | B1 | 2/2018 |
| EP | 3284751 | A1 | 2/2018 |
| EP | 2786765 | B1 | 3/2018 |
| EP | 2415785 | | 4/2018 |
| EP | 2535357 | | 8/2018 |
| EP | 2764026 | B1 | 8/2018 |
| EP | 3135691 | B1 | 8/2018 |
| EP | 2545077 | B1 | 10/2018 |
| EP | 2922566 | B1 | 10/2018 |
| EP | 2922872 | B1 | 10/2018 |
| EP | 2937421 | B1 | 10/2018 |
| EP | 2708556 | B1 | 11/2018 |
| EP | 2992019 | B1 | 3/2019 |
| EP | 2764024 | A1 | 8/2019 |
| EP | 3544634 | B1 | 4/2021 |
| JP | 2009-292815 | | 12/2009 |
| WO | WO 2005/016382 | A1 | 2/2005 |
| WO | WO 2005/058965 | A1 | 6/2005 |
| WO | WO 2005/089808 | | 9/2005 |
| WO | WO 2006/015371 | A2 | 2/2006 |
| WO | WO 2007/064345 | A2 | 6/2007 |
| WO | WO 2008/122039 | | 10/2008 |
| WO | WO 2008/124467 | A1 | 10/2008 |
| WO | WO 2009/111691 | A2 | 9/2009 |
| WO | WO 2009/140549 | A1 | 11/2009 |
| WO | WO 2010/010324 | | 1/2010 |
| WO | WO 2010/045344 | | 4/2010 |
| WO | WO 2010/045345 | | 4/2010 |
| WO | WO 2010/115551 | | 10/2010 |
| WO | WO 2010/115552 | | 10/2010 |
| WO | WO 2010/115553 | | 10/2010 |
| WO | WO 2011/018611 | | 2/2011 |
| WO | WO 2011/056983 | | 5/2011 |
| WO | WO 2011/110642 | A2 | 9/2011 |
| WO | WO 2011/130598 | | 10/2011 |
| WO | WO 2011/143665 | | 11/2011 |
| WO | WO 2011/150454 | A1 | 12/2011 |
| WO | WO 2011/153346 | A1 | 12/2011 |
| WO | WO 2012/003338 | | 1/2012 |
| WO | WO 2012/005982 | A2 | 1/2012 |
| WO | WO 2012/087962 | A2 | 6/2012 |
| WO | WO 2012/136685 | | 10/2012 |
| WO | WO 2012/161372 | | 11/2012 |
| WO | WO 2012/165925 | | 12/2012 |
| WO | WO 2012/166559 | | 12/2012 |
| WO | WO 2013/003680 | A1 | 1/2013 |
| WO | WO 2013/043452 | | 3/2013 |
| WO | WO 2013/043715 | | 3/2013 |
| WO | WO 2013/045707 | A2 | 4/2013 |
| WO | WO 2013/051891 | | 4/2013 |
| WO | WO 2013/053872 | | 4/2013 |
| WO | WO 2013/053873 | | 4/2013 |
| WO | WO 2013/055990 | | 4/2013 |
| WO | WO 2013/055993 | | 4/2013 |
| WO | WO 2013/064701 | A2 | 5/2013 |
| WO | WO 2013/068874 | | 5/2013 |
| WO | WO 2013/081379 | | 6/2013 |
| WO | WO 2013/085925 | | 6/2013 |
| WO | WO 2013/138696 | A1 | 9/2013 |
| WO | WO 2013/149159 | A1 | 10/2013 |
| WO | WO 2013/152252 | A1 | 10/2013 |
| WO | WO 2013/165940 | A1 | 11/2013 |
| WO | WO 2013/169532 | A1 | 11/2013 |
| WO | WO 2013/177055 | A2 | 11/2013 |
| WO | WO 2013/188752 | | 12/2013 |
| WO | WO 2013/192594 | | 12/2013 |
| WO | WO 2014/065661 | A1 | 5/2014 |
| WO | WO 2014/081944 | | 5/2014 |
| WO | WO 2014/081954 | | 5/2014 |
| WO | WO 2014/145090 | A1 | 9/2014 |
| WO | WO 2014/159087 | A1 | 10/2014 |
| WO | WO 2014/159835 | A1 | 10/2014 |
| WO | WO 2014/200969 | A2 | 12/2014 |
| WO | WO 2014/210064 | A1 | 12/2014 |
| WO | WO 2015/031396 | A1 | 3/2015 |
| WO | WO 2015/053871 | A2 | 4/2015 |
| WO | WO 2015/061209 | A1 | 4/2015 |
| WO | WO 2015/075445 | A1 | 5/2015 |
| WO | WO 2015/081857 | A1 | 6/2015 |
| WO | WO 2015/089344 | A1 | 6/2015 |
| WO | WO 2015/132602 | A1 | 9/2015 |
| WO | WO 2015/140212 | A1 | 9/2015 |
| WO | WO 2015/179658 | A2 | 11/2015 |
| WO | WO 2015/191715 | A1 | 12/2015 |
| WO | WO 2016/020502 | A1 | 2/2016 |
| WO | WO 2016/040723 | A1 | 3/2016 |
| WO | WO 2016/040724 | A1 | 3/2016 |
| WO | WO 2016/040868 | A1 | 3/2016 |
| WO | WO 2016/042412 | A1 | 3/2016 |
| WO | WO 2016/058056 | A1 | 4/2016 |
| WO | WO 2016/060297 | | 4/2016 |
| WO | WO 2016/094455 | A1 | 6/2016 |
| WO | WO 2016/144873 | A2 | 9/2016 |
| WO | WO 2016149265 | A1 | 9/2016 |
| WO | WO 2016/160615 | A1 | 10/2016 |
| WO | WO 2017/059397 | A1 | 4/2017 |
| WO | WO 2017/076492 | A1 | 5/2017 |
| WO | WO 2017/087603 | A1 | 5/2017 |
| WO | WO 2017/087826 | A1 | 5/2017 |
| WO | WO 2017/132173 | A1 | 8/2017 |
| WO | WO 2017/135791 | A1 | 8/2017 |
| WO | WO 2017/201111 | A1 | 11/2017 |
| WO | WO 2017/201204 | A1 | 11/2017 |
| WO | WO 2017/213494 | A1 | 12/2017 |
| WO | WO 2017/223565 | A1 | 12/2017 |
| WO | WO 2018/049083 | A1 | 3/2018 |
| WO | WO 2018/050733 | A1 | 3/2018 |
| WO | WO 2018/058125 | A1 | 3/2018 |

(56) References Cited

FOREIGN PATENT DOCUMENTS

| | | | |
|---|---|---|---|
| WO | WO 2018/068758 | | 4/2018 |
| WO | WO 2018/069851 | | 4/2018 |
| WO | WO 2018/083705 | A1 | 5/2018 |
| WO | WO 2018/093866 | A1 | 5/2018 |
| WO | WO 2018/098035 | A1 | 5/2018 |
| WO | WO 2018/128664 | A2 | 7/2018 |
| WO | WO 2018/221969 | A1 | 12/2018 |
| WO | WO 2018/223958 | A1 | 12/2018 |
| WO | WO 2018/232349 | A1 | 12/2018 |
| WO | WO 2019/031965 | A1 | 2/2019 |
| WO | WO 2019/066617 | | 4/2019 |
| WO | WO 2019/066620 | | 4/2019 |
| WO | WO 2020/172475 | A1 | 8/2020 |
| WO | WO 2022/171115 | A1 | 8/2022 |

OTHER PUBLICATIONS

Casset et al (2003) Biochemical and Biophysical Research Communications, 307:198-205. (doi:10.1016/S0006-291X(03)01131-8).*

Chen et al. (1995) EMBO J., 14(12):2784-2794. (doi: 10.1002/j.1460-2075.1995.tb07278.x).*

Chattopadhyay et al. (2011) "Targeting c-Met/HGF Pathway in Uveal Melanoma Cells", Investigative Ophthalmology & Visual Science, Apr. 2011, 52:1443, ARVO Annual Meeting Abstract, <URL; https://iovs.arvojournals.org/article.aspx?articleid=2352151> 4 pages.

Moek et al. (2017) "The Antibody-Drug Conjugate Target Landscape Across a Broad Range of Tumour Types," Annals of Oncology, 28(12): 3083-3091.

Iyer et al. (2011) "Antibody Drug Conjugates—Trojan Horses in the War on Cancer," Journal of Pharmacological and Toxicological Methods, 64(3): 207-212.

Sugyo et al. (2013) "Evaluation of 89Zr-Labeled Human Anti-CD147 Monoclonal Antibody as a Positron Emission Tomography Probe in a Mouse Model of Pancreatic Cancer", PLOS ONE, 8(4): e61230, 9 pages.

Abdel-Rahman et al., (2007) "The High Frequency of cMET Over-Expression in Uveal Melanoma is Likely Through Altered Gene Regulation Rather Than Mutation and Amplification of the cMET Gene," Invest. Ophthalmol. Vis. Sci., 48(13): 4769.

Agarwal et al., (2013) "A Pictet-Spengler Ligation for Protein Chemical Modification," Proc. Natl. Acad. Sci., USA, 110: 46-51.

Al-Lazikani et al. (1997) "Standard Conformations for the Canonical Structures of Immunoglobulins," J. Mol. Biol., 273: 927-948.

Allen (1999) "The Art, Science and Technology of Pharmaceutical Compounding," Fifth Edition, American Pharmacists Association, Washington D.C.

Altschul et al. (1990) "Basic Local Alignment Search Tool," J. Mol. Biol., 215: 403-410.

Altschul et al. (1997) "Gapped BLAST and PSI-BLAST: A New Generation of Protein Database Search Programs," Nucleic Acids Res., 25: 3389-3402.

Andres et al. (2019) "Inhibition of the MET Kinase Activity and Cell Growth in MET-Addicted Cancer Cells by Bi-Paratopic Linking," Journal of Molecular Biology, 40 pages.

Bancroft et al. (1986) "Regulation of macrophage Ia expression in mice with severe combined immunodeficiency: induction of Ia expression by a T cell-independent mechanism," J. Immunol. 137(1): 4-9.

Bean et al. (2007) "MET amplification occurs with or without T790M mutations in EGFR mutant lung tumors with acquired resistance to gefitinib or erlotinib," Proc. Natl. Acad. Sci., 104(52): 20932-20937.

Bendig (1995) "Humanization of Rodent Monoclonal Antibodies by CDR Grafting," Methods: A Companion to Methods in Enzymology, 8: 83-93.

Boerman and Oyen (2011) "Immuno-PET of Cancer: A Revival of Antibody Imaging," Journal of Nuclear Medicine, 52(8): 1171-1172.

Boersma and Pluckhun (2011) "DARPins and Other Repeat Protein Scaffolds: Advances in Engineering and Applications", Curr. Opin. Biotechnol., 22: 849-857.

Camidge et al. (2018) "An Open-Label, Multicenter, Phase 1 Study of ABBV-399 (Telisotuzumab Vedotin, Teliso-V) as Monotherapy (T) and in Combination with Erlotinib (T+E) in Non-Small Cell Lung Cancer (NSCLC)" Presented at the European Society for Medical Oncology Annual Congress • Munich, Germany • Oct. 19-23, 2018.

Carrico et al. (2007) "Introducing Genetically Encoded Aldehydes into Proteins," Nat. Chem. Biol., 3: 321-322.

Casi et al. (2012) "Antibody-Drug Conjugates: Basic Concepts, Examples and Future Perspectives," Journal of Controlled Release 161: 422-428.

Casset et al. (2003) "A Peptide Mimetic of an Anti-CD4 Monoclonal Antibody by Rational Design," Biochemical and Biophysical Research Communications, 307: 198-205.

Chen et al. (2017) "Tubulin Inhibitor-Based Antibody-Drug Conjugates for Cancer Therapy," Molecules 22(8): 1-28.

Chen et al. (1995) "Enhancement and Destructions of Antibody Function by Somatic Mutation: Unequal Occurrence is Controlled by V Gene Combinatorial Associations," The EMBO Journal, 14(12): 2784-2794.

Cheng et al. (2018) "Phase 2 Study of Tepotinib + Gefitinib in MET-Positive/Epidermal Growth Factor Receptor-Mutant NSCLC," Munich 2018 ESMO Congress, 15 pages.

Cho et al. (2018) "JNJ-61186372 (JNJ-372), an EGFR-cMET Bispecific Antibody, in Advanced Non-Small Cell Lung Cancer (NSCLC): An Update on Phase 1 Results," Presented at the 43rd Annual Congress of the European Society for Medical Oncology, Oct. 19-23, 2018, Munich, Germany.

COLLINS (2007) "ImageJ for Microscopy," BioTechniques, 43: S25-S30.

Colman (1994) "Effects of Amino Acid Sequence Changes on Antibody-Antigen interactions," Research in Immunology, Elsevier, NY, 145(1): 33-36.

Czyz (2018) "HGF/c-MET Signaling in Melanocytes and Melanoma," International Journal of Molecular Sciences, 19(12): 3844-3856.

Deri et al. (2015) "p-SCN-Bn-HOPO: A Superior Bifunctional Chelator for 89Zr ImmunoPET," Bioconjugate Chem., 26(12): 2579-2591.

Desole et al. (2021) "Engineering, Characterization, and Biological Evaluation of an Antibody Targeting the HGF Receptor," Frontiers in Immunology, vol. 12, Article 775151.

Dicara et al. (2017) "Characterization and Structural Determination of a New Anti-MET Function-Blocking Antibody with Binding Epitope Distinct from the Ligand Binding Domain," Sci. Reports, 7:9000 pp. 1-13 and Supplementary Information pp. 1-15.

Dinter et al. (2015) "Inverse Agonistic Action of 3-Iodothyronamine at the Human Trace Amine-Associated Receptor 5," PLoS ONE 10(2): e0117774.

Doronina et al. (2003) "Development of Potent Monoclonal Antibody Auristatin Conjugates for Cancer Therapy," Nature Biotechnology, 21(7): 778-784.

Ducry (2010) "Antibody—Drug Conjugates: Linking Cytotoxic Payloads to Monoclonal Antibodies," Bioconjugate Chem., 21 : 5-13.

Ducry (2013) "Antibody-Drug Conjugates," Humana Press, Springer Protocols, 315 pages.

Ehring (1999) "Hydrogen Exchange/Electrospray Ionization Mass Spectrometry Studies of Structural Features of Proteins and Protein/Protein Interactions," Analytical Biochemistry, 267(2): 252-259.

Engen and Smith (2001) "The Basics of Ion Chromatography," Anal. Chem., 73: 256A-265A.

Esmaeli et al. (2010) "GPNMB Expression in Uveal Melanoma: A Potential for Targeted Therapy," Melanom Res., 20(3): 184-190.

Fan et al. (2015) "Bispecific Antibodies and Their Applications," J. Hematology & Oncology, 8: 130, 14 pages.

Ferrucci et al. (2014) "A HGF/cMET Autocrine Loop Is Operative in Multiple Myeloma Bone Marrow Endothelial Cells and May Represent a Novel Therapeutic Target," Cancer Research, 20: 5796-5807.

(56) References Cited

OTHER PUBLICATIONS

Fleury et al. (2000) "Structural Evidence for Recognition of a Single Epitope by Two Distinct Antibodies," Structure Function, and Genetics, 40: 572-578.
Freise et al. (2015) "In Vivo imaging with Antibodies and Engineered Fragments," Molecular Immunology, Pergamon, 67(2): 142-152.
Gherardi et al. (2003) "Functional Map and Doman Structure of MET, The Product of the c-met Protooncogene and Receptor for Hepatocyte Growth Factor/Scatter Factor," PNAS, 100(21): 12039-12044.
Godar et al. (2016) "Dual Anti-idiotypic Purification of a Novel, Native-format Biparatopic Anti-MET Antibody with Improved In Vitro and In Vivo Efficacy," Scientific Reports, 6: 31621; 1-12, DOI:10.1038/srep31621.
Gonnet et al. (1992) "Exhaustive Matching of the Entire Protein Sequence Database," Science 256: 1443-1445.
Grandal et al. (2017) "Simultaneous Targeting of Two Distinct Epitopes on MET Effectively Inhibits MET- and HGF-Driven Tumor Growth by Multiple Mechanisms," Molecular Cancer Therapeutics, 16: 2780-2791.
Greenall et al. (2012) "Non-agonistic Bivalent Antibodies That Promote c-MET Degradation and Inhibit Tumor Growth and Others Specific for Tumor Related c-MET," PLOS One, Public Library of Science, US, 7(4): E34658.1-E34658.10.
Gstöttner et al. (2020) "Intact and Subunit-Specific Analysis of Bispecific Antibodies by Sheathless CE-MS," Analytica Chimica Acta, 1134: 18-27.
Hamblett et al. (2004) "Effects of Drug Loading on the Antitumor Activity of a Monoclonal Antibody Drug Conjugate," American Association for Cancer Research, 10(20): 7063-7070.
Han et al. (2017) "Analysis of Progress and Challenges for Various Patterns of c-MET-targeted Molecular Imaging: A Systematic Review," EJNMMI Research, Biomed Central Ltd., 7(1): 1-15.
Hochleitner et al., (2000) "Characterization of a Discontinuous Epitope of the Human Immunodeficiency Virus (HIV) Core Protein p24 by Epitope Excision and Differential Chemical Modification Followed by Mass Spectrometric Peptide Mapping Analysis," Protein Science, 9: 487-496.
Hofer et al. (2008) "An Engineered Selenocysteine Defines a Unique Class of Antibody Derivatives," Proc. Natl. Acad. Sci., USA, 105: 12451-12456.
Hollander et al. (2008) "Selection of Reaction Additives Used in the Preparation of Monomeric Antibody-Calicheamicin Conjugates," Bioconjugate Chem., 19: 358-361.
International Search Report and Written Opinion for International Application No. PCT/US2020/050865 dated Dec. 1, 2020, 19 pages.
International Search Report and Written Opinion, received for PCT/US2017/061757 on Apr. 4, 2018, 22 pages.
International Search Report and Written Opinion, received for PCT/US2020/019126 on Jun. 18, 2020, 16 pages.
Jagoda et al. (2012) "Immuno-PET of the Hepatocyte Growth Factor Receptor Met Using he 1-Armed Antibody Onartuzumab," The Journal of Nuclear Medicine, 53(10):1562-1600.
Jeger et al. (2010) "Site-Specific and Stoichiometric Modification of Antibodies by Bacterial Transglutaminase," Angew. Chem. Int. Ed., 49: 9995-9997.
Junghans et al. (1990) "Anti-Tac-H, A Humanized Antibody to the Interleukin 2 Receptor with New Features for Immunotherapy in Malignant and Immune Disorders," Cancer Research, 50: 14951502.
Kabat (1991) "Sequences of Proteins of Immunological Interest," National Institutes of Health, Bethesda, Md.
Kawakami et al. (2014) "Targeting MET Amplification as a New Oncogenic Driver," Cancers, 6: 1540-1552.
Kazane et al. (2012) "Self-Assembled Antibody Multimers through Peptide Nucleic Acid Conjugation," J. Am. Chem. Soc., [Epub: Dec. 4, 2012].
Kazane et al. (2013) "Self-Assembled Antibody Multimers through Peptide Nucleic Acid Conjugation" J. Am. Chem. Soc., 135: 340-346.
Klein et al. (2012) "Progress in Overcoming the Chain Association Issue in Bispecific Heterodimeric IgG Antibodies," mAbs, 4:6, 653-663, DOI:10.4161/mabs.21379.
Ku and Park (2005) "Biology of SNU Cell Lines," Cancer Res. Treat., 37(1): 1-19.
Kubo et al. (2009) "MET Gene Amplification or EGFR Mutation Activate MET in Lung Cancers Untreated with EGFR Tyrosine Kinase Inhibitors," Int. J. Cancer, 124(8): 1778-1784.
Liu et al. (2014) "LY2875358, a Neutralizing and Internalizing Anti-MET Bivalent Antibody, Inhibits HGF-Dependent and HGF-Independent MET Activation and Tumor Growth," Clinical Cancer Research, 20(23): 6059-6070.
Lutterbach et al. (2007) "Lung Cancer Cell Lines Harboring MET Gene Amplification Are Dependent on MET for Growth and Survival," Cancer Res., 67(5): 2081-2088.
Maccallum, et al. (1996) "Antibody-Antigen Interactions: Contact Analysis and Binding Site Topography," J. Mol. Biol., 262: 732-745.
Martens et al. (2006) "A Novel One-Armed Anti-c-Met Antibody Inhibits Glioblastoma Growth In vivo," Clin Cancer Res., 12(20): 6144-6152.
Martin et al. (1989) "Modeling Antibody Hypervariable Loops: A Combined Algorithm," Proc. Natl. Acad. Sci., USA, 86: 9268-9272.
Mottaghy et al. (2016) "Molecular Imaging Using PSMA PET/CT Versus Multiparametric MRI for Initial Staging of Prostate Cancer: Comparing Apples with Oranges?" Eur. J. Nucl. Med. Mol. Imaging, 43: 1397-1399.
Nair et al. (1994) "Induction of Squamous Differentiation by Interferon Beta in a Human Non-Small-Cell Lung Cancer Cell Line," J. Nat'l. Cancer Inst., 86(5): 378-383.
Nakamura et al. (2010) "The Discovery of Hepatocyte Growth Factor (HGF) and Its Significance for Cell Biology, Life Sciences and Clinical Medicine," Proc. Jpn. Acad., Ser. B 86: 588.
Nazarova et al. (2014) "Current Trends in the Treatment of Uveal Melanoma: A Review of the Problem," Malignant Tumors 4(11): 54-62 (Russian reference).
Nazarova et al. (2014) "Current Trends in the Treatment of Uveal Melanoma: A Review of the Problem," Malignant Tumors 4(11): 54-62 (English Abstract).
Nehoff et al. (2015) "A Combination of Tyrosine Kinase Inhibitors, Crizotinib and Dasatinib for the Treatment of Glioblastoma Multiforme," Oncotarget, 6(35): 37948-37964.
Accession No. NM_000236.2 To: Protein [Internet]. Bethesda (MD): National Library of Medicine (US), National Center for Biotechnology Information; [2018]—Accession No. NM_000236.2, "*Homo sapiens* Lipase C, Hepatic Type (LIPC), mRNA", cited on Nov. 11, 2018, [online], [retrieved on Sep. 15, 2023]. Retrieved from: https://www.ncbi.nlm.nih.gov/nuccore/ NM_000236.2 /, 4 pages.
Accession No. NM_001127500.2 To: Protein [Internet]. Bethesda (MD): National Library of Medicine (US), National Center for Biotechnology Information; [2018]—Accession No. NM_001127500.2, "*Homo sapiens* MET Proto-oncogene, Receptor Tyrosine Kinase (MET), Transcript Variant 1, mRNA", cited on Oct. 21, 2018, [online], [retrieved on Sep. 15, 2023]. Retrieved from: https://www.ncbi.nlm.nih.gov/nuccore/ NM_001127500.2 /, 6 pages.
Accession No. NM_001311330.1 To: Protein [Internet]. Bethesda (MD): National Library of Medicine (US), National Center for Biotechnology Information; [2020]—Accession No. NM_001311330.1, "Oreochromis Nitoticus Folliculogenesis Specific bHLH transcription Factor (figla), mRNA", cited on Apr. 13, 2020, [online], [retrieved on Sep. 15, 2023]. Retrieved from: https://www.ncbi.nlm.nih.gov/nuccore/ NM_001311330.1 /, 2 pages.
Olopade et al. (1992) "Molecular Analysis of Deletions of the Short Arm of Chromosome 9 in Human Gliomas," Cancer Research 52: 2523-2529.
Oosting et al. (2015) "89Zr-Bevacizumab PET Visualizes Heterogeneous Tracer Accumulation in Tumor Lesions of Renal Cell Carcinoma Patients and Differential Effects of Antiangiogenic Treatment," J. Nucl. Med. 56: 63-69.

(56) References Cited

OTHER PUBLICATIONS

Padlan et al. (1995) "Identification of Specificity-Determining Residues in Antibodies," FASEB J. 9(1): 133-139.
Pandya et al. (2015) "Di-macrocyclic Terephthalamide Ligands as Chelators for the PET Radionuclide Zirconium-89," Chem. Commun. (Camb), 51(12): 2301-2303.
Paul (1993) "Fundamental Immunology," Third Edition, Raven Press, NY, Chapter 9, pp. 292-295.
Pearson (1994) "Using the FASTA Program to Search Protein and DNA Sequence Databases," Methods Mol. Biol., 24: 307-331.
Pearson (2000) "Flexible Sequence Similarity Searching with the FASTA3 Program Package," Methods in Molecular Biology, 132: 185-219.
Perk et al. (2008) "Facile Radiolabeling of Monoclonal Antibodies and Other Proteins with Zirconium-89 or Gallium-68 for PET Imaging Using P-isothiocyanatoenzyl-desferrioxamine," Protocol Exchange, XP055750961.
Perk et al. (2008) "Quantitative PET Imaging of Met-expressing Human Cancer Xenografts with 89Zr-labelled Monoclonal Antibody DN30," European Journal of Nuclear Medicine and Molecular Imaging, 35(10): 1857-1867.
Perk et al. (2010) "p-Isothiocyanatobenzyl-desferrioxamine: A New Bifunctional Chelate for Facile Radiolabeling of Monoclonal Antibodies with Zirconium-89 for Immuno-PET Imaging," Eur. J. Nucl. Med. Mol. Imaging, 37: 250-259.
Petrick et al. (2016) "In Vitro and In Vivo Comparison of Selected Ga-68 and ZR-89 Labelled Siderophores," Mol. Imaging Biol., 18: 344-352.
Phillips (2008) "Targeting HER2-Positive Breast Cancer with Trastuzumab-DM1, an Antibody-Cytotoxic Drug Conjugate, " Cancer Res., 68: 9280-9290.
Powell et al. (1998) "Compendium of Excipients for Parenteral Formulations," PDA J. Pharm. Sci. Technol., 52: 238-311.
Prat et al. (2014) "Monoclonal Antibodies Against the MET/HGF Receptor and It's Ligand: Multitask Tools with Applications from Basic Research to Therapy," Biomedicines, 2: 359-383.
Rabuka et al. (2012) "Site-specific Chemical Protein Conjugation Using Genetically Encoded Aldehyde Tags," Nat. Protocols, 10: 1052-1067.
Raybould et al. (2019) "Public Baseline and Shared Response Structures Support the Theory of Antibody Repertoire Functional Commonality," PNAS, 116(10): 4025-4030.
Reineke, (2004) "Antibody Epitope Mapping Using Arrays of Synthetic Peptides," Methods Mol. Biol., 248: 443-463.
Rock et al. (2015) "Intracelluar Catabolismof an Antibody Drug Conjugate with a Noncleavable Linker," Drug Metabolism and Disposition, 43: 1341-1344.
Rosen et al. (2017) "A First-in-Human Phase I Study of a Bivalent MET Antibody, Emibetuzumab (LY2875358), as Monotherapy and in Combination with Erlotinib in Advanced Cancer," Clin. Cancer Res., 23(8): 1910-1919.
Rudikoff et al. (1982) "Single Amino Acid Substitution Altering Antigen-Binding Specificity," Proc. Natl. Acad. Sci. USA, 79: 1979-1983.
Ryan et al. (2001) "Polyclonal Antibody Production Against Chito-Oligosaccharides," Food & Agriculture Immunol., 13: 127-130.
Sameer et al. (2012) "Non-Agonistic Bivalent Antibodies That Promote c-MET Degradation and Inhibit Tumor Growth and Others Specific for Tumor Related c-MET," PLOS ONE, Public Library of Science, US, 7(4): e34658.1-e34658.10.
Sapra et al. (2013) "Monoclonal Antibody-Based Therapies in Cancer: Advances and Challenges," Pharmacol. & Therapeutics, 138: 452-469.
Schumacher et al. (2016) "Current Status: Site-Specific Antibody Drug Conjugates," J.Clin. Immunol., 36: 100-107.
Shaunak et al. (2006) "Site-specific PEGylation of Native Disulfide Bonds In Therapeutic Proteins," Nat. Chem. Biol., 2: 312-313.
Shields et al., (2002) "Lack of Fucose on Human IgG1 N-Linked Oligosaccharide Improves Binding to Human FcγRIII and Antibody-dependent Cellular Toxicity," JBC 277:26733.
Sierra and Tsao (2011) "c-MET as a Potential Therapeutic Target and Biomarker in Cancer," Ther. Adv. Med. Oncol., 3(S1): S21-S35.
Smith (1979) "In Vitro Properties of Epithelial Cell Lines Established from Human Carcinomas and Nonmalignant Tissue," J. Nat'l. Cancer Inst., 62(2): 225-230.
Surriga et al. (2013) "Crizotinib, a c-Met Inhibitor, Prevents Metastasis in a Metastatic Uveal Melanoma Model," Molecular Cancer Therapeutics, 12(12): 2817-2826.
Tamura et al. (2000) "Structural Correlates of an Anticarcinoma Antibody: Identification of Specificity-Determining Residues (SDRs) and Development of a Minimally Immunogenic Antibody Variant by Retention of SDRS Only," J. of Immunol., 164(3): 1432-1441.
Taylor et al. (1992) "A Transgenic Mouse That Expresses a Diversity of Human Sequence Heavy and Light Chain Immunoglobulins," Nucl. Acids Res., 20: 6287-6295.
Taylor et al. (2017) "AbbVie Pairs Up Another ADC Cancer Drug with Bristol-Myers Squibb's Opdvio," FierceBiotech, https://www.fiercebiotech.com/biotech/abbvie-pairs-up-another-adc-cancer-drug-bms-opdivo.
Tomer (2000) "Characterization of a Discontinuous Epitope of the Human Immunodeficiency Virus (HIV) Core Protein p24 by Epitope Excision and Differential Chemical Modification Followed by Mass Spectrometric Peptide Mapping Analysis," Protein Science, 9:487-496.
Tsao et al. (2001) "Hepatocyte Growth Factor Is Predominantly Expressed by the Carcinoma Cells in Non-Small-Cell Lung Cancer," Human Pathology, 32(1): 57-65.
Vajdos et al. (2002) "Comprehensive Functional Maps of the Antigen-Binding Site of an Anti-ErbB2 Antibody Obtained with Shotgun Scanning Mutagenesis," J Mol. Biol., 320: 415-428.
Van de Watering et al. (2014) "Zirconium-89 Labeled Antibodies: A New Tool for Molecular Imaging in Cancer Patients," BioMed Research International, vol. 2014, Article ID 203601 (13 pages).
Van Dongen et al. (2007) "Immuno-PET: A Navigator in Monoclonal Antibody Development and Applications," The Oncologist, 12: 1379-1389.
Vordermark and Brown, (2003) "Evaluation of Hypoxia-Inducible Factor-1α (HIF-1α) As An Intrinsic Marker of Tumor Hypoxia in U87 MG Human Glioblastoma: In vitro and Xenograft Studies," Int. J. Radiation Biol., 56(4): 1184-1193.
Vosjan et al. (2010) "Conjugation and Radiolabeling of Monoclonal Antibodies with Sirconium-89 for PET Imaging Using the Bifunctional Chelate p-isothiocyanatobenzyl-desferrioxamine," Nature Protocols, 5(4): 739-743.
Vugts et al. (2017) "Comparison of the Octadentate Bifunctional Chelator DFO*- pPhe-NCS and The Clinically Used Hexadentate Bifunctional Chelator DFO-pPhe-NCS for 89Zr-immuno-PET", Eur. J Nucl. Med. Mol. Imaging, 44: 286-295, doi:10.1007/s00259-016-3499-x.
Wang et al. (2016) "ABBV-399, a c-Met Antibody-Drug Conjugate that Targets Both MET-Amplified and c-Met-Overexpressing Tumors, Irrespective of MET Pathway Dependence," Clinical Cancer Research, 23(4): 992-1000.
Wang et al. (2016) "Anti-c-Met Monoclonal Antibody ABT-700 Breaks Oncogene Addiction in Tumors with MET Amplification," BMC Cancer, 16: 105, pp. 1-14.
Williams et al. (2010) "GPNMB Expression in Uveal Melanoma: A Potential for Targeted Therapy," Melanom. Res., 20(3): 184-190.
Widdison et al. (2006) "Semisynthetic Maytansine Analogues for the Targeted Treatment of Cancer," J. Med. Chem., 49(14): 4392-4408.
Wolf et al. (2018) "Results of The Geometry Mono-1 Phase II Study for Evaluation of The MET Inhibitor Capmatinib (INC280) In Patients with MetΔex14 Mutated Advanced Non-Small Cell Lung Cancer," Munich 2018 ESMO Congress, 19 pages.
Wong et al. (2021) "Ab-Ligity: Identifying Sequence-Dissimilar Antibodies That Bind to the Same Epitope," mAbs, 13(1): 1-8.
Xiang et al. (2013) "Onartuzumab (MetMAb): Using Nonclinical Pharmacokinetic and Concentration-Effect Data to Support Clinical Development," Clin. Cancer Res., 19(18): 5068-5078.
Zhai et al. (2015) "Novel Bifunctional Cyclic Chelator for 89Zr Labeling-Radiolabeling and Targeting Properties of RGD Conjugates," Mol. Pharmaceutics, 12: 2142-2150.

(56) References Cited

OTHER PUBLICATIONS

Alzimami et al. (2014) "Comparison of Zr-89, 1-124, and F-18 Imaging Characteristics in PET Using Gate Monte Carlo Simulations: Imaging", International Journal of Radiation Oncology, 88: 502.
Chang et al. (2015) "Metabolic Competition in the Tumor Microenvironment Is a Driver of Cancer Progression", Cell, 162: 1229-1241.
Chatterjee et al. (2016) "A Humanized Antibody for Imaging Immune Checkpoint Ligand PD-L1 Expression in Tumors", Oncotarget, 7(9): 10215-10227.
Deng et al. (2016) "Preclinical Pharmacokinetics, Pharmacodynamics, Tissue Distribution, and Tumor Penetration of Anti-PD-L1 Monoclonal Antibody, an Immune Checkpoint Inhibitor", mAbs, 8(3): 593-603.
De Vries "Antibody Immunotherapy Imaging", Department of Medical Oncology University Medical Center Groningen, The Netherlands, 16 pages.
De Vries (2015) "MPDL3280A-imaging-IST-UMCG", ClinicalTrials.gov Identifier: NCT02453984, University Medical Center Groningen, 10 pages.
Dijkers et al. (2010) "Biodistribution of 89Zr-trastuzumab and PET Imaging of HER2-Positive Lesions in Patients with Metastatic Breast Cancer", Clinical Pharmacology and Therapeutics, 87(5): 586-592.
Gebhart et al. (2015) "Molecular Imaging as a Tool to Investigate Heterogeneity of Advanced HER2-positive Breast Cancer and to Predict Patient Outcome Under Trastuzumab Emtansine (T-DM1); The ZEPHIR Trial", Annals of Oncology Advance Access, 22 pages.
Herbst et al. (2014) "Predictive Correlates of Response to the Anti-PD-L1 Antibody MPDL3280A in Cancer Patients", Nature, 515(7528): 563-567.
Heskamp et al. (2015) "Noninvasive Imaging of Tumor PD-L1 Expression Using Radiolabeled Anti-PD-L1 Antibodies", Cancer Res., 75(14): 2928-2936.
Higashikawa et al. (2014) "64Cu-DOTA-Anti-CTLA-4 mAb Enabled PET Visualization of CTLA-4 on the T-Cell Infiltrating Tumor Tissues", PLoS One, 9(11): e109866, 8 pages.
Jauw et al. (2016) "Immuno-Positron Emission Tomography with Zirconium-89-Labeled Monoclonal Antibodies in Oncology: What Can We Learn from Initial Clinical Trials?" Frontiers in Pharmacology, vol. 7, Article 131, 15 pages.
Jing et al. (2015) "Combined Immune Checkpoint Protein Blockade and Low Dose Whole Body Irradiation as Immunotherapy for Myeloma", J. for Immuno. Therapy of Cancer, 3:2, pp. 1-15.
Josefsson et al. (2016) "Imaging Biodistribution, and Dosimetry of Radionuclide-Labeled PD-L1 Antibody in an Immunocompetent Mouse Model of Breast Cancer," Cancer Research, 76(2): 472-479.
Knight et al. (2016) "Scaling-down Antibody Radiolabeling Reactions with Zirconium-89", Dalton Trans., 45: 6343-6347.
Lamberts et al. (2015) "ImmunoPET with Anti-Mesothelin Antibody in Patients with Pancreatic and Ovarian Cancer Before Anti-Mesothelin Antibody-Drug Conjugate Treatment", Clinical Cancer Research, 22(7): 1642-1652.
Li and Zhu (2016) "Immuno-PET Imagining Using 89Zr Labeled PD-L1 Antibody in Non-small Cell Lung Cancer Xenograft", Journal of Nuclear Medicine, 57(Suppl. 2): 337.
Maute et al. (2015) "Engineering High-affinity PD-1 Variants for Optimized Immunotherapy and Immuno-PET Imaging", Proc Natl Acad Sci USA, 112(47): E6506-E6514.
Mindt et al. (2014) "Octadentate Bifuntional Chelating Agent for Zr-89 Based Imagining Probes", Technology Opportunity, Ref. No. UZ-15/736, 1 page.
Natarajan et al. (2015) "Novel Radiotracer for ImmunoPET Imaging of PD-1 Checkpoint Expression on Tumor Infiltrating Lymphocytes", Bioconjug Chem., 26(10): 2062-2069.
NCT03780725 on Dec. 19, 2018, ClinicalTrials.gov Archive, "This Study Tests How BI 754111 is Distributed in Patients with Advanced Non-small Cell Lung Cancer or Patients with Head and Neck Cancer Who Are Treated with BI754091", https://clinicaltrials.gov/ct2/show/NCT03780725.
Nijland et al. (2019) "Molecular Imaging Using Radiolabeled Atezolizumab to Assess Atezolizumab Biodistribution in Lymphoma Patients", University Medical Center Groningen, ClinicalTrials.gov Identifier: NCT03850028, 11 pages.
Patra et al. (2014) "An Octadentate Bifunctional Chelating Agent for the Development of Stable Zirconium-89 Based Molecular Imaging Probes", Chem. Commun., 50: 11523-11525.
Price et al. (2014) "H6phospa-trastuzumab: Bifunctional Methylenephosphonate-Based Chelator with 89Zr, 111In and 177Lu", Dalton Trans., 43(1): 119-131.
Slizys and Widnersson (2016) "The New "Pet" On the Block: Radio Imaging with Zirconium-89", FPA Patent Attorneys, 5 pages.
Tavare et al. (2016) "An Effective Immuno-PET Imaging Method to Monitor CD8-Dependent Responses to Immunotherapy," Cancer Research, 76(1): 73-82.
Tavare et al. (2014) "Engineered Antibody Fragments for Immuno-PET Imaging of Endogenous CD8+ T Cells in Vivo", Proceeding of the National Academy of Sciences of the USA, 111(3): 1108-1113.
Tavare et al. (2015) Anti-CD8 ImmunoPET Detection of CD8 + Tumor Infiltrating Lymphocytes! http://www.imaginab.com/WMIC2014%20TIL%20Poster_Tavare%20(Uploaded).pdf.
Tavare et al. (2015) "Detection of Antibody Therapy-Induced Anti-Tumor Immune Responses Using Anti-CD8 Immuno-Pet", J. Immunother. Cancer, vol. 3, Suppl. 2, p. 391.
Tavare et al. (2015) "Immuno-PET of Murine T Cell Reconstitution Postadoptive Stem Cell Transplantation Using Anti-CD4 and Anti-CD8 Cys-Diabodies", The Journal of Nuclear Medicine, 56(8): 1258-1264.
Tavare et al. (2015) Supplementary Data page S14; https://cancerres.aarcrjournals.org/content/canres/suppl/2016/02/04/0008-5472.CAN-15-1707.DC1/151683_2_supp_0_nwnncx.pdf.

* cited by examiner

Day 0 images are not available due to a scanner malfunction

Biodistribution Results for Tumor Xenografts

Biodistribution (%ID/g) of $^{89}$Zr-DFO-H4H14639D in NCI-H441 (MET Moderate) Tumor Bearing Mice Biodistribution (Tumor:Blood) of $^{89}$Zr-DFO-H4H14639D in NCI-H441 (MET Moderate) Tumor

SEQUENCE LISTING

```
Sequence total quantity: 158
SEQ ID NO: 1            moltype = DNA  length = 372
FEATURE                 Location/Qualifiers
source                  1..372
                        mol_type = other DNA
                        organism = Homo sapiens
SEQUENCE: 1
caggtgcagc tgcaggagtc gggcccagga ctggtgaagc cttcggagac cctgtccctc  60
acctgcactg tctctggtga ctccatcagt agttactatt ggacctggat ccggcagccc  120
ccagggaagg gactggagtg gattgggtat atcttttaca ggggggggcac cacctacaac  180
ccctccctca agagtcgagt caccatatca gtagacacgt ccaagaacca gttctccctg  240
aagttgaggt ctgtgaccgc cgcagacacg gccgtgtatt actgtgcgag gggagacgat  300
```

-continued

```
cttttagtgg tgacaagtgt ctactggtac atcgatctct ggggccgtgg caccctggtc  360
accgtctcct ca                                                      372

SEQ ID NO: 2            moltype = AA  length = 124
FEATURE                 Location/Qualifiers
source                  1..124
                        mol_type = protein
                        organism = Homo sapiens
SEQUENCE: 2
QVQLQESGPG LVKPSETLSL TCTVSGDSIS SYYWTWIRQP PGKGLEWIGY IFYRGGTTYN  60
PSLKSRVTIS VDTSKNQFSL KLRSVTAADT AVYYCARGDD LLVVTSVYWY IDLWGRGTLV  120
TVSS                                                               124

SEQ ID NO: 3            moltype = DNA  length = 24
FEATURE                 Location/Qualifiers
source                  1..24
                        mol_type = other DNA
                        organism = Homo sapiens
SEQUENCE: 3
ggtgactcca tcagtagtta ctat                                         24

SEQ ID NO: 4            moltype = AA  length = 8
FEATURE                 Location/Qualifiers
source                  1..8
                        mol_type = protein
                        organism = Homo sapiens
SEQUENCE: 4
GDSISSYY                                                           8

SEQ ID NO: 5            moltype = DNA  length = 21
FEATURE                 Location/Qualifiers
source                  1..21
                        mol_type = other DNA
                        organism = Homo sapiens
SEQUENCE: 5
atcttttaca ggggggcac c                                             21

SEQ ID NO: 6            moltype = AA  length = 7
FEATURE                 Location/Qualifiers
source                  1..7
                        mol_type = protein
                        organism = Homo sapiens
SEQUENCE: 6
IFYRGGT                                                            7

SEQ ID NO: 7            moltype = DNA  length = 54
FEATURE                 Location/Qualifiers
source                  1..54
                        mol_type = other DNA
                        organism = Homo sapiens
SEQUENCE: 7
gcgaggggag acgatctttt agtggtgaca agtgtctact ggtacatcga tctc        54

SEQ ID NO: 8            moltype = AA  length = 18
FEATURE                 Location/Qualifiers
source                  1..18
                        mol_type = protein
                        organism = Homo sapiens
SEQUENCE: 8
ARGDDLLVVT SVYWYIDL                                                18

SEQ ID NO: 9            moltype = DNA  length = 360
FEATURE                 Location/Qualifiers
source                  1..360
                        mol_type = other DNA
                        organism = Homo sapiens
SEQUENCE: 9
caggtgcagc tggtggagtc tgggggaggc gtggtccagc ctgggggtc cctgagactc   60
tcctgtgcag cgtccggatt caccttcagt ggctatggca tgcactgggt ccgccaggct  120
ccaggcaagg ggctggagtg gatggcagtt atatggtatg atggaagtaa tgattactat  180
ccagactccg tgaagggccg attcaccatc tccagagaca attccaagaa cacgctgtat  240
ctgcaaatga acagcctgag agtcgaggac acggctgtgt attactgtgc gcgagatgcg  300
tgggacctac tacgttcctt tgactactgg ggccagggaa ccctggtcac cgtctcctca  360

SEQ ID NO: 10           moltype = AA  length = 120
FEATURE                 Location/Qualifiers
source                  1..120
                        mol_type = protein
                        organism = Homo sapiens
```

-continued

```
SEQUENCE: 10
QVQLVESGGG VVQPGGSLRL SCAASGFTFS GYGMHWVRQA PGKGLEWMAV IWYDGSNDYY  60
PDSVKGRFTI SRDNSKNTLY LQMNSLRVED TAVYYCARDA WDLLRSFDYW GQGTLVTVSS  120

SEQ ID NO: 11          moltype = DNA  length = 24
FEATURE                Location/Qualifiers
source                 1..24
                       mol_type = other DNA
                       organism = Homo sapiens
SEQUENCE: 11
ggattcacct tcagtggcta tggc                                         24

SEQ ID NO: 12          moltype = AA  length = 8
FEATURE                Location/Qualifiers
source                 1..8
                       mol_type = protein
                       organism = Homo sapiens
SEQUENCE: 12
GFTFSGYG                                                           8

SEQ ID NO: 13          moltype = DNA  length = 24
FEATURE                Location/Qualifiers
source                 1..24
                       mol_type = other DNA
                       organism = Homo sapiens
SEQUENCE: 13
atatggtatg atggaagtaa tgat                                         24

SEQ ID NO: 14          moltype = AA  length = 8
FEATURE                Location/Qualifiers
source                 1..8
                       mol_type = protein
                       organism = Homo sapiens
SEQUENCE: 14
IWYDGSND                                                           8

SEQ ID NO: 15          moltype = DNA  length = 39
FEATURE                Location/Qualifiers
source                 1..39
                       mol_type = other DNA
                       organism = Homo sapiens
SEQUENCE: 15
gcgcgagatg cgtgggacct actacgttcc tttgactac                         39

SEQ ID NO: 16          moltype = AA  length = 13
FEATURE                Location/Qualifiers
source                 1..13
                       mol_type = protein
                       organism = Homo sapiens
SEQUENCE: 16
ARDAWDLLRS FDY                                                     13

SEQ ID NO: 17          moltype = DNA  length = 363
FEATURE                Location/Qualifiers
source                 1..363
                       mol_type = other DNA
                       organism = Homo sapiens
SEQUENCE: 17
caggtgcagc tggtggagtc tgggggaggc gtggtccagc ctgggaggtc cctgagagtc  60
tcttgtgtag tgtctggatt caccttcagc agctttggca tgcattgggt ccgccaggct  120
ccagacaagg ggctggagtg ggtggcagtt atatggtatg atggaagtaa tgattactat  180
tcagactccg tgaagggccg attcaccatc tccagagaca attccaagaa cacgctgttt  240
ctacaaatga accgcctgag agccgaagac acggctgttt attactgtgc gcgagctaat  300
aactggaacc gttttgatgc ctttgatctc tggggccaag ggacaatggt caccgtctct  360
tca                                                                363

SEQ ID NO: 18          moltype = AA  length = 121
FEATURE                Location/Qualifiers
source                 1..121
                       mol_type = protein
                       organism = Homo sapiens
SEQUENCE: 18
QVQLVESGGG VVQPGRSLRV SCVVSGFTFS SFGMHWVRQA PDKGLEWVAV IWYDGSNDYY  60
SDSVKGRFTI SRDNSKNTLF LQMNRLRAED TAVYYCARAN NWNRFDAFDL WGQGTMVTVS  120
S                                                                  121

SEQ ID NO: 19          moltype = DNA  length = 24
FEATURE                Location/Qualifiers
source                 1..24
```

-continued

```
                        mol_type = other DNA
                        organism = Homo sapiens
SEQUENCE: 19
ggattcacct tcagcagctt tggc                                              24

SEQ ID NO: 20           moltype = AA  length = 8
FEATURE                 Location/Qualifiers
source                  1..8
                        mol_type = protein
                        organism = Homo sapiens
SEQUENCE: 20
GFTFSSFG                                                                8

SEQ ID NO: 21           moltype = DNA  length = 24
FEATURE                 Location/Qualifiers
source                  1..24
                        mol_type = other DNA
                        organism = Homo sapiens
SEQUENCE: 21
atatggtatg atggaagtaa tgat                                              24

SEQ ID NO: 22           moltype = AA  length = 8
FEATURE                 Location/Qualifiers
source                  1..8
                        mol_type = protein
                        organism = Homo sapiens
SEQUENCE: 22
IWYDGSND                                                                8

SEQ ID NO: 23           moltype = DNA  length = 42
FEATURE                 Location/Qualifiers
source                  1..42
                        mol_type = other DNA
                        organism = Homo sapiens
SEQUENCE: 23
gcgcgagcta ataactggaa ccgttttgat gcctttgatc tc                          42

SEQ ID NO: 24           moltype = AA  length = 14
FEATURE                 Location/Qualifiers
source                  1..14
                        mol_type = protein
                        organism = Homo sapiens
SEQUENCE: 24
ARANNWNRFD AFDL                                                         14

SEQ ID NO: 25           moltype = DNA  length = 372
FEATURE                 Location/Qualifiers
source                  1..372
                        mol_type = other DNA
                        organism = Homo sapiens
SEQUENCE: 25
gaggtgcagc tggtggagtc tgggggaggc ttggttcagc ctggagggtc cctgagactc  60
tcctgtgcag cctctggatt catcttcagt aattatgaaa tgaactgggt ccgccaggct  120
ccagggaagg gactggaatg gatttcatac attactagta gtggtaatat gaaatattac  180
gcagactctg tgaagggccg attcaccatc tccagagaca acgacaagaa ttcactgtat  240
ctgcaaatga gtagtctgag agtcgaggac acggctgttt attattgtgt gagaggaggg  300
cgatttttgg agtggttgac ctactacgtt atggtcgtct ggggccaagg gaccacggtc  360
accgtctcct ca                                                           372

SEQ ID NO: 26           moltype = AA  length = 124
FEATURE                 Location/Qualifiers
source                  1..124
                        mol_type = protein
                        organism = Homo sapiens
SEQUENCE: 26
EVQLVESGGG LVQPGGSLRL SCAASGFIFS NYEMNWVRQA PGKGLEWISY ITSSGNMKYY  60
ADSVKGRFTI SRDNDKNSLY LQMSSLRVED TAVYYCVRGG RFLEWLTYYV MVVWGQGTTV  120
TVSS                                                                    124

SEQ ID NO: 27           moltype = DNA  length = 24
FEATURE                 Location/Qualifiers
source                  1..24
                        mol_type = other DNA
                        organism = Homo sapiens
SEQUENCE: 27
ggattcatct tcagtaatta tgaa                                              24

SEQ ID NO: 28           moltype = AA  length = 8
FEATURE                 Location/Qualifiers
```

-continued

```
source                1..8
                      mol_type = protein
                      organism = Homo sapiens
SEQUENCE: 28
GFIFSNYE                                                        8

SEQ ID NO: 29         moltype = DNA  length = 24
FEATURE               Location/Qualifiers
source                1..24
                      mol_type = other DNA
                      organism = Homo sapiens
SEQUENCE: 29
attactagta gtggtaatat gaaa                                      24

SEQ ID NO: 30         moltype = AA  length = 8
FEATURE               Location/Qualifiers
source                1..8
                      mol_type = protein
                      organism = Homo sapiens
SEQUENCE: 30
ITSSGNMK                                                        8

SEQ ID NO: 31         moltype = DNA  length = 51
FEATURE               Location/Qualifiers
source                1..51
                      mol_type = other DNA
                      organism = Homo sapiens
SEQUENCE: 31
gtgagaggag ggcgattttt ggagtggttg acctactacg ttatggtcgt c        51

SEQ ID NO: 32         moltype = AA  length = 17
FEATURE               Location/Qualifiers
source                1..17
                      mol_type = protein
                      organism = Homo sapiens
SEQUENCE: 32
VRGGRFLEWL TYYVMVV                                              17

SEQ ID NO: 33         moltype = DNA  length = 360
FEATURE               Location/Qualifiers
source                1..360
                      mol_type = other DNA
                      organism = Homo sapiens
SEQUENCE: 33
caggtgcagc tggtggagtc tgggggaggc gtggtccagc ctgggaggtc cctgagactc  60
tcctgtgcag tgtctggatt caccttcagt agctatggca tgcactgggt ccgccaggct  120
ccaggcaagg ggctggagtg ggtggcaaat atttggtatg atggaactaa tgattactat  180
ccatactccg tgaagggccg attcaccatc tccagagaca attcccagaa cacactatat  240
ctgcaaatga acagcctgag agccgaggac acggctgtat attactgtgc gagagaggac  300
ttcattaact accggtcttt tgactattgg ggccagggaa ccctggtcac cgtctcctca  360

SEQ ID NO: 34         moltype = AA  length = 120
FEATURE               Location/Qualifiers
source                1..120
                      mol_type = protein
                      organism = Homo sapiens
SEQUENCE: 34
QVQLVESGGG VVQPGRSLRL SCAVSGFTFS SYGMHWVRQA PGKGLEWVAN IWYDGTNDYY  60
PYSVKGRFTI SRDNSQNTLY LQMNSLRAED TAVYYCARED FINYRSFDYW GQGTLVTVSS  120

SEQ ID NO: 35         moltype = DNA  length = 24
FEATURE               Location/Qualifiers
source                1..24
                      mol_type = other DNA
                      organism = Homo sapiens
SEQUENCE: 35
ggattcacct tcagtagcta tggc                                      24

SEQ ID NO: 36         moltype = AA  length = 8
FEATURE               Location/Qualifiers
source                1..8
                      mol_type = protein
                      organism = Homo sapiens
SEQUENCE: 36
GFTFSSYG                                                        8

SEQ ID NO: 37         moltype = DNA  length = 24
FEATURE               Location/Qualifiers
source                1..24
```

-continued

```
                        mol_type = other DNA
                        organism = Homo sapiens
SEQUENCE: 37
atttggtatg atggaactaa tgat                                           24

SEQ ID NO: 38           moltype = AA  length = 8
FEATURE                 Location/Qualifiers
source                  1..8
                        mol_type = protein
                        organism = Homo sapiens
SEQUENCE: 38
IWYDGTND                                                             8

SEQ ID NO: 39           moltype = DNA  length = 39
FEATURE                 Location/Qualifiers
source                  1..39
                        mol_type = other DNA
                        organism = Homo sapiens
SEQUENCE: 39
gcgagagagg acttcattaa ctaccggtct tttgactat                           39

SEQ ID NO: 40           moltype = AA  length = 13
FEATURE                 Location/Qualifiers
source                  1..13
                        mol_type = protein
                        organism = Homo sapiens
SEQUENCE: 40
AREDFINYRS FDY                                                       13

SEQ ID NO: 41           moltype = DNA  length = 372
FEATURE                 Location/Qualifiers
source                  1..372
                        mol_type = other DNA
                        organism = Homo sapiens
SEQUENCE: 41
caggtgcagc tggtggagtc tgggggaggc gtggtccagc cagggacgtc cctgagactc  60
tcctgtgtcg cgtctggatt caccttcaga aattttggaa tgcactgggt ccgccaggct  120
ccaggcaagg ggctggagtg ggtggcaaat atatggtttg acggaagtaa tgagaactat  180
gtcgagtcca ttcagggccg attcaccatc tccagagaca attccaagaa cacactgaat  240
ctgcagatga acagcctgag agccgaggac tcggctgtct attactgtgt gagagaggga  300
atcctaggaa ctactaatcc ttatgatgct tttgatgtct ggggccaagg gacaatggtc  360
accgtctctt ca                                                        372

SEQ ID NO: 42           moltype = AA  length = 124
FEATURE                 Location/Qualifiers
source                  1..124
                        mol_type = protein
                        organism = Homo sapiens
SEQUENCE: 42
QVQLVESGGG VVQPGTSLRL SCVASGFTFR NFGMHWVRQA PGKGLEWVAN IWFDGSNENY  60
VESIQGRFTI SRDNSKNTLN LQMNSLRAED SAVYYCVREG ILGTTNPYDA FDVWGQGTMV  120
TVSS                                                                 124

SEQ ID NO: 43           moltype = DNA  length = 24
FEATURE                 Location/Qualifiers
source                  1..24
                        mol_type = other DNA
                        organism = Homo sapiens
SEQUENCE: 43
ggattcacct tcagaaattt tgga                                           24

SEQ ID NO: 44           moltype = AA  length = 8
FEATURE                 Location/Qualifiers
source                  1..8
                        mol_type = protein
                        organism = Homo sapiens
SEQUENCE: 44
GFTFRNFG                                                             8

SEQ ID NO: 45           moltype = DNA  length = 24
FEATURE                 Location/Qualifiers
source                  1..24
                        mol_type = other DNA
                        organism = Homo sapiens
SEQUENCE: 45
atatggtttg acggaagtaa tgag                                           24

SEQ ID NO: 46           moltype = AA  length = 8
FEATURE                 Location/Qualifiers
```

```
source                  1..8
                        mol_type = protein
                        organism = Homo sapiens
SEQUENCE: 46
IWFDGSNE                                                    8

SEQ ID NO: 47           moltype = DNA  length = 51
FEATURE                 Location/Qualifiers
source                  1..51
                        mol_type = other DNA
                        organism = Homo sapiens
SEQUENCE: 47
gtgagagagg gaatcctagg aactactaat ccttatgatg cttttgatgt c      51

SEQ ID NO: 48           moltype = AA  length = 17
FEATURE                 Location/Qualifiers
source                  1..17
                        mol_type = protein
                        organism = Homo sapiens
SEQUENCE: 48
VREGILGTTN PYDAFDV                                           17

SEQ ID NO: 49           moltype = DNA  length = 378
FEATURE                 Location/Qualifiers
source                  1..378
                        mol_type = other DNA
                        organism = Homo sapiens
SEQUENCE: 49
caggtgcagc tggtggagtc tgggggaggc gtggtccagc ctgggaggtc cctgagactc  60
tcctgtgcag cgtctggatt caccttta gt aactttggaa tgcactgggt ccgccaggcg  120
ccaggcaagg gactggagtg ggtggcaggt atatggtttg atggaagtaa taaaaactat  180
atagactccg tgaagggccg attcaccatc tcaagagaca attccaagaa cacgctgtat  240
ctgcaaatga acagcctgag agccgaggac acggctgtgt attactgtgc gagagagggc  300
tatgattcgg ggactgatta tatcccctat gatatttttg atatttgggg ccaagggaca  360
atggtcaccg tctcttca                                          378

SEQ ID NO: 50           moltype = AA  length = 126
FEATURE                 Location/Qualifiers
source                  1..126
                        mol_type = protein
                        organism = Homo sapiens
SEQUENCE: 50
QVQLVESGGG VVQPGRSLRL SCAASGFTFS NFGMHWVRQA PGKGLEWVAG IWFDGSNKNY  60
IDSVKGRFTI SRDNSKNTLY LQMNSLRAED TAVYYCAREG YDSGTDYIPY DIFDIWGQGT  120
MVTVSS                                                       126

SEQ ID NO: 51           moltype = DNA  length = 24
FEATURE                 Location/Qualifiers
source                  1..24
                        mol_type = other DNA
                        organism = Homo sapiens
SEQUENCE: 51
ggattcacct ttagtaactt tgga                                   24

SEQ ID NO: 52           moltype = AA  length = 8
FEATURE                 Location/Qualifiers
source                  1..8
                        mol_type = protein
                        organism = Homo sapiens
SEQUENCE: 52
GFTFSNFG                                                     8

SEQ ID NO: 53           moltype = DNA  length = 24
FEATURE                 Location/Qualifiers
source                  1..24
                        mol_type = other DNA
                        organism = Homo sapiens
SEQUENCE: 53
atatggtttg atggaagtaa taaa                                   24

SEQ ID NO: 54           moltype = AA  length = 8
FEATURE                 Location/Qualifiers
source                  1..8
                        mol_type = protein
                        organism = Homo sapiens
SEQUENCE: 54
IWFDGSNK                                                     8

SEQ ID NO: 55           moltype = DNA  length = 57
```

```
FEATURE              Location/Qualifiers
source               1..57
                     mol_type = other DNA
                     organism = Homo sapiens
SEQUENCE: 55
gcgagagagg gctatgattc ggggactgat tatatcccct atgatatttt tgatatt     57

SEQ ID NO: 56        moltype = AA  length = 19
FEATURE              Location/Qualifiers
source               1..19
                     mol_type = protein
                     organism = Homo sapiens
SEQUENCE: 56
AREGYDSGTD YIPYDIFDI                                               19

SEQ ID NO: 57        moltype = DNA  length = 363
FEATURE              Location/Qualifiers
source               1..363
                     mol_type = other DNA
                     organism = Homo sapiens
SEQUENCE: 57
gaagtgcagc tggtggagtc tgggggaggc ttggtacagc ctggcacgtc cctgagactc  60
tcctgtgcag cctctggatt cacctttgat gattatgcca tgcactgggt ccggcaagct  120
ccagggaagg gcctggagtg ggtctcaggt attacttgga atagttataa catagactat  180
gctgactctg tgaagggccg attcaccatc tccagagaca acgccaagaa ctccctgtat  240
ctgcaaatga acagtctgag agctgaggac acggccttgt attactgtgc aaaagatgat  300
gactacagta actacgttta ctttgactac tggggccagg gaaccctggt caccgtctcc  360
tca                                                                363

SEQ ID NO: 58        moltype = AA  length = 121
FEATURE              Location/Qualifiers
source               1..121
                     mol_type = protein
                     organism = Homo sapiens
SEQUENCE: 58
EVQLVESGGG LVQPGTSLRL SCAASGFTFD DYAMHWVRQA PGKGLEWVSG ITWNSYNIDY  60
ADSVKGRFTI SRDNAKNSLY LQMNSLRAED TALYYCAKDD DYSNYVYFDY WGQGTLVTVS  120
S                                                                  121

SEQ ID NO: 59        moltype = DNA  length = 24
FEATURE              Location/Qualifiers
source               1..24
                     mol_type = other DNA
                     organism = Homo sapiens
SEQUENCE: 59
ggattcacct ttgatgatta tgcc                                         24

SEQ ID NO: 60        moltype = AA  length = 8
FEATURE              Location/Qualifiers
source               1..8
                     mol_type = protein
                     organism = Homo sapiens
SEQUENCE: 60
GFTFDDYA                                                           8

SEQ ID NO: 61        moltype = DNA  length = 24
FEATURE              Location/Qualifiers
source               1..24
                     mol_type = other DNA
                     organism = Homo sapiens
SEQUENCE: 61
attacttgga atagttataa cata                                         24

SEQ ID NO: 62        moltype = AA  length = 8
FEATURE              Location/Qualifiers
source               1..8
                     mol_type = protein
                     organism = Homo sapiens
SEQUENCE: 62
ITWNSYNI                                                           8

SEQ ID NO: 63        moltype = DNA  length = 42
FEATURE              Location/Qualifiers
source               1..42
                     mol_type = other DNA
                     organism = Homo sapiens
SEQUENCE: 63
gcaaaagatg atgactacag taactacgtt tactttgact ac                     42
```

-continued

```
SEQ ID NO: 64          moltype = AA  length = 14
FEATURE                Location/Qualifiers
source                 1..14
                       mol_type = protein
                       organism = Homo sapiens
SEQUENCE: 64
AKDDDYSNYV YFDY                                                   14

SEQ ID NO: 65          moltype = DNA  length = 360
FEATURE                Location/Qualifiers
source                 1..360
                       mol_type = other DNA
                       organism = Homo sapiens
SEQUENCE: 65
caggttcagc tggtgcagtc cggaactgag gtgaaggagc ctggggcctc agtgaaggtc  60
tcctgtaagg cctctggtta ctcctttacc acctatggta tcagctggct gcgacaggcc  120
cctggacaag gacttgagtg gatgggatgg atcagcactt acaatggtga cacaatctct  180
gcacagatgc tccaggacag agtcaccctg accgcagaca catccacgcg cacagcctac  240
atggaactga gaagcctgag atctgacgac acggccgtgt attactgtgc gagaggtcat  300
gagtatgata gtcttgttta ttcttactgg ggccagggaa ccctggtcac cgtctcctca  360

SEQ ID NO: 66          moltype = AA  length = 120
FEATURE                Location/Qualifiers
source                 1..120
                       mol_type = protein
                       organism = Homo sapiens
SEQUENCE: 66
QVQLVQSGTE VKEPGASVKV SCKASGYSFT TYGISWLRQA PGQGLEWMGW ISTYNGDTIS  60
AQMLQDRVTL TADTSTRTAY MELRSLRSDD TAVYYCARGH EYDSLVYSYW GQGTLVTVSS  120

SEQ ID NO: 67          moltype = DNA  length = 24
FEATURE                Location/Qualifiers
source                 1..24
                       mol_type = other DNA
                       organism = Homo sapiens
SEQUENCE: 67
ggttactcct ttaccaccta tggt                                        24

SEQ ID NO: 68          moltype = AA  length = 8
FEATURE                Location/Qualifiers
source                 1..8
                       mol_type = protein
                       organism = Homo sapiens
SEQUENCE: 68
GYSFTTYG                                                          8

SEQ ID NO: 69          moltype = DNA  length = 24
FEATURE                Location/Qualifiers
source                 1..24
                       mol_type = other DNA
                       organism = Homo sapiens
SEQUENCE: 69
atcagcactt acaatggtga caca                                        24

SEQ ID NO: 70          moltype = AA  length = 8
FEATURE                Location/Qualifiers
source                 1..8
                       mol_type = protein
                       organism = Homo sapiens
SEQUENCE: 70
ISTYNGDT                                                          8

SEQ ID NO: 71          moltype = DNA  length = 39
FEATURE                Location/Qualifiers
source                 1..39
                       mol_type = other DNA
                       organism = Homo sapiens
SEQUENCE: 71
gcgagaggtc atgagtatga tagtcttgtt tattcttac                        39

SEQ ID NO: 72          moltype = AA  length = 13
FEATURE                Location/Qualifiers
source                 1..13
                       mol_type = protein
                       organism = Homo sapiens
SEQUENCE: 72
ARGHEYDSLV YSY                                                    13

SEQ ID NO: 73          moltype = DNA  length = 360
```

-continued

```
FEATURE                Location/Qualifiers
source                 1..360
                       mol_type = other DNA
                       organism = Homo sapiens
SEQUENCE: 73
caggtgcagc tggtggagtc tgggggaggc gtggtccagc ctgggaggtc cctgagactc  60
tcctgtgcag cgtctggatt caccttcagt agttatgcca tgcactgggt ccgccaggct  120
ccaggcaggg ggctggagtg ggtggcggtt atatggcatg atggagatgt tgaatactat  180
gtagactccg tgaaggaccg attcaccatc tccagagaca attccaagag cacgctgtat  240
ctgcaaatga acagcctgag agccgaagat acggctttat attattgtgc gagagaggcg  300
tgggacctac tacgtccctt tgactattgg ggccagggaa ccctggtcac cgtctcctca  360

SEQ ID NO: 74          moltype = AA  length = 120
FEATURE                Location/Qualifiers
source                 1..120
                       mol_type = protein
                       organism = Homo sapiens
SEQUENCE: 74
QVQLVESGGG VVQPGRSLRL SCAASGFTFS SYAMHWVRQA PGRGLEWVAV IWHDGDVEYY  60
VDSVKDRFTI SRDNSKSTLY LQMNSLRAED TALYYCAREA WDLLRPFDYW GQGTLVTVSS  120

SEQ ID NO: 75          moltype = DNA  length = 24
FEATURE                Location/Qualifiers
source                 1..24
                       mol_type = other DNA
                       organism = Homo sapiens
SEQUENCE: 75
ggattcacct tcagtagtta tgcc                                         24

SEQ ID NO: 76          moltype = AA  length = 8
FEATURE                Location/Qualifiers
source                 1..8
                       mol_type = protein
                       organism = Homo sapiens
SEQUENCE: 76
GFTFSSYA                                                           8

SEQ ID NO: 77          moltype = DNA  length = 24
FEATURE                Location/Qualifiers
source                 1..24
                       mol_type = other DNA
                       organism = Homo sapiens
SEQUENCE: 77
atatggcatg atggagatgt tgaa                                         24

SEQ ID NO: 78          moltype = AA  length = 8
FEATURE                Location/Qualifiers
source                 1..8
                       mol_type = protein
                       organism = Homo sapiens
SEQUENCE: 78
IWHDGDVE                                                           8

SEQ ID NO: 79          moltype = DNA  length = 39
FEATURE                Location/Qualifiers
source                 1..39
                       mol_type = other DNA
                       organism = Homo sapiens
SEQUENCE: 79
gcgagagagg cgtgggacct actacgtccc tttgactat                         39

SEQ ID NO: 80          moltype = AA  length = 13
FEATURE                Location/Qualifiers
source                 1..13
                       mol_type = protein
                       organism = Homo sapiens
SEQUENCE: 80
AREAWDLLRP FDY                                                     13

SEQ ID NO: 81          moltype = DNA  length = 351
FEATURE                Location/Qualifiers
source                 1..351
                       mol_type = other DNA
                       organism = Homo sapiens
SEQUENCE: 81
gaggtgcagc tggtggagtc tggaggaggc ttggtccagc ctgggggggtc cctgagactc  60
tcctgtgcag cctctgggtt catcgtcacc accaactaca tgacctggct ccgccaggct  120
ccagggaagg ggctggagtg ggtctcactt atttatagca gtggtcacac atactacgca  180
gactccgtga agggccgatt caccatctcc agacacaatt ccaagaacac actgtatcta  240
```

-continued

```
caaatggaca gcctgagagc tgaggacacg gccgtgtatt actgtgcgag tgctttcgca  300
gcggatgttt ttgatatctg ggccaagggg acaatggtca ccgtctcttc a           351

SEQ ID NO: 82          moltype = AA  length = 117
FEATURE                Location/Qualifiers
source                 1..117
                       mol_type = protein
                       organism = Homo sapiens
SEQUENCE: 82
EVQLVESGGG LVQPGGSLRL SCAASGFIVT TNYMTWLRQA PGKGLEWVSL IYSSGHTYYA  60
DSVKGRFTIS RHNSKNTLYL QMDSLRAEDT AVYYCASAFA ADVFDIWGQG TMVTVSS     117

SEQ ID NO: 83          moltype = DNA  length = 24
FEATURE                Location/Qualifiers
source                 1..24
                       mol_type = other DNA
                       organism = Homo sapiens
SEQUENCE: 83
gggttcatcg tcaccaccaa ctac                                         24

SEQ ID NO: 84          moltype = AA  length = 8
FEATURE                Location/Qualifiers
source                 1..8
                       mol_type = protein
                       organism = Homo sapiens
SEQUENCE: 84
GFIVTTNY                                                           8

SEQ ID NO: 85          moltype = DNA  length = 21
FEATURE                Location/Qualifiers
source                 1..21
                       mol_type = other DNA
                       organism = Homo sapiens
SEQUENCE: 85
atttatagca gtggtcacac a                                            21

SEQ ID NO: 86          moltype = AA  length = 7
FEATURE                Location/Qualifiers
source                 1..7
                       mol_type = protein
                       organism = Homo sapiens
SEQUENCE: 86
IYSSGHT                                                            7

SEQ ID NO: 87          moltype = DNA  length = 33
FEATURE                Location/Qualifiers
source                 1..33
                       mol_type = other DNA
                       organism = Homo sapiens
SEQUENCE: 87
gcgagtgctt tcgcagcgga tgtttttgat atc                               33

SEQ ID NO: 88          moltype = AA  length = 11
FEATURE                Location/Qualifiers
source                 1..11
                       mol_type = protein
                       organism = Homo sapiens
SEQUENCE: 88
ASAFAADVFD I                                                       11

SEQ ID NO: 89          moltype = DNA  length = 372
FEATURE                Location/Qualifiers
source                 1..372
                       mol_type = other DNA
                       organism = Homo sapiens
SEQUENCE: 89
caggtgcagc tggtggagtc tgggggaggc gtggtccagc ctgggaggtc cctgagactc  60
tcctgttcag cgtctggatt ctccttcagt cactttggca tgcactgggt ccgccaggtt  120
ccaggcgggg gcctggagtg ggtgacaagt atatggtttg atggaagtaa tagatattat  180
gcagactcct tgaagggccg attcaccatc tccagagaca attccaagaa tactctgtat  240
ctggaaatga acagcctgag agccgaggac acggctgtgt attactgtgt gagagagggg  300
atactgggaa ctactaatcc ttatgatgtt tttgatgtct ggggtcaggg gacaatggtc  360
accgtctctt ca                                                      372

SEQ ID NO: 90          moltype = AA  length = 124
FEATURE                Location/Qualifiers
source                 1..124
                       mol_type = protein
                       organism = Homo sapiens
```

-continued

```
SEQUENCE: 90
QVQLVESGGG VVQPGRSLRL SCSASGFSFS HFGMHWVRQV PGGGLEWVTS IWFDGSNRYY  60
ADSLKGRFTI SRDNSKNTLY LEMNSLRAED TAVYYCVREG ILGTTNPYDV FDVWGQGTMV  120
TVSS                                                              124

SEQ ID NO: 91          moltype = DNA  length = 24
FEATURE                Location/Qualifiers
source                 1..24
                       mol_type = other DNA
                       organism = Homo sapiens
SEQUENCE: 91
ggattctcct tcagtcactt tggc                                        24

SEQ ID NO: 92          moltype = AA  length = 8
FEATURE                Location/Qualifiers
source                 1..8
                       mol_type = protein
                       organism = Homo sapiens
SEQUENCE: 92
GFSFSHFG                                                          8

SEQ ID NO: 93          moltype = DNA  length = 24
FEATURE                Location/Qualifiers
source                 1..24
                       mol_type = other DNA
                       organism = Homo sapiens
SEQUENCE: 93
atatggtttg atggaagtaa taga                                        24

SEQ ID NO: 94          moltype = AA  length = 8
FEATURE                Location/Qualifiers
source                 1..8
                       mol_type = protein
                       organism = Homo sapiens
SEQUENCE: 94
IWFDGSNR                                                          8

SEQ ID NO: 95          moltype = DNA  length = 51
FEATURE                Location/Qualifiers
source                 1..51
                       mol_type = other DNA
                       organism = Homo sapiens
SEQUENCE: 95
gtgagagagg ggatactggg aactactaat ccttatgatg tttttgatgt c          51

SEQ ID NO: 96          moltype = AA  length = 17
FEATURE                Location/Qualifiers
source                 1..17
                       mol_type = protein
                       organism = Homo sapiens
SEQUENCE: 96
VREGILGTTN PYDVFDV                                                17

SEQ ID NO: 97          moltype = DNA  length = 372
FEATURE                Location/Qualifiers
source                 1..372
                       mol_type = other DNA
                       organism = Homo sapiens
SEQUENCE: 97
gaggtgcagc tggtggagtc tgggggaggc ttggtacagc cggggggtc cctgagactc  60
tcctgtgcag cctctggatt cacctttaga agctatgtca tgagctggtt ccgccaggct  120
ccagggaagg ggctggagtg ggtctcagga atgagtggga gtggtggaag cacatcctac  180
gcagactccg tgaagggccg gttcaccatc tccagagaca attcaaagaa tacgctgtat  240
ctgctaatga acagcctgag aaccgaggac acggccgtat attattgtgc gaaagaaaac  300
ggggctaact ggaactacgg ctactacggt atggacgtct ggggccaagg gaccacggtc  360
accgtctcct ca                                                     372

SEQ ID NO: 98          moltype = AA  length = 124
FEATURE                Location/Qualifiers
source                 1..124
                       mol_type = protein
                       organism = Homo sapiens
SEQUENCE: 98
EVQLVESGGG LVQPGGSLRL SCAASGFTFR SYVMSWFRQA PGKGLEWVSG MSGSGGSTSY  60
ADSVKGRFTI SRDNSKNTLY LLMNSLRTED TAVYYCAKEN GANWNYGYYG MDVWGQGTTV  120
TVSS                                                              124

SEQ ID NO: 99          moltype = DNA  length = 24
FEATURE                Location/Qualifiers
```

```
source                1..24
                      mol_type = other DNA
                      organism = Homo sapiens
SEQUENCE: 99
ggattcacct ttagaagcta tgtc                                        24

SEQ ID NO: 100        moltype = AA  length = 8
FEATURE               Location/Qualifiers
source                1..8
                      mol_type = protein
                      organism = Homo sapiens
SEQUENCE: 100
GFTFRSYV                                                          8

SEQ ID NO: 101        moltype = DNA  length = 24
FEATURE               Location/Qualifiers
source                1..24
                      mol_type = other DNA
                      organism = Homo sapiens
SEQUENCE: 101
atgagtggga gtggtggaag caca                                        24

SEQ ID NO: 102        moltype = AA  length = 8
FEATURE               Location/Qualifiers
source                1..8
                      mol_type = protein
                      organism = Homo sapiens
SEQUENCE: 102
MSGSGGST                                                          8

SEQ ID NO: 103        moltype = DNA  length = 51
FEATURE               Location/Qualifiers
source                1..51
                      mol_type = other DNA
                      organism = Homo sapiens
SEQUENCE: 103
gcgaaagaaa acggggctaa ctggaactac ggctactacg gtatggacgt c          51

SEQ ID NO: 104        moltype = AA  length = 17
FEATURE               Location/Qualifiers
source                1..17
                      mol_type = protein
                      organism = Homo sapiens
SEQUENCE: 104
AKENGANWNY GYYGMDV                                                17

SEQ ID NO: 105        moltype = DNA  length = 360
FEATURE               Location/Qualifiers
source                1..360
                      mol_type = other DNA
                      organism = Homo sapiens
SEQUENCE: 105
caggtgcagc tggtggagtc tgggggaggc gtggtccagc ctgggaggtc cctgagactc  60
tcctgtgtag cgtctggatt ctccttcagt aactttggca tgcactgggt ccgccaggct  120
ccaggcaagg ggctggagtg ggtggcaatt atatggtatg atggaagtaa taaatactat  180
tcagactccg tgaagggccg cttcaccatc tccagagaca attccaagaa cacgctgtat  240
ctgcaaatga acagcctgag agtcgacgac acggctgtgt attactgtgc gagattcgat  300
cgctggaaat ttgacgcttt tgatatctgg ggccaaggga caatggtcac cgtctcttca  360

SEQ ID NO: 106        moltype = AA  length = 120
FEATURE               Location/Qualifiers
source                1..120
                      mol_type = protein
                      organism = Homo sapiens
SEQUENCE: 106
QVQLVESGGG VVQPGRSLRL SCVASGFSFS NFGMHWVRQA PGKGLEWVAI IWYDGSNKYY  60
SDSVKGRFTI SRDNSKNTLY LQMNSLRVDD TAVYYCARFD RWKFDAFDIW GQGTMVTVSS  120

SEQ ID NO: 107        moltype = DNA  length = 24
FEATURE               Location/Qualifiers
source                1..24
                      mol_type = other DNA
                      organism = Homo sapiens
SEQUENCE: 107
ggattctcct tcagtaactt tggc                                        24

SEQ ID NO: 108        moltype = AA  length = 8
FEATURE               Location/Qualifiers
source                1..8
```

```
                       mol_type = protein
                       organism = Homo sapiens
SEQUENCE: 108
GFSFSNFG                                                          8

SEQ ID NO: 109         moltype = DNA  length = 24
FEATURE                Location/Qualifiers
source                 1..24
                       mol_type = other DNA
                       organism = Homo sapiens
SEQUENCE: 109
atatggtatg atggaagtaa taaa                                        24

SEQ ID NO: 110         moltype = AA  length = 8
FEATURE                Location/Qualifiers
source                 1..8
                       mol_type = protein
                       organism = Homo sapiens
SEQUENCE: 110
IWYDGSNK                                                          8

SEQ ID NO: 111         moltype = DNA  length = 39
FEATURE                Location/Qualifiers
source                 1..39
                       mol_type = other DNA
                       organism = Homo sapiens
SEQUENCE: 111
gcgagattcg atcgctggaa atttgacgct tttgatatc                        39

SEQ ID NO: 112         moltype = AA  length = 13
FEATURE                Location/Qualifiers
source                 1..13
                       mol_type = protein
                       organism = Homo sapiens
SEQUENCE: 112
ARFDRWKFDA FDI                                                    13

SEQ ID NO: 113         moltype = DNA  length = 360
FEATURE                Location/Qualifiers
source                 1..360
                       mol_type = other DNA
                       organism = Homo sapiens
SEQUENCE: 113
caggtgcagc tggtggagtc tgggggaggc gtggtccagc ctgggaggtc cctgagactc  60
tcctgtgcag cgtctggatt caccttcagt agctttgcca tgcactgggt ccgccaggct  120
ccaggcaagg ggctggagtg ggtggcagtt atatggtatg atggaagtaa tgattactat  180
gcagcctccg tgaagggccg tttcaccatc tccagagaca attccaagaa cacgctgtat  240
ctggaaatga acagactgag agccgaggac acggctgtgt atcactgtgc gagagataac  300
tggaattact ggggggtat ggacgtctgg ggccaaggga ccacggtcac cgtctcctca  360

SEQ ID NO: 114         moltype = AA  length = 120
FEATURE                Location/Qualifiers
source                 1..120
                       mol_type = protein
                       organism = Homo sapiens
SEQUENCE: 114
QVQLVESGGG VVQPGRSLRL SCAASGFTFS SFAMHWVRQA PGKGLEWVAV IWYDGSNDYY  60
AASVKGRFTI SRDNSKNTLY LEMNRLRAED TAVYHCARDN WNYWGGMDVW GQGTTVTVSS  120

SEQ ID NO: 115         moltype = DNA  length = 24
FEATURE                Location/Qualifiers
source                 1..24
                       mol_type = other DNA
                       organism = Homo sapiens
SEQUENCE: 115
ggattcacct tcagtagctt tgcc                                        24

SEQ ID NO: 116         moltype = AA  length = 8
FEATURE                Location/Qualifiers
source                 1..8
                       mol_type = protein
                       organism = Homo sapiens
SEQUENCE: 116
GFTFSSFA                                                          8

SEQ ID NO: 117         moltype = DNA  length = 24
FEATURE                Location/Qualifiers
source                 1..24
                       mol_type = other DNA
```

-continued

```
                      organism = Homo sapiens
SEQUENCE: 117
atatggtatg atggaagtaa tgat                                        24

SEQ ID NO: 118        moltype = AA  length = 8
FEATURE               Location/Qualifiers
source                1..8
                      mol_type = protein
                      organism = Homo sapiens
SEQUENCE: 118
IWYDGSND                                                          8

SEQ ID NO: 119        moltype = DNA  length = 39
FEATURE               Location/Qualifiers
source                1..39
                      mol_type = other DNA
                      organism = Homo sapiens
SEQUENCE: 119
gcgagagata actggaatta ctggggggt atggacgtc                         39

SEQ ID NO: 120        moltype = AA  length = 13
FEATURE               Location/Qualifiers
source                1..13
                      mol_type = protein
                      organism = Homo sapiens
SEQUENCE: 120
ARDNWNYWGG MDV                                                    13

SEQ ID NO: 121        moltype = DNA  length = 375
FEATURE               Location/Qualifiers
source                1..375
                      mol_type = other DNA
                      organism = Homo sapiens
SEQUENCE: 121
gaggtgcagc tgttggagtc tgggggaggc tgggtgcagc cggggggtc cctgagactc  60
tcctgtgcag cctctggatt cgcctttagt aattatgcca tgaactgggt ccgccagact  120
ccagggaagg ggctggagtg ggtctcagtt attagtagta gtggtggaaa cacatactac  180
gcagactccg tgaagggccg gttcgccatc tccagagaca attccaggga tacgctgcat  240
ctgcaaatga acagactgag agtcgaggac acggccgtct attactgtgc gaaagaaata  300
cgtccgtatt acgatctttc ctactattac ggtatggacg tctggggcca agggaccacg  360
gtcaccgtct cctca                                                  375

SEQ ID NO: 122        moltype = AA  length = 125
FEATURE               Location/Qualifiers
source                1..125
                      mol_type = protein
                      organism = Homo sapiens
SEQUENCE: 122
EVQLLESGGG WVQPGGSLRL SCAASGFAFS NYAMNWVRQT PGKGLEWVSV ISSSGGNTYY  60
ADSVKGRFAI SRDNSRDTLH LQMNRLRVED TAVYYCAKEI RPYYDLSYYY GMDVWGQGTT  120
VTVSS                                                             125

SEQ ID NO: 123        moltype = DNA  length = 24
FEATURE               Location/Qualifiers
source                1..24
                      mol_type = other DNA
                      organism = Homo sapiens
SEQUENCE: 123
ggattcgcct ttagtaatta tgcc                                        24

SEQ ID NO: 124        moltype = AA  length = 8
FEATURE               Location/Qualifiers
source                1..8
                      mol_type = protein
                      organism = Homo sapiens
SEQUENCE: 124
GFAFSNYA                                                          8

SEQ ID NO: 125        moltype = DNA  length = 24
FEATURE               Location/Qualifiers
source                1..24
                      mol_type = other DNA
                      organism = Homo sapiens
SEQUENCE: 125
attagtagta gtggtggaaa caca                                        24

SEQ ID NO: 126        moltype = AA  length = 8
FEATURE               Location/Qualifiers
source                1..8
```

```
                        mol_type = protein
                        organism = Homo sapiens
SEQUENCE: 126
ISSSGGNT                                                          8

SEQ ID NO: 127          moltype = DNA  length = 54
FEATURE                 Location/Qualifiers
source                  1..54
                        mol_type = other DNA
                        organism = Homo sapiens
SEQUENCE: 127
gcgaaagaaa tacgtccgta ttacgatctt tcctactatt acggtatgga cgtc       54

SEQ ID NO: 128          moltype = AA  length = 18
FEATURE                 Location/Qualifiers
source                  1..18
                        mol_type = protein
                        organism = Homo sapiens
SEQUENCE: 128
AKEIRPYYDL SYYYGMDV                                               18

SEQ ID NO: 129          moltype = DNA  length = 348
FEATURE                 Location/Qualifiers
source                  1..348
                        mol_type = other DNA
                        organism = Homo sapiens
SEQUENCE: 129
caggtgcagc tgcaggagtc gggcccagga ctggtgaagt cttcggagac cctgtccctc  60
acctgcactg tctctggtgg ctccatcaga aatttctact ggagctggct ccggcagccc  120
ccagggaagg gactagagtg gattgggcac atcaattaca atgggggcac cgactacaac  180
ccctccctca agagtcgagt caccatatca gtagacacgt ccaagaatca gttctccctg  240
aatttgaact ctgtgaccgc cgcagacacg gccgtgtatt actgtgcgag acagagattc  300
tacggtatgg acgtctgggg tccagggacc acggtcaccg tctcctca              348

SEQ ID NO: 130          moltype = AA  length = 116
FEATURE                 Location/Qualifiers
source                  1..116
                        mol_type = protein
                        organism = Homo sapiens
SEQUENCE: 130
QVQLQESGPG LVKSSETLSL TCTVSGGSIR NFYWSWLRQP PGKGLEWIGH INYNGGTDYN  60
PSLKSRVTIS VDTSKNQFSL NLNSVTAADT AVYYCARQRF YGMDVWGPGT TVTVSS      116

SEQ ID NO: 131          moltype = DNA  length = 24
FEATURE                 Location/Qualifiers
source                  1..24
                        mol_type = other DNA
                        organism = Homo sapiens
SEQUENCE: 131
ggtggctcca tcagaaattt ctac                                        24

SEQ ID NO: 132          moltype = AA  length = 8
FEATURE                 Location/Qualifiers
source                  1..8
                        mol_type = protein
                        organism = Homo sapiens
SEQUENCE: 132
GGSIRNFY                                                          8

SEQ ID NO: 133          moltype = DNA  length = 21
FEATURE                 Location/Qualifiers
source                  1..21
                        mol_type = other DNA
                        organism = Homo sapiens
SEQUENCE: 133
atcaattaca atgggggcac c                                           21

SEQ ID NO: 134          moltype = AA  length = 7
FEATURE                 Location/Qualifiers
source                  1..7
                        mol_type = protein
                        organism = Homo sapiens
SEQUENCE: 134
INYNGGT                                                           7

SEQ ID NO: 135          moltype = DNA  length = 30
FEATURE                 Location/Qualifiers
source                  1..30
                        mol_type = other DNA
```

```
                         organism = Homo sapiens
SEQUENCE: 135
gcgagacaga gattctacgg tatggacgtc                                          30

SEQ ID NO: 136           moltype = AA  length = 10
FEATURE                  Location/Qualifiers
source                   1..10
                         mol_type = protein
                         organism = Homo sapiens
SEQUENCE: 136
ARQRFYGMDV                                                                10

SEQ ID NO: 137           moltype = DNA  length = 324
FEATURE                  Location/Qualifiers
source                   1..324
                         mol_type = other DNA
                         organism = Homo sapiens
SEQUENCE: 137
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaagctcct gatctatgct gcatccagtt tgcaaagtgg ggtcccgtca  180
aggttcagtg gcagtggatc tgggacagat ttcactctca ccatcagcag tctgcaacct  240
gaagattttg caacttacta ctgtcaacag agttacagta cccctccgat caccttcggc  300
caagggacac gactggagat taaa                                         324

SEQ ID NO: 138           moltype = AA  length = 108
FEATURE                  Location/Qualifiers
source                   1..108
                         mol_type = protein
                         organism = Homo sapiens
SEQUENCE: 138
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPPITFG QGTRLEIK              108

SEQ ID NO: 139           moltype = DNA  length = 18
FEATURE                  Location/Qualifiers
source                   1..18
                         mol_type = other DNA
                         organism = Homo sapiens
SEQUENCE: 139
cagagcatta gcagctat                                                       18

SEQ ID NO: 140           moltype = AA  length = 6
FEATURE                  Location/Qualifiers
source                   1..6
                         mol_type = protein
                         organism = Homo sapiens
SEQUENCE: 140
QSISSY                                                                    6

SEQ ID NO: 141           moltype =   length =
SEQUENCE: 141
000

SEQ ID NO: 142           moltype =   length =
SEQUENCE: 142
000

SEQ ID NO: 143           moltype = DNA  length = 30
FEATURE                  Location/Qualifiers
source                   1..30
                         mol_type = other DNA
                         organism = Homo sapiens
SEQUENCE: 143
caacagagtt acagtacccc tccgatcacc                                          30

SEQ ID NO: 144           moltype = AA  length = 10
FEATURE                  Location/Qualifiers
source                   1..10
                         mol_type = protein
                         organism = Homo sapiens
SEQUENCE: 144
QQSYSTPPIT                                                                10

SEQ ID NO: 145           moltype = AA  length = 1408
FEATURE                  Location/Qualifiers
source                   1..1408
                         mol_type = protein
                         organism = Homo sapiens
```

```
SEQUENCE: 145
MKAPAVLAPG ILVLLFTLVQ RSNGECKEAL AKSEMNVNMK YQLPNFTAET PIQNVILHEH  60
HIFLGATNYI YVLNEEDLQK VAEYKTGPVL EHPDCFPCQD CSSKANLSGG VWKDNINMAL  120
VVDTYYDDQL ISCGSVNRGT CQRHVFPHNH TADIQSEVHC IFSPQIEEPS QCPDCVVSAL  180
GAKVLSSVKD RFINFFVGNT INSSYFPDHP LHSISVRRLK ETKDGFMFLT DQSYIDVLPE  240
FRDSYPIKYV HAFESNNFIY FLTVQRETLD AQTFHTRIIR FCSINSGLHS YMEMPLECIL  300
TEKRKKRSTK KEVFNILQAA YVSKPGAQLA RQIGASLNDD ILFGVFAQSK PDSAEPMDRS  360
AMCAFPIKYV NDFFNKIVNK NNVRCLQHFY GPNHEHCFNR TLLRNSSGCE ARRDEYRTEF  420
TTALQRVDLF MGQFSEVLLT SISTFIKGDL TIANLGTSEG RFMQVVVSRS GPSTPHVNFL  480
LDSHPVSPEV IVEHTLNQNG YTLVITGKKI TKIPLNGLGC RHFQSCSQCL SAPPFVQCGW  540
CHDKCVRSEE CLSGTWTQQI CLPAIYKVFP NSAPLEGGTR LTICGWDFGF RRNNKFDLKK  600
TRVLLGNESC TLTLSESTMN TLKCTVGPAM NKHFNMSIII SNGHGTTQYS TFSYVDPVIT  660
SISPKYGPMA GGTLLTLTGN YLNSGNSRHI SIGGKTCTLK SVSNSILECY TPAQTISTEF  720
AVKLKIDLAN RETSIFSYRE DPIVYEIHPT KSFISTWWKE PLNIVSFLFC FASGGSTITG  780
VGKNLNSVSV PRMVINVHEA GRNFTVACQH RSNSEIICCT TPSLQQLNLQ LPLKTKAFFM  840
LDGILSKYFD LIYVHNPVFK PFEKPVMISM GNENVLEIKG NDIDPEAVKG EVLKVGNKSC  900
ENIHLHSEAV LCTVPNDLLK LNSELNIEWK QAISSTVLGK VIVQPDQNFT GLIAGVVSIS  960
TALLLLLGFF LWLKKRKQIK DLGSELVRYD ARVHTPHLDR LVSARSVSPT TEMVSNESVD  1020
YRATFPEDQF PNSSQNGSCR QVQYPLTDMS PILTSGDSDI SSPLLQNTVH IDLSALNPEL  1080
VQAVQHVVIG PSSLIVHFNE VIGRGHFGCV YHGTLLDNDG KKIHCAVKSL NRITDIGEVS  1140
QFLTEGIIMK DFSHPNVLSL LGICLRSEGS PLVVLPYMKH GDLRNFIRNE THNPTVKDLI  1200
GFGLQVAKGM KYLASKKFVH RDLAARNCML DEKFTVKVAD FGLARDMYDK EYYSVHNKTG  1260
AKLPVKWMAL ESLQTQKFTT KSDVWSFGVL LWELMTRGAP PYPDVNTFDI TVYLLQGRRL  1320
LQPEYCPDPL YEVMLKCWHP KAEMRPSFSE LVSRISAIFS TFIGEHYVHV NATYVNVKCV  1380
APYPSLLSSE DNADDEVDTR PASFWETS                                    1408

SEQ ID NO: 146          moltype = AA  length = 1390
FEATURE                 Location/Qualifiers
source                  1..1390
                        mol_type = protein
                        organism = Homo sapiens
SEQUENCE: 146
MKAPAVLAPG ILVLLFTLVQ RSNGECKEAL AKSEMNVNMK YQLPNFTAET PIQNVILHEH  60
HIFLGATNYI YVLNEEDLQK VAEYKTGPVL EHPDCFPCQD CSSKANLSGG VWKDNINMAL  120
VVDTYYDDQL ISCGSVNRGT CQRHVFPHNH TADIQSEVHC IFSPQIEEPS QCPDCVVSAL  180
GAKVLSSVKD RFINFFVGNT INSSYFPDHP LHSISVRRLK ETKDGFMFLT DQSYIDVLPE  240
FRDSYPIKYV HAFESNNFIY FLTVQRETLD AQTFHTRIIR FCSINSGLHS YMEMPLECIL  300
TEKRKKRSTK KEVFNILQAA YVSKPGAQLA RQIGASLNDD ILFGVFAQSK PDSAEPMDRS  360
AMCAFPIKYV NDFFNKIVNK NNVRCLQHFY GPNHEHCFNR TLLRNSSGCE ARRDEYRTEF  420
TTALQRVDLF MGQFSEVLLT SISTFIKGDL TIANLGTSEG RFMQVVVSRS GPSTPHVNFL  480
LDSHPVSPEV IVEHTLNQNG YTLVITGKKI TKIPLNGLGC RHFQSCSQCL SAPPFVQCGW  540
CHDKCVRSEE CLSGTWTQQI CLPAIYKVFP NSAPLEGGTR LTICGWDFGF RRNNKFDLKK  600
TRVLLGNESC TLTLSESTMN TLKCTVGPAM NKHFNMSIII SNGHGTTQYS TFSYVDPVIT  660
SISPKYGPMA GGTLLTLTGN YLNSGNSRHI SIGGKTCTLK SVSNSILECY TPAQTISTEF  720
AVKLKIDLAN RETSIFSYRE DPIVYEIHPT KSFISGGSTI TGVGKNLNSV SVPRMVINVH  780
EAGRNFTVAC QHRSNSEIIC CTTPSLQQLN LQLPLKTKAF FMLDGILSKY FDLIYVHNPV  840
FKPFEKPVMI SMGNENVLEI KGNDIDPEAV KGEVLKVGNK SCENIHLHSE AVLCTVPNDL  900
LKLNSELNIE WKQAISSTVL GKVIVQPDQN FTGLIAGVVS ISTALLLLLG FFLWLKKRKQ  960
IKDLGSELVR YDARVHTPHL DRLVSARSVS PTTEMVSNES VDYRATFPED QFPNSSQNGS  1020
CRQVQYPLTD MSPILTSGDS DISSPLLQNT VHIDLSALNP ELVQAVQHVV IGPSSLIVHF  1080
NEVIGRGHFG CVYHGTLLDN DGKKIHCAVK SLNRITDIGE VSQFLTEGII MKDFSHPNVL  1140
SLLGICLRSE GSPLVVLPYM KHGDLRNFIR NETHNPTVKD LIGFGLQVAK GMKYLASKKF  1200
VHRDLAARNC MLDEKFTVKV ADFGLARDMY DKEYYSVHNK TGAKLPVKWM ALESLQTQKF  1260
TTKSDVWSFG VLLWELMTRG APPYPDVNTF DITVYLLQGR RLLQPEYCPD PLYEVMLKCW  1320
HPKAEMRPSF SELVSRISAI FSTFIGEHYV HVNATYVNVK CVAPYPSLLS SEDNADDEVD  1380
TRPASFWETS                                                        1390

SEQ ID NO: 147          moltype = AA  length = 934
FEATURE                 Location/Qualifiers
source                  1..934
                        mol_type = protein
                        organism = Homo sapiens
SEQUENCE: 147
MKAPAVLAPG ILVLLFTLVQ RSNGECKEAL AKSEMNVNMK YQLPNFTAET PIQNVILHEH  60
HIFLGATNYI YVLNEEDLQK VAEYKTGPVL EHPDCFPCQD CSSKANLSGG VWKDNINMAL  120
VVDTYYDDQL ISCGSVNRGT CQRHVFPHNH TADIQSEVHC IFSPQIEEPS QCPDCVVSAL  180
GAKVLSSVKD RFINFFVGNT INSSYFPDHP LHSISVRRLK ETKDGFMFLT DQSYIDVLPE  240
FRDSYPIKYV HAFESNNFIY FLTVQRETLD AQTFHTRIIR FCSINSGLHS YMEMPLECIL  300
TEKRKKRSTK KEVFNILQAA YVSKPGAQLA RQIGASLNDD ILFGVFAQSK PDSAEPMDRS  360
AMCAFPIKYV NDFFNKIVNK NNVRCLQHFY GPNHEHCFNR TLLRNSSGCE ARRDEYRTEF  420
TTALQRVDLF MGQFSEVLLT SISTFIKGDL TIANLGTSEG RFMQVVVSRS GPSTPHVNFL  480
LDSHPVSPEV IVEHTLNQNG YTLVITGKKI TKIPLNGLGC RHFQSCSQCL SAPPFVQCGW  540
CHDKCVRSEE CLSGTWTQQI CLPAIYKVFP NSAPLEGGTR LTICGWDFGF RRNNKFDLKK  600
TRVLLGNESC TLTLSESTMN TLKCTVGPAM NKHFNMSIII SNGHGTTQYS TFSYVDPVIT  660
SISPKYGPMA GGTLLTLTGN YLNSGNSRHI SIGGKTCTLK SVSNSILECY TPAQTISTEF  720
AVKLKIDLAN RETSIFSYRE DPIVYEIHPT KSFISGGSTI TGVGKNLNSV SVPRMVINVH  780
EAGRNFTVAC QHRSNSEIIC CTTPSLQQLN LQLPLKTKAF FMLDGILSKY FDLIYVHNPV  840
FKPFEKPVMI SMGNENVLEI KGNDIDPEAV KGEVLKVGNK SCENIHLHSE AVLCTVPNDL  900
LKLNSELNIE VGFLHSSHDV NKEASVIMLF SGLK                              934
```

-continued

```
SEQ ID NO: 148         moltype = AA  length = 281
FEATURE                Location/Qualifiers
source                 1..281
                       mol_type = protein
                       organism = Homo sapiens
SEQUENCE: 148
KEALAKSEMN VNMKYQLPNF TAETPIQNVI LHEHHIFLGA TNYIYVLNEE DLQKVAEYKT  60
GPVLEHPDCF PCQDCSSKAN LSGGVWKDNI NMALVVDTYY DDQLISCGSV NRGTCQRHVF  120
PHNHTADIQS EVHCIFSPQI EEPSQCPDCV VSALGAKVLS SVKDRFINFF VGNTINSSYF  180
PDHPLHSISV RRLKETKDGF MFLTDQSYID VLPEFRDSYP IKYVHAFESN NFIYFLTVQR  240
ETLDAQTFHT RIIRFCSINS GLHSYMEMPL ECILTEKRKK R                    281

SEQ ID NO: 149         moltype = AA  length = 1101
FEATURE                Location/Qualifiers
source                 1..1101
                       mol_type = protein
                       organism = Homo sapiens
SEQUENCE: 149
STKKEVFNIL QAAYVSKPGA QLARQIGASL NDDILFGVFA QSKPDSAEPM DRSAMCAFPI  60
KYVNDFFNKI VNKNNVRCLQ HFYGPNHEHC FNRTLLRNSS GCEARRDEYR TEFTTALQRV  120
DLFMGQFSEV LLTSISTFIK GDLTIANLGT SEGRFMQVVV SRSGPSTPHV NFLLDSHPVS  180
PEVIVEHTLN QNGYTLVITG KKITKIPLNG LGCRHFQSCS QCLSAPPFVQ CGWCHDKCVR  240
SEECLSGTWT QQICLPAIYK VFPNSAPLEG GTRLTICGWD FGFRRNNKFD LKKTRVLLGN  300
ESCTLTLSES TMNTLKCTVG PAMNKHFNMS IIISNGHGTT QYSTFSYVDP VITSISPKYG  360
PMAGGTLLTL TGNYLNSGNS RHISIGGKTC TLKSVSNSIL ECYTPAQTIS TEFAVKLKID  420
LANRETSIFS YREDPIVYEI HPTKSFISTW WKEPLNIVSF LFCFASGGST ITGVGKNLNS  480
VSVPRMVINV HEAGRNFTVA CQHRSNSEII CCTTPSLQQL NLQLPLKTKA FFMLDGILSK  540
YFDLIYVHNP VFKPFEKPVM ISMGNENVLE IKGNDIDPEA VKGEVLKVGN KSCENIHLHS  600
EAVLCTVPND LLKLNSELNI EWKQAISSTV LGKVIVQPDQ NFTGLIAGVV SISTALLLLL  660
GFFLWLKKRK QIKDLGSELV RYDARVHTPH LDRLVSARSV SPTTEMVSNE SVDYRATFPE  720
DQFPNSSQNG SCRQVQYPLT DMSPILTSGD SDISSPLLQN TVHIDLSALN PELVQAVQHV  780
VIGPSSLIVH FNEVIGRGHF GCVYHGTLLD NDGKKIHCAV KSLNRITDIG EVSQFLTEGI  840
IMKDFSHPNV LSLLGICLRS EGSPLVVLPY MKHGDLRNFI RNETHNPTVK DLIGFGLQVA  900
KGMKYLASKK FVHRDLAARN CMLDEKFTVK VADFGLARDM YDKEYYSVHN KTGAKLPVKW  960
MALESLQTQK FTTKSDVWSF GVLLWELMTR GAPPYPDVNT FDITVYLLQG RRLLQPEYCP  1020
DPLYEVMLKC WHPKAEMRPS FSELVSRISA IFSTFIGEHY VHVNATYVNV KCVAPYPSLL  1080
SSEDNADDEV DTRPASFWET S                                          1101

SEQ ID NO: 150         moltype = AA  length = 1082
FEATURE                Location/Qualifiers
source                 1..1082
                       mol_type = protein
                       organism = Homo sapiens
SEQUENCE: 150
TKKEVFNILQ AAYVSKPGAQ LARQIGASLN DDILFGVFAQ SKPDSAEPMD RSAMCAFPIK  60
YVNDFFNKIV NKNNVRCLQH FYGPNHEHCF NRTLLRNSSG CEARRDEYRT EFTTALQRVD  120
LFMGQFSEVL LTSISTFIKG DLTIANLGTS EGRFMQVVVS RSGPSTPHVN FLLDSHPVSP  180
EVIVEHTLNQ NGYTLVITGK KITKIPLNGL GCRHFQSCSQ CLSAPPFVQC GWCHDKCVRS  240
EECLSGTWTQ QICLPAIYKV FPNSAPLEGG TRLTICGWDF GFRRNNKFDL KKTRVLLGNE  300
SCTLTLSEST MNTLKCTVGP AMNKHFNMSI IISNGHGTTQ YSTFSYVDPV ITSISPKYGP  360
MAGGTLLTLT GNYLNSGNSR HISIGGKTCT LKSVSNSILE CYTPAQTIST EFAVKLKIDL  420
ANRETSIFSY REDPIVYEIH PTKSFISGGS TITGVGKNLN SVSVPRMVIN VHEAGRNFTV  480
ACQHRSNSEI ICCTTPSLQQ LNLQLPLKTK AFFMLDGILS KYFDLIYVHN PVFKPFEKPV  540
MISMGNENVL EIKGNDIDPE AVKGEVLKVG NKSCENIHLH SEAVLCTVPN DLLKLNSELN  600
IEWKQAISST VLGKVIVQPD QNFTGLIAGV VSISTALLLL LGFFLWLKKR KQIKDLGSEL  660
VRYDARVHTP HLDRLVSARS VSPTTEMVSN ESVDYRATFP EDQFPNSSQN GSCRQVQYPL  720
TDMSPILTSG DSDISSPLLQ NTVHIDLSAL NPELVQAVQH VVIGPSSLIV HFNEVIGRGH  780
FGCVYHGTLL DNDGKKIHCA VKSLNRITDI GEVSQFLTEG IIMKDFSHPN VLSLLGICLR  840
SEGSPLVVLP YMKHGDLRNF IRNETHNPTV KDLIGFGLQV AKGMKYLASK KFVHRDLAAR  900
NCMLDEKFTV KVADFGLARD MYDKEYYSVH NKTGAKLPVK WMALESLQTQ KFTTKSDVWS  960
FGVLLWELMT RGAPPYPDVN TFDITVYLLQ GRRLLQPEYC PDPLYEVMLK CWHPKAEMRP  1020
SFSELVSRIS AIFSTFIGEH YVHVNATYVN VKCVAPYPSL LSSEDNADDE VDTRPASFWE  1080
TS                                                               1082

SEQ ID NO: 151         moltype = AA  length = 626
FEATURE                Location/Qualifiers
source                 1..626
                       mol_type = protein
                       organism = Homo sapiens
SEQUENCE: 151
TKKEVFNILQ AAYVSKPGAQ LARQIGASLN DDILFGVFAQ SKPDSAEPMD RSAMCAFPIK  60
YVNDFFNKIV NKNNVRCLQH FYGPNHEHCF NRTLLRNSSG CEARRDEYRT EFTTALQRVD  120
LFMGQFSEVL LTSISTFIKG DLTIANLGTS EGRFMQVVVS RSGPSTPHVN FLLDSHPVSP  180
EVIVEHTLNQ NGYTLVITGK KITKIPLNGL GCRHFQSCSQ CLSAPPFVQC GWCHDKCVRS  240
EECLSGTWTQ QICLPAIYKV FPNSAPLEGG TRLTICGWDF GFRRNNKFDL KKTRVLLGNE  300
SCTLTLSEST MNTLKCTVGP AMNKHFNMSI IISNGHGTTQ YSTFSYVDPV ITSISPKYGP  360
MAGGTLLTLT GNYLNSGNSR HISIGGKTCT LKSVSNSILE CYTPAQTIST EFAVKLKIDL  420
ANRETSIFSY REDPIVYEIH PTKSFISGGS TITGVGKNLN SVSVPRMVIN VHEAGRNFTV  480
```

-continued

```
ACQHRSNSEI ICCTTPSLQQ LNLQLPLKTK AFFMLDGILS KYFDLIYVHN PVFKPFEKPV  540
MISMGNENVL EIKGNDIDPE AVKGEVLKVG NKSCENIHLH SEAVLCTVPN DLLKLNSELN  600
IEVGFLHSSH DVNKEASVIM LFSGLK                                        626

SEQ ID NO: 152          moltype = AA  length = 650
FEATURE                 Location/Qualifiers
REGION                  1..650
                        note = synthetic
source                  1..650
                        mol_type = protein
                        organism = synthetic construct
SEQUENCE: 152
TKKEVFNILQ AAYVSKPGAQ LARQIGASLN DDILFGVFAQ SKPDSAEPMD RSAMCAFPIK  60
YVNDFFNKIV NKNNVRCLQH FYGPNHEHCF NRTLLRNSSG CEARRDEYRT EFTTALQRVD  120
LFMGQFSEVL LTSISTFIKG DLTIANLGTS EGRFMQVVVS RSGPSTPHVN FLLDSHPVSP  180
EVIVEHTLNQ NGYTLVITGK KITKIPLNGL GCRHFQSCSQ CLSAPPFVQC GWCHDKCVRS  240
EECLSGTWTQ QICLPAIYKV FPNSAPLEGG TRLTICGWDF GFRRNNKFDL KKTRVLLGNE  300
SCTLTLSEST MNTLKCTVGP AMNKHFNMSI IISNGHGTTQ YSTFSYVDPV ITSISPKYGP  360
MAGGTLLTLT GNYLNSGNSR HISIGGKTCT LKSVSNSILE CYTPAQTIST EFAVKLKIDL  420
ANRETSIFSY REDPIVYEIH PTKSFISTWW KEPLNIVSFL FCFASGGSTI TGVGKNLNSV  480
SVPRMVINVH EAGRNFTVAC QHRSNSEIIC CTTPSLQQLN LQLPLKTKAF FMLDGILSKY  540
FDLIYVHNPV FKPFEKPVMI SMGNENVLEI KGNDIDPEAV KGEVLKVGNK SCENIHLHSE  600
AVLCTVPNDL LKLNSELNIE WKQAEQKLIS EEDLEQKLIS EEDLHHHHHH              650

SEQ ID NO: 153          moltype = AA  length = 838
FEATURE                 Location/Qualifiers
REGION                  1..838
                        note = synthetic
source                  1..838
                        mol_type = protein
                        organism = synthetic construct
SEQUENCE: 153
TKKEVFNILQ AAYVSKPGAQ LARQIGASLN DDILFGVFAQ SKPDSAEPMD RSAMCAFPIK  60
YVNDFFNKIV NKNNVRCLQH FYGPNHEHCF NRTLLRNSSG CEARRDEYRT EFTTALQRVD  120
LFMGQFSEVL LTSISTFIKG DLTIANLGTS EGRFMQVVVS RSGPSTPHVN FLLDSHPVSP  180
EVIVEHTLNQ NGYTLVITGK KITKIPLNGL GCRHFQSCSQ CLSAPPFVQC GWCHDKCVRS  240
EECLSGTWTQ QICLPAIYKV FPNSAPLEGG TRLTICGWDF GFRRNNKFDL KKTRVLLGNE  300
SCTLTLSEST MNTLKCTVGP AMNKHFNMSI IISNGHGTTQ YSTFSYVDPV ITSISPKYGP  360
MAGGTLLTLT GNYLNSGNSR HISIGGKTCT LKSVSNSILE CYTPAQTIST EFAVKLKIDL  420
ANRETSIFSY REDPIVYEIH PTKSFISTWW KEPLNIVSFL FCFASGGSTI TGVGKNLNSV  480
SVPRMVINVH EAGRNFTVAC QHRSNSEIIC CTTPSLQQLN LQLPLKTKAF FMLDGILSKY  540
FDLIYVHNPV FKPFEKPVMI SMGNENVLEI KGNDIDPEAV KGEVLKVGNK SCENIHLHSE  600
AVLCTVPNDL LKLNSELNIE WKQAMEVSSV FIFPPKPKDV LTITLTPKVT CVVVDISKDD  660
PEVQFSWFVD DVEVHTAQTQ PREEQFNSTF RSVSELPIMH QDWLNGKEFK CRVNSAAFPA  720
PIEKTISKTK GRPKAPQVYT IPPPKEQMAK DKVSLTCMIT DFFPEDITVE WQWNGQPAEN  780
YKNTQPIMDT DGSYFVYSKL NVQKSNWEAG NTFTCSVLHE GLHNHHTEKS LSHSPGKE    838

SEQ ID NO: 154          moltype = AA  length = 1100
FEATURE                 Location/Qualifiers
REGION                  1..1100
                        note = synthetic
source                  1..1100
                        mol_type = protein
                        organism = synthetic construct
SEQUENCE: 154
STKKEVFNIL QAAYVSKPGA QLARQIGASL NDDILFGVFA QSKPDSAEPM DRSAMCAFPI  60
KYVNDFFNKI VNKNNVRCLQ HFYGPNHEHC FNRTLLRNSS GCEARRDEYR AEFTTALQRV  120
DLFMGQFSEV LLTSISTFVK GDLTIANLGT SEGRFMQVVV SRSGPSTPHV NFLLDSHPVS  180
PEVIVEHPLN QNGYTLVVTG KKITKIPLNG LGCRHFQSCS QCLSAPPFVQ CGWCHDKCVR  240
SEECPSGTWT QQICLPAIYK VFPTSAPLEG GTRLTICGWD FGFRRNNKFD LKKTRVLLGN  300
ESCTLTLSES TMNTLKCTVG PAMNKHFNMS IIISNGHGTT QYSTFSYVDP IITSISPKYG  360
PMAGGTLLTL TGNYLNSGNS RHISIGGKTC TLKSVSNSIL ECYTPAQTIS TEFAVKLKID  420
LANRETSIFS YREDPIVYEI HPTKSFISGG STITGVGKNL HSVSVPRMVI NVHEAGRNFT  480
VACQHRSNSE IICCTTPSLQ QLNLQLPLKT KAFFMLDGIL SKYFDLIYVH NPVFKPFEKP  540
VMISMGNENV LEIKGNDIDP EAVKGEVLKV GNKSCENIHL HSEAVLCTVP NDLLKLNSEL  600
NIEWKQAISS TVLGKVIVQP DQNFTGLIAG VVSISIALLL LLGLFLWLKK RKQIKDLGSE  660
LVRYDARVHT PHLDRLVSAR SVSPTTEMVS NESVDYRATF PEDQFPNSSQ NGSCRQVQYP  720
LTDMSPILTS GDSDISSPLL QNTVHIDLSA LNPELVQAVQ HVVIGPSSLI VHFNEVIGRG  780
HFGCVYHGTL LDNDGKKIHC AVKSLNRITD IGEVSQFLTE GIIMKDFSHP NVLSLLGICL  840
RSEGSPLVVL PYMKHGDLRN FIRNETHNPT VKDLIGFGLQ VAKGMKYLAS KKFVHRDLAA  900
RNCMLDEKFT VKVADFGLAR DMYDKEYYSV HNKTGAKLPV KWMALESLQT QKFTTKSDVW  960
SFGVLLWELM TRGAPPYPDV NTFDITVYLL QGRRLLQPEY CPDPLYEVML KCWHPKAEMR  1020
PSFSELVSRI SAIFSTFIGE HYVHVNATYV NVKCVAPYPS LLSSEDNADD EVDTEQKLIS  1080
EEDLEQKLIS EEDLHHHHHH                                               1100

SEQ ID NO: 155          moltype = AA  length = 936
FEATURE                 Location/Qualifiers
REGION                  1..936
                        note = synthetic
```

-continued

```
source                  1..936
                        mol_type = protein
                        organism = synthetic construct
SEQUENCE: 155
ECKEALAKSE MNVNMKYQLP NFTAETPIQN VILHEHHIFL GATNYIYVLN EEDLQKVAEY  60
KTGPVLEHPD CFPCQDCSSK ANLSGGVWKD NINMALVVDT YYDDQLISCG SVNRGTCQRH  120
VFPHNHTADI QSEVHCIFSP QIEEPSQCPD CVVSALGAKV LSSVKDRFIN FFVGNTINSS  180
YFPDHPLHSI SVRRLKETKD GFMFLTDQSY IDVLPEFRDS YPIKYVHAFE SNNFIYFLTV  240
QRETLDAQTF HTRIIRFCSI NSGLHSYMEM PLECILTEKR KKRSTKKEVF NILQAAYVSK  300
PGAQLARQIG ASLNDDILFG VFAQSKPDSA EPMDRSAMCA FPIKYVNDFF NKIVNKNNVR  360
CLQHFYGPNH EHCFNRTLLR NSSGCEARRD EYRTEFTTAL QRVDLFMGQF SEVLLTSIST  420
FIKGDLTIAN LGTSEGRFMQ VVVSRSGPST PHVNFLLDSH PVSPEVIVEH TLNQNGYTLV  480
ITGKKITKIP LNGLGCRHFQ SCSQCLSAPP FVQCGWCHDK CVRSEECLSG TWTQQICLPA  540
IYKVFPNSAP LEGGTRLTIC GWDFGFRRNN KFDLKKTRVL LGNESCTLTL SESTMNTLKC  600
TVGPAMNKHF NMSIIISNGH GTTQYSTFSY VDPVITSISP KYGPMAGGTL LTLTGNYLNS  660
GNSRHISIGG KTCTLKSVSN SILECYTPAQ TISTEFAVKL KIDLANRETS IFSYREDPIV  720
YEIHPTKSFI SGGSTITGVG KNLNSVSVPR MVINVHEAGR NFTVACQHRS NSEIICCTTP  780
SLQQLNLQLP LKTKAFFMLD GILSKYFDLI YVHNPVFKPF EKPVMISMGN ENVLEIKGND  840
IDPEAVKGEV LKVGNKSCEN IHLHSEAVLC TVPNDLLKLN SELNIEWKQA ISSTVLGKVI  900
VQPDQNFTEQ KLISEEDLGG EQKLISEEDL HHHHHH                            936

SEQ ID NO: 156          moltype = AA  length = 12
FEATURE                 Location/Qualifiers
REGION                  1..12
                        note = synthetic
source                  1..12
                        mol_type = protein
                        organism = synthetic construct
SEQUENCE: 156
VRRLKETKDG FM                                                      12

SEQ ID NO: 157          moltype = AA  length = 11
FEATURE                 Location/Qualifiers
REGION                  1..11
                        note = synthetic
source                  1..11
                        mol_type = protein
                        organism = synthetic construct
SEQUENCE: 157
LARQIGASLN D                                                       11

SEQ ID NO: 158          moltype = AA  length = 35
FEATURE                 Location/Qualifiers
REGION                  1..35
                        note = synthetic
source                  1..35
                        mol_type = protein
                        organism = synthetic construct
SEQUENCE: 158
FIKGDLTIAN LGTSEGRFMQ VVVSRSGPST PHVNF                             35
```

METHODS FOR MAKING RADIOLABELED ANTI-MET BINDING PROTEINS

RELATED APPLICATIONS

This application is a continuation of U.S. patent application Ser. No. 17/021,497, filed Sep. 15, 2020, now U.S. Pat. No. 11,896,682, issued Feb. 13, 2024, which claims priority under 35 U.S.C. 119 (e) to U.S. Provisional Patent Application Ser. No. 62/901,003, entitled "RADIOLABELED MET BINDING PROTEINS FOR IMMUNO-PET IMAGING", filed Sep. 16, 2019, the entire contents of each of which are hereby incorporated by reference herein.

FIELD

This disclosure relates to radiolabeled MET binding proteins and their use in immuno-PET imaging.

SEQUENCE LISTING

A copy of the sequence listing is submitted concurrently with the specification electronically via Patent Center. The content of the electronic sequence listing (10649US02_Sequence_Listing_ST26.xml; Size: 159,744 bytes; and Date of Creation: Dec. 29, 2023) is herein incorporated by reference in its entirety.

BACKGROUND

Hepatocyte growth factor (HGF) (a.k.a. scatter factor [SF]) is a heterodimeric paracrine growth factor that exerts its activity by interacting with the HGF receptor (HGFR). HGFR is the product of the c-Met oncogene and is also known as MET. MET is a receptor tyrosine kinase consisting of a transmembrane beta chain linked via a disulfide bridge to an extracellular alpha chain. The binding of HGF to MET activates the kinase catalytic activity of MET resulting in the phosphorylation of Tyr 1234 and Tyr 1235 of the beta chain and subsequent activation of downstream signaling pathways.

MET and/or HGF overexpression, activation, or amplification has been shown to be involved in non-small cell lung carcinoma (NSCLC), gastric, ovarian, pancreatic, thyroid, breast, head and neck, colon and kidney carcinomas (Sierra and Tsao, Ther. Adv. Med. Oncol., 3(1 Suppl): S21-S35, 2011). MET amplification is thought to be a key driver of oncogenesis in NSCLCs and oesophagogastric malignancies. In addition, mutations resulting in exon 14 deletion of MET have been described as oncogenic drivers in a subset of NSCLC. Tumor cell lines having MET gene amplification are highly dependent on MET for growth and survival. Preclinical data implicate MET signaling in resistance to targeted therapies in multiple tumor types, such as NSCLC, colorectal cancer, and head and neck squamous-cell carcinoma (HNSCC).

Immuno-positron emission tomography (PET) is a diagnostic imaging tool that utilizes monoclonal antibodies labeled with positron emitters, combining the targeting properties of an antibody with the sensitivity of positron emission tomography cameras. See, e.g., *The Oncologist,* 12: 1379 (2007); *Journal of Nuclear Medicine,* 52(8): 1171 (2011). Immuno-PET enables the visualization and quantification of antigen and antibody accumulation in vivo and, as such, can serve as an important tool for diagnostics and complementing therapy. For example, immuno-PET can aid in the selection of potential candidates for a particular therapy, as well as in the monitoring of treatment.

Both preclinical and recent clinical results indicate that tumors harboring MET genetic alterations respond to MET inhibitors, validating MET as a cancer driver. As such, there is need for diagnostic tools for anti-MET and/or anti-MET therapy, including, inter alia, diagnostic tools that enable the detection of suitable candidates for said therapy.

BRIEF SUMMARY

Included in this disclosure are radiolabeled anti-MET antibody conjugates and MET×MET bispecific antibody conjugates for use in immuno-PET imaging.

In one aspect, the conjugate comprises an anti-MET antibody, a MET×MET bispecific antibody, or an antigen-binding fragment thereof, a chelating moiety, and a positron emitter.

Provided herein are also processes for synthesizing said conjugates and synthetic intermediates useful for the same.

Provided herein are also methods of imaging a tissue that expresses MET, the methods comprising administering a radiolabeled anti-MET antibody conjugate or MET×MET bispecific antibody conjugate described herein to the tissue; and visualizing the MET expression by positron emission tomography (PET) imaging.

Provided herein are also methods for detecting MET in a tissue, the methods comprising administering a radiolabeled anti-MET antibody conjugate or MET×MET bispecific antibody conjugate described herein to the tissue; and visualizing the MET expression by PET imaging. In one embodiment, the tissue is present in a human subject. In certain embodiments, the subject is a non-human mammal. In certain embodiments, the subject has a disease or disorder such as cancer.

Provided herein are also methods for determining the presence of MET expressing cells in a subject. The methods comprise administering a radiolabeled anti-MET antibody conjugate or MET×MET bispecific antibody conjugate described herein to the subject and visualizing MET expression by PET imaging.

Provided herein are also methods for identifying a subject having a solid tumor to be suitable for anti-tumor therapy comprising an inhibitor of the HGF/MET signaling pathway, for example, an anti-MET antibody, a MET×MET bispecific antibody, or an antibody drug conjugate (ADC) thereof. The methods comprise administering a radiolabeled antibody conjugate described herein to the subject, and visualizing the administered radiolabeled antibody conjugate in the tumor by PET imaging wherein presence of the radiolabeled antibody conjugate in the tumor identifies the subject as suitable for anti-tumor therapy comprising an inhibitor of the HGF/MET signaling pathway.

Provided herein are also methods of treating a solid tumor in a subject, the methods comprising determining that the solid tumor is MET-positive; and administering an anti-tumor therapy to the subject in need thereof. In certain embodiments, the anti-tumor therapy comprises an anti-MET antibody or a MET×MET bispecific antibody. In certain embodiments, the subject is administered a radiolabeled antibody conjugate described herein, and localization of the radiolabeled antibody conjugate is imaged via positron emission tomography (PET) imaging to determine if the tumor is MET-positive.

Provided herein are also methods for monitoring the efficacy of an anti-tumor therapy in a subject being treated with an anti-tumor therapy, wherein the methods comprise administering a radiolabeled conjugate described herein to the subject; imaging the localization of the administered radiolabeled conjugate in the tumor by PET imaging; and determining tumor growth, wherein a decrease from the baseline in uptake of the conjugate or radiolabeled signal indicates tumor regression and efficacy of the anti-tumor therapy. In certain embodiments, the anti-tumor therapy comprises an inhibitor of the HGF/MET signaling pathway (e.g., an anti-MET antibody or a MET×MET bispecific antibody, or an ADC of either).

Provided herein are also methods for predicting response of a subject to an anti-tumor therapy comprising an inhibitor of the HGF/MET signaling pathway, the methods comprising determining if the tumor is MET-positive, wherein if the tumor is MET-positive it indicates a positive response of the subject to an anti-tumor therapy comprising an inhibitor of the HGF/MET signaling pathway. In certain embodiments, the tumor is determined positive by administering a radiolabeled antibody conjugate of the present disclosure and localizing the radiolabeled antibody conjugate in the tumor by PET imaging wherein presence of the radiolabeled antibody conjugate in the tumor indicates that the tumor is MET-positive.

Provided herein are methods for diagnosing and treating a subject with a tumor, the methods comprising administering a radiolabeled conjugate described herein to the subject wherein localization of the radiolabeled antibody conjugate is imaged via PET imaging to determine if the tumor is MET-positive; diagnosing the subject with a MET-positive tumor; and administering to the subject an anti-tumor therapy comprising an inhibitor of the HGF/MET signaling pathway.

Provided herein are methods for diagnosing a subject having a MET expressing tumor, the methods comprising administering a radiolabeled anti-MET antibody conjugate or MET×MET bispecific antibody conjugate described herein to the subject; visualizing MET expression by PET imaging; and diagnosing the subject with a MET expressing tumor when MET expression is visualized by PET imaging.

DETAILED DESCRIPTION

I. Definitions

Figure 1:
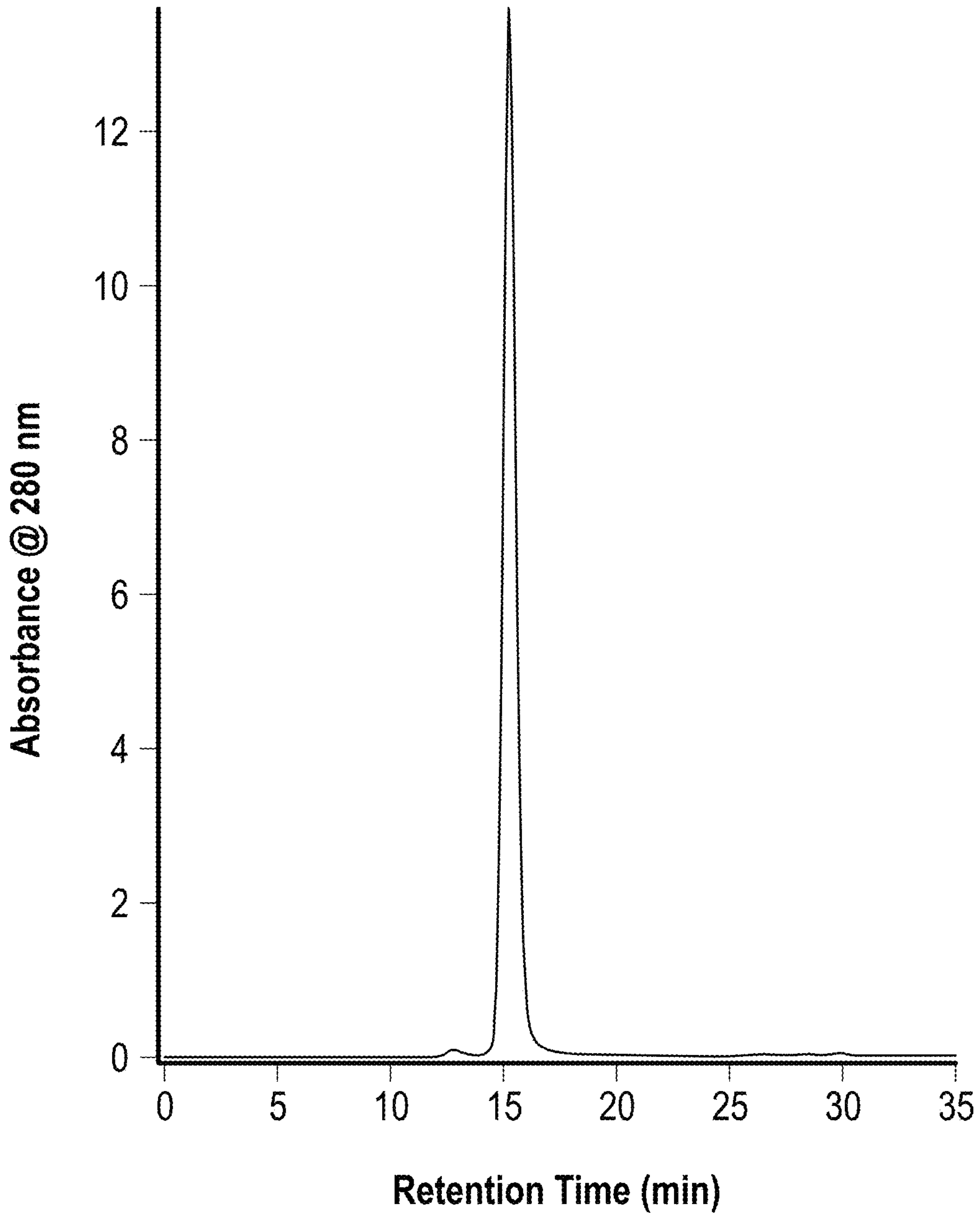
FIG. 1 depicts an SE-HPLC chromatogram of a 5 ug injection of DFO-MET×MET immunoconjugate conjugate on Superdex 200 Increase column with UV 280 nm absorbance detection. Monomeric (99.6%) and high molecular weight (HMW) species (0.4%) are indicated.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise herein, all technical and scientific terms used herein have the same meaning as commonly understood by one of ordinary skill in the art to which the disclosed subject matter belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

MET Protein

The expressions "MET," "c-Met," and the like, as used herein, refer to the human membrane spanning receptor tyrosine kinase comprising (1) the amino acid sequence as set forth in SEQ ID NO:145, and/or having the amino acid sequence as set forth in NCBI accession No. NM_001127500.2, representing the unprocessed preproprotein of isoform "a", (2) the amino acid sequence as set forth in SEQ ID NO:146, and/or having the amino acid sequence as set forth in NCBI accession No. NM_000236.2, representing the unprocessed preproprotein of isoform "b", (3) the amino acid sequence as set forth in SEQ ID NO:147, and/or having the amino acid sequence as set forth in NCBI accession No. NM_001311330.1, representing the unprocessed preproprotein of isoform "c", and/or (3) the mature protein comprising the cytoplasmic alpha subunit (SEQ ID NO:148) shared by all three isoforms and the transmembrane beta subunit (SEQ ID NO:149, 150, or 151 of isoform a, b and c, respectively). The expression "MET" includes both monomeric and multimeric MET molecules. As used herein, the expression "monomeric human MET" means a MET protein or portion thereof that does not contain or possess any multimerizing domains and that exists under normal conditions as a single MET molecule without a direct physical connection to another MET molecule. An exemplary monomeric MET molecule is the molecule referred to herein as "hMET.mmh" comprising the amino acid sequence of SEQ ID NO:152 (see, e.g., Example 3 of US-2018-0134794). As used herein, the expression "dimeric human MET" means a construct comprising two MET molecules connected to one another through a linker, covalent bond, non-covalent bond, or through a multimerizing domain such as an antibody Fc domain. An exemplary dimeric MET molecule is the molecule referred to herein as "hMET.mFc" comprising the amino acid sequence of SEQ ID NO:153 (see, e.g., Example 3 of US-2018-0134794).

All references to proteins, polypeptides and protein fragments herein are intended to refer to the human version of the respective protein, polypeptide or protein fragment unless explicitly specified as being from a non-human species. Thus, the expression "MET" means human MET unless specified as being from a non-human species, e.g., "mouse MET," "monkey MET," etc.

As used herein, the expression "cell surface-expressed MET" means one or more MET protein(s), or the extracellular domain thereof, that is/are expressed on the surface of a cell in vitro or in vivo, such that at least a portion of a MET protein is exposed to the extracellular side of the cell membrane and is accessible to an antigen-binding portion of an antibody. A "cell surface-expressed MET" can comprise or consist of a MET protein expressed on the surface of a cell which normally expresses MET protein. Alternatively, "cell surface-expressed MET" can comprise or consist of MET protein expressed on the surface of a cell that normally does not express human MET on its surface but has been artificially engineered to express MET on its surface.

Other Definitions

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments, the FRs of the antibody (or antigen binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The human anti-MET antibodies or MET×MET bispecific antibodies useful herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences of Table 1 to germline sequences available from, for example, public antibody sequence databases. Useful according to the present disclosure are antibodies, and antigen-binding fragments thereof, which are derived from any of the amino acid sequences provided in Table 1, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences according to Table 1, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present disclosure.

Useful herein are MET binding proteins such as human anti-MET antibodies and MET×MET bispecific antibodies comprising variants of any of the HCVR, LCVR, and/or CDR amino acid sequences shown in Table 1 herein having one or more conservative substitutions. For example, the present disclosure includes MET×MET bispecific antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences of Table 1.

The term "human antibody", as used herein, is intended to include antibodies having variable and constant regions derived from human germline immunoglobulin sequences. The human monoclonal antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include monoclonal antibodies in which CDR sequences derived from the germline of another mammalian species (e.g., mouse), have been grafted onto human FR sequences.

The term "multi-specific antigen-binding molecules", as used herein refers to bispecific, tri-specific or multi-specific antigen-binding molecules, and antigen-binding fragments thereof. Multi-specific antigen-binding molecules may be specific for different epitopes of one target polypeptide or may contain antigen-binding domains specific for epitopes of more than one target polypeptide. A multi-specific antigen-binding molecule can be a single multifunctional polypeptide, or it can be a multimeric complex of two or more polypeptides that are covalently or non-covalently associated with one another. The term "multi-specific antigen-binding molecules" includes antibodies of the present disclosure that may be linked to or co-expressed with another functional molecule, e.g., another peptide or protein. For example, an antibody or fragment thereof can be functionally linked (e.g., by chemical coupling, genetic fusion, non-covalent association or otherwise) to one or more other molecular entities, such as a protein or fragment thereof to produce a bi-specific or a multi-specific antigen-binding molecule with a second binding specificity. According to the present disclosure, the term "multi-specific antigen-binding molecules" also includes bi-specific, tri-specific or multi-specific antibodies or antigen-binding fragments thereof. In certain embodiments, an antibody of the present disclosure is functionally linked to another antibody or antigen-binding fragment thereof to produce a bispecific antibody with a second binding specificity. Bispecific and multi-specific antibodies of the present disclosure are described elsewhere herein.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1\times10^{-8}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to MET. Moreover, multi-specific antibodies that bind to one domain in MET and one or more additional antigens or a bi-specific that binds to two different regions of MET are nonetheless considered antibodies that "specifically bind", as used herein.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to bind to MET.

An "isolated antibody", as used herein, is intended to refer to an antibody that is substantially free of other antibodies (Abs) having different antigenic specificities (e.g., an isolated antibody that specifically binds MET, or a fragment thereof, is substantially free of Abs that specifically bind antigens other than MET.

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix. Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the disclosure to a database containing a large number of sequences from different organisms is the computer program BLAST, especially BLASTP or TBLASTN, using default parameters. See, e.g., Altschul et al. (1990) J. Mol. Biol. 215: 403-410 and (1997) Nucleic Acids Res. 25:3389-3402, each of which is herein incorporated by reference.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

As used herein, the term "subject" refers to an animal, preferably a mammal, in need of amelioration, prevention and/or treatment of a disease or disorder such as cancer.

II. Radiolabeled Immunoconjugates of MET Antibodies for Immuno-PET Imaging

Provided herein are radiolabeled antigen-binding proteins that bind MET protein. In some embodiments, the radiolabeled antigen-binding proteins comprise an antigen-binding protein covalently linked to one or more chelating moieties, which are chemical moieties that are capable of chelating a positron emitter.

In some embodiments, provided herein are antigen-binding proteins that bind MET, e.g., anti-MET antibodies or MET×MET bispecific antibodies, wherein said antigen-binding proteins that bind MET are covalently bonded to one or more moieties having the following structure:

$$-L-M_z$$

wherein L is a chelating moiety; M is a positron emitter; and z, independently at each occurrence, is 0 or 1; and wherein at least one of z is 1.

In some embodiments, the radiolabeled antigen-binding protein is a compound of Formula (I):

$$M-L-A-[L-M_z]_k \quad (I)$$

A is a protein that binds MET; L is a chelating moiety; M is a positron emitter; z is 0 or 1; and k is an integer from 0-30. In some embodiments, k is 1.

In certain embodiments, the radiolabeled antigen-binding protein is a compound of Formula (II):

$$A-[L-M]_k \quad (II)$$

wherein A is a protein that binds MET; L is a chelating moiety; M is a positron emitter; and k is an integer from 1-30.

In some embodiments, provided herein are compositions comprising a conjugate having the following structure:

$$A-L_k$$

wherein A is a protein that binds MET; L is a chelating moiety; and k is an integer from 1-30; wherein the conjugate is chelated with a positron emitter in an amount sufficient to provide a specific activity suitable for clinical PET imaging.

Suitable binding proteins, chelating moieties, and positron emitters are provided below.

A. MET Binding Proteins

Suitable MET binding protein are proteins that specifically bind to MET, including those described in U.S. Patent Publication No. 2018-0134794, incorporated herein by reference in its entirety. Amino acid sequence identifiers of exemplary anti-MET antibodies useful herein are listed in Table 1 of U.S. Patent Publication No. 2018-0134794 and amino acid sequence identifiers of exemplary MET×MET bispecific antibodies useful herein are listed in Table 5 of U.S. Patent Publication No. 2018-0134794. Both Tables are included below as Tables 1 and 2, respectively.

TABLE 1

| Amino Acid Sequence Identifiers | | | | | | | | |
|---|---|---|---|---|---|---|---|---|
| Antibody | SEQ ID NOS: | | | | | | | |
| Designation | HCVR | HCDR1 | HCDR2 | HCDR3 | LCVR | LCDR1 | LCDR2 | LCDR3 |
| H4H13290P2 | 2 | 4 | 6 | 8 | 138 | 140 | 142 | 144 |
| H4H13291P2 | 10 | 12 | 14 | 16 | 138 | 140 | 142 | 144 |
| H4H13295P2 | 18 | 20 | 22 | 24 | 138 | 140 | 142 | 144 |
| H4H13299P2 | 26 | 28 | 30 | 32 | 138 | 140 | 142 | 144 |
| H4H13300P2 | 34 | 36 | 38 | 40 | 138 | 140 | 142 | 144 |
| H4H13301P2 | 42 | 44 | 46 | 48 | 138 | 140 | 142 | 144 |
| H4H13302P2 | 50 | 52 | 54 | 56 | 138 | 140 | 142 | 144 |
| H4H13306P2 | 58 | 60 | 62 | 64 | 138 | 140 | 142 | 144 |
| H4H13309P2 | 66 | 68 | 70 | 72 | 138 | 140 | 142 | 144 |
| H4H13311P2 | 74 | 76 | 78 | 80 | 138 | 140 | 142 | 144 |
| H4H13312P2 | 82 | 84 | 86 | 88 | 138 | 140 | 142 | 144 |
| H4H13313P2 | 90 | 92 | 94 | 96 | 138 | 140 | 142 | 144 |
| H4H13316P2 | 98 | 100 | 102 | 104 | 138 | 140 | 142 | 144 |
| H4H13318P2 | 106 | 108 | 110 | 112 | 138 | 140 | 142 | 144 |
| H4H13319P2 | 114 | 116 | 118 | 120 | 138 | 140 | 142 | 144 |
| H4H13325P2 | 122 | 124 | 126 | 128 | 138 | 140 | 142 | 144 |
| H4H13331P2 | 130 | 132 | 134 | 136 | 138 | 140 | 142 | 144 |

TABLE 2

| MET × MET Bispecific Antibody Components Summary | | | | | | | | |
|---|---|---|---|---|---|---|---|---|
| | SEQ ID NOs: (Amino Acid Sequences) | | | | | | | |
| | First Antigen-Binding Domain (D1) | | | | Second Antigen-Binding Domain (D2) | | | |
| Bispecific Antibody | D1-HCVR | D1-HCDR1 | D1-HCDR2 | D1-HCDR3 | D2-HCVR | D2-HCDR1 | D2-HCDR2 | D2-HCDR3 |
| H4H14634D | | H4H13290P2 | | | | H4H13312P2 | | |
| (No. 10) | 2 | 4 | 6 | 8 | 82 | 84 | 86 | 88 |
| H4H14635D | | H4H13295P2 | | | | H4H13312P2 | | |
| (No. 42) | 18 | 20 | 22 | 24 | 82 | 84 | 86 | 88 |
| H4H14636D | | H4H13299P2 | | | | H4H13312P2 | | |
| (No. 74) | 26 | 28 | 30 | 32 | 82 | 84 | 86 | 88 |
| H4H14637D | | H4H13301P2 | | | | H4H13312P2 | | |
| (No. 90) | 42 | 44 | 46 | 48 | 82 | 84 | 86 | 88 |
| H4H14638D | | H4H13302P2 | | | | H4H13312P2 | | |
| (No. 106) | 50 | 52 | 54 | 56 | 82 | 84 | 86 | 88 |
| H4H14639D | | H4H13306P2 | | | | H4H13312P2 | | |
| (No. 122) | 58 | 60 | 62 | 64 | 82 | 84 | 86 | 88 |
| H4H14640D | | H4H13309P2 | | | | H4H13312P2 | | |
| (No. 138) | 66 | 68 | 70 | 72 | 82 | 84 | 86 | 88 |
| H4H14641D | | H4H13313P2 | | | | H4H13312P2 | | |
| (No. 187) | 90 | 92 | 94 | 96 | 82 | 84 | 86 | 88 |
| H4H16445D | | H4H13291P2 | | | | H4H13312P2 | | |
| (No. 26) | 10 | 12 | 14 | 16 | 82 | 84 | 86 | 88 |
| H4H16446D | | H4H13300P2 | | | | H4H13312P2 | | |
| (No. 58) | 34 | 36 | 38 | 40 | 82 | 84 | 86 | 88 |
| H4H16447D | | H4H13311P2 | | | | H4H13312P2 | | |
| (No. 154) | 74 | 76 | 78 | 80 | 82 | 84 | 86 | 88 |
| H4H16448D | | H4H13318P2 | | | | H4H13312P2 | | |
| (No. 219) | 106 | 108 | 110 | 112 | 82 | 84 | 86 | 88 |
| H4H16449D | | H4H13319P2 | | | | H4H13312P2 | | |
| (No. 235) | 114 | 116 | 118 | 120 | 82 | 84 | 86 | 88 |

* The number designation in parentheses under the bispecific antibody identifiers (e.g., "No. 10") indicates the bispecific antibody number depicted in the MET × MET bispecific antibody matrix of U.S. Patent Publication No. 2018-0134794, FIG. 1.

Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary anti-MET antibodies.

In some embodiments, the binding protein is an antibody or antigen binding fragment comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

In some embodiments, the binding protein is an antibody or antigen binding fragment comprising an LCVR amino acid sequence shown in Table 1, or a substantially similar sequence thereof having at least 90%, at least 95%, at least 98% or at least 99% sequence identity thereto.

In some embodiments, the binding protein is an antibody or antigen binding fragment comprising an HCVR and an LCVR amino acid sequence pair (HCVR/LCVR) comprising any of the HCVR amino acid sequences listed in Table 1 paired with the LCVR amino acid sequence shown in Table 1. According to certain embodiments, the present disclosure provides antibodies, or antigen-binding fragments thereof, comprising an HCVR/LCVR amino acid sequence pair contained within any of the exemplary anti-MET antibodies listed in Table 1. In certain embodiments, the HCVR/LCVR amino acid sequence pair is selected from the group consisting of SEQ ID NOs: 2/138, 10/138, 18/138, 26/138, 34/138, 42/138, 50/138, 58/138, 66/138, 74/138, 82/138, 90/138, 98/138, 106/138, 114/138, 122/138, and 130/138. In certain embodiments, the HCVR/LCVR amino acid sequence pair is selected from one of SEQ ID NOs: 58/138 (e.g., H4H13306P2) and 82/138 (e.g., H4H13312P2).

In some embodiments, the binding protein is an antibody or antigen binding fragment comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

In some embodiments, the binding protein is an antibody or antigen binding fragment comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

In some embodiments, the binding protein is an antibody or antigen binding fragment comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

In some embodiments, the binding protein is an antibody or antigen binding fragment comprising a light chain CDR1 (LCDR1) comprising an amino acid sequence shown in Table 1 or a substantially similar sequence thereof having at least 90%, at least 95%, at least 98% or at least 99% sequence identity.

In some embodiments, the binding protein is an antibody or antigen binding fragment comprising a light chain CDR2 (LCDR2) comprising an amino acid sequence shown in Table 1 or a substantially similar sequence thereof having at least 90%, at least 95%, at least 98% or at least 99% sequence identity.

In some embodiments, the binding protein is an antibody or antigen binding fragment comprising a light chain CDR3 (LCDR3) comprising an amino acid sequence shown in Table 1 or a substantially similar sequence thereof having at least 90%, at least 95%, at least 98% or at least 99% sequence identity.

In some embodiments, the binding protein is an antibody or antigen binding fragment comprising an HCDR3 and an LCDR3 amino acid sequence pair (HCDR3/LCDR3) comprising any of the HCDR3 amino acid sequences listed in Table 1 paired with the LCDR3 amino acid sequences shown in Table 1. According to certain embodiments, the present disclosure provides antibodies, or antigen-binding fragments thereof, comprising an HCDR3/LCDR3 amino acid sequence pair contained within any of the exemplary anti-MET antibodies listed in Table 1. In certain embodiments, the HCDR3/LCDR3 amino acid sequence pair is selected from the group consisting of SEQ ID NOs: 8/144 (e.g. H4H13290P2), 16/144 (e.g. H4H13291P2), 24/144 (H4H13295P2), 32/144 (H4H13299P2), 40/144 (H4H13300P2), 48/144 (H4H13301P2), 56/144 (H4H13302P2), 64/144 (H4H13306P2), 72/144 (H4H13309P2), 80/144 (H4H13311P2), 88/144 (H4H13312P2), 96/144 (H4H13313P2), 104/144 (H4H13316P2), 112/144 (H4H13318P2), 120/144 (H4H13319P2), 128/144 (H4H13325P2), and 136/144 (H4H13331P2).

In some embodiments, the binding protein is an antibody or antigen binding fragment comprising a set of six CDRs (i.e., HCDR1-HCDR2-HCDR3-LCDR1-LCDR2-LCDR3) contained within any of the exemplary anti-MET antibodies listed in Table 1. In certain embodiments, the HCDR1-HCDR2-HCDR3-LCDR1-LCDR2-LCDR3 amino acid sequence set is selected from the group consisting of SEQ ID NOs: 4-6-8-140-142-144 (e.g. H4H13290P2), 12-14-16-140-142-144 (e.g. H4H13291P2), 20-22-24-140-142-144 (H4H13295P2), 28-30-32-140-142-144 (H4H13299P2), 36-38-40-140-142-144 (H4H13300P2), 44-44-48-140-142-144 (H4H13301P2), 52-54-56-140-142-144 (H4H13302P2), 60-62-64-140-142-144 (H4H13306P2), 68-70-72-140-142-144 (H4H13309P2), 76-78-80-140-142-144 (H4H13311P2), 84-86-88-140-142-144 (H4H13312P2), 92-94-96-140-142-144 (H4H13313P2), 100-102-104-140-142-144 (H4H13316P2), 108-110-112-140-142-144 (H4H13318P2), 116-118-120-140-142-144 (H4H13319P2), 124-126-128-140-142-144 (H4H13325P2), and 132-134-136-140-142-144 (H4H13331P2).

In some embodiments, the binding protein is an antibody or antigen binding fragment comprising a set of six CDRs (i.e., HCDR1-HCDR2-HCDR3-LCDR1-LCDR2-LCDR3) contained within an HCVR/LCVR amino acid sequence pair as defined by any of the exemplary anti-MET antibodies listed in Table 1. For example, in some embodiments, the binding protein is an antibody or antigen binding fragment comprising the HCDR1-HCDR2-HCDR3-LCDR1-LCDR2-LCDR3 amino acid sequences set contained within an HCVR/LCVR amino acid sequence pair selected from the group consisting of SEQ ID NOs: 2/138 (e.g. H4H13290P2), 10/138 (e.g. H4H13291P2), 18/138 (H4H13295P2), 26/138 (H4H13299P2), 34/138 (H4H13300P2), 42/138 (H4H13301P2), 50/138 (H4H13302P2), 58/138 (H4H13306P2), 66/138 (H4H13309P2), 74/138 (H4H13311P2), 82/138 (H4H13312P2), 90/138 (H4H13313P2), 98/138 (H4H13316P2), 106/138 (H4H13318P2), 114/138 (H4H13319P2), 122/138 (H4H13325P2), and 130/138 (H4H13331P2).

Methods and techniques for identifying CDRs within HCVR and LCVR amino acid sequences are well known in the art and can be used to identify CDRs within the specified HCVR and/or LCVR amino acid sequences useful herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al- Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

In some embodiments, binding proteins are antibodies and antigen-binding fragments thereof that compete for specific binding to MET with an antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

Table 2 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the first antigen-binding domains (D1) and second antigen-binding domains (D2) of several exemplary MET×MET bispecific antibodies.

The individual anti-MET antigen-binding domains used to construct the bispecific antibodies useful herein were derived from various bivalent, monospecific anti-MET antibodies described in Examples 1 through 3 of U.S. Publication No. 2018-0134794. All anti-MET antibodies described herein comprise the same ("common") light chain (comprising the light chain variable region [LCVR] amino acid sequence of SEQ ID NO:138, and light chain CDR [LCDR1, LCDR2 and LCDR3] amino acid sequences of SEQ ID NOs: 140, 142 and 144). In addition, all of the bispecific antibodies contain a "D2" arm derived from the exemplary anti-MET antibody H4H13312P2. Thus, both antigen-binding domains (D1 and D2) of all of the bispecific antibodies described in this example comprise this common light chain variable region, and all D2 binding arms comprise the heavy chain variable region from H4H13312P2; however, the bispecific antibodies differ from one another in terms of their D1 heavy chain variable regions (HCVRs) and heavy chain CDRs (HCDRs). D1 and D2 are derived from different anti-MET antibodies and, consequently, bind to separate epitopes on the MET extracellular domain. I.e., D1 can bind a first epitope of human MET, e.g. an epitope comprising amino acids 192-204 of SEQ ID NO:155, and D2 can bind a second epitope of human MET comprising amino acids 305-315 and 421-455 of SEQ ID NO:155.

As used herein, the expression "antigen-binding domain" means any peptide, polypeptide, nucleic acid molecule, scaffold-type molecule, peptide display molecule, or polypeptide-containing construct that is capable of specifically binding a particular antigen of interest (e.g., human MET). The term "specifically binds" or the like, as used herein, means that the antigen-binding domain forms a complex with a particular antigen characterized by a dissociation constant ($K_D$) of 500 pM or less, and does not bind other unrelated antigens under ordinary test conditions. "Unrelated antigens" are proteins, peptides or polypeptides that have less than 95% amino acid identity to one another.

Exemplary categories of antigen-binding domains that can be used in the context of the present disclosure include antibodies, antigen-binding portions of antibodies, peptides that specifically interact with a particular antigen (e.g., peptibodies), receptor molecules that specifically interact with a particular antigen, proteins comprising a ligand-binding portion of a receptor that specifically binds a particular antigen, antigen-binding scaffolds (e.g., DARPins, HEAT repeat proteins, ARM repeat proteins, tetratricopeptide repeat proteins, and other scaffolds based on naturally occurring repeat proteins, etc., [see, e.g., Boersma and Pluckthun, 2011, *Curr. Opin. Biotechnol.* 22:849-857, and references cited therein]), and aptamers or portions thereof.

Methods for determining whether two molecules specifically bind one another are well known in the art and include, for example, equilibrium dialysis, surface plasmon resonance, and the like. For example, an antigen-binding domain, as used in the context of the present disclosure, includes polypeptides that bind a particular antigen (e.g., a target molecule [T] or an internalizing effector protein [E]) or a portion thereof with a $K_D$ of less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, less than about 10 pM, less than about 5 pM, less than about 4 pM, less than about 2 pM, less than about 1 pM, less than about 0.5 pM, less than about 0.2 pM, less than about 0.1 pM, or less than about 0.05 pM, as measured in a surface plasmon resonance assay.

The term "surface plasmon resonance", as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, NJ).

The term "$K_D$", as used herein, means the equilibrium dissociation constant of a particular protein-protein interaction (e.g., antibody-antigen interaction). Unless indicated otherwise, the $K_D$ values exhibited by the antibodies useful herein refer to $K_D$ values determined by surface plasmon resonance assay at 25° C. or 37° C.

As indicated above, an "antigen-binding domain" (D1 and/or D2) may comprise or consist of an antibody or antigen-binding fragment of an antibody. The term "antibody," as used herein, means any antigen-binding molecule or molecular complex comprising at least one complementarity determining region (CDR) that specifically binds to or interacts with a particular antigen (e.g., human MET). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments, the FRs of the antibodies provided herein (or antigen-binding portion thereof) may be identical to the human germline sequences, or may be naturally or artificially modified. An amino acid consensus sequence may be defined based on a side-by-side analysis of two or more CDRs.

The D1 and/or D2 components of the bispecific antigen-binding molecules useful herein may comprise or consist of antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-CL; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (Xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

In some embodiments, the binding protein is a bispecific antigen-binding molecule comprising or consisting of human antibodies and/or recombinant human antibodies, or fragments thereof. The term "human antibody", as used herein, includes antibodies having variable and constant regions derived from human germline immunoglobulin sequences. Human antibodies may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Methods for making bispecific antibodies are known in the art and may be used to construct bispecific antigen-binding molecules useful in the conjugates described herein. Exemplary bispecific formats that can be used in the context of the present disclosure include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED)body, leucine zipper, Duobody, IgG1/IgG2, dual acting Fab (DAF)-IgG, and $Mab^2$ bispecific formats (see, e.g., Klein et al. 2012, mAbs 4:6, 1-11, and references cited therein, for a review of the foregoing formats).

Exemplary antigen-binding domains (D1 and D2) that can be included in the MET×MET bispecific antigen-binding molecules useful herein include antigen-binding domains derived from any of the anti-MET antibodies disclosed in Table 1. For example, the present disclosure includes MET×MET bispecific antigen-binding molecules comprising a D1 or D2 antigen-binding domain comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

The binding protein can be a MET×MET bispecific antigen-binding molecule comprising a D1 or D2 antigen-binding domain comprising an LCVR comprising an amino acid sequence shown in Table 1, or a substantially similar sequence thereof having at least 90%, at least 95%, at least 98% or at least 99% sequence identity thereto.

In some embodiments, the binding protein is a MET×MET bispecific antigen-binding molecule comprising a D1 or D2 antigen-binding domain comprising an HCVR and an LCVR amino acid sequence pair (HCVR/LCVR) comprising any of the HCVR amino acid sequences listed in Table 1 paired with the LCVR amino acid sequence shown in Table 1.

In some embodiments, the binding protein is a MET×MET bispecific antigen-binding molecule comprising a D1 or D2 antigen-binding domain comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

In some embodiments, the binding protein is a MET×MET bispecific antigen-binding molecule comprising a D1 or D2 antigen-binding domain comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

In some embodiments, the binding protein is a MET×MET bispecific antigen-binding molecule comprising a D1 or D2 antigen-binding domain comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

In some embodiments, the binding protein is a MET×MET bispecific antigen-binding molecule comprising a D1 or D2 antigen-binding domain comprising a light chain CDR1 (LCDR1) comprising an LCDR1 amino acid sequence shown in Table 1 or a substantially similar sequence thereof having at least 90%, at least 95%, at least 98% or at least 99% sequence identity.

In some embodiments, the binding protein is a MET×MET bispecific antigen-binding molecule comprising a D1 or D2 antigen-binding domain comprising a light chain CDR2 (LCDR2) comprising an LCDR2 amino acid sequence shown in Table 1 or a substantially similar sequence thereof having at least 90%, at least 95%, at least 98% or at least 99% sequence identity.

In some embodiments, the binding protein is a MET×MET bispecific antigen-binding molecule comprising a D1 or D2 antigen-binding domain comprising a light chain CDR3 (LCDR3) comprising an LCDR3 amino acid sequence shown in Table 1 or a substantially similar sequence thereof having at least 90%, at least 95%, at least 98% or at least 99% sequence identity.

In some embodiments, the binding protein is a MET×MET bispecific antigen-binding molecule comprising a D1 or D2 antigen-binding domain comprising an HCDR3 and an LCDR3 amino acid sequence pair (HCDR3/LCDR3) comprising any of the HCDR3 amino acid sequences listed in Table 1 paired with the LCDR3 amino acid sequence shown in Table 1.

In some embodiments, the binding protein is a MET×MET bispecific antigen-binding molecule comprising a D1 or D2 antigen-binding domain comprising a set of six CDRs (i.e., HCDR1-HCDR2-HCDR3-LCDR1-LCDR2-LCDR3) contained within any of the exemplary anti-MET antibodies listed in Table 1.

In some embodiments, the binding protein is a MET×MET bispecific antigen-binding molecule comprising a D1 or D2 antigen-binding domain comprising a set of six CDRs (i.e., HCDR1-HCDR2-HCDR3-LCDR1-LCDR2-LCDR3) contained within an HCVR/LCVR amino acid sequence pair as defined by any of the exemplary anti-MET antibodies listed in Table 1.

The MET×MET bispecific antigen-binding molecules useful herein may comprise a D1 antigen-binding domain derived from any of the anti-MET antibodies of Table 1, and a D2 antigen-binding domain derived from any other anti-MET antibody of Table 1. Non-limiting examples of MET×MET bispecific antibodies of the present disclosure are depicted in FIG. 1 of U.S. Patent Publication No. 2018-0134794, which illustrates the components of 272 exemplary MET×MET bispecific antibodies. Each numbered cell of the matrix (numbered 1 through 272) identifies a unique bispecific antibody comprising a "D1" antigen binding domain and a "D2" antigen binding domain, wherein the D1 antigen binding domain comprises the immunoglobulin variable domain (HCVR/LCVR amino acid sequence pair) or CDRs from the corresponding anti-MET antibody listed along the Y-axis, and wherein the D2 antigen binding domain comprises the immunoglobulin variable domain (HCVR/LCVR amino acid sequence pair) or CDRs from the corresponding anti-MET antibody listed along the X-axis. Thus, for example, the MET×MET bispecific antigen-binding molecule "number 10" shown in the matrix comprises a D1 antigen-binding domain comprising an HCVR/LCVR pair, or 6-CDR set, from the exemplary anti-MET antibody H4H13290P2, and a D2 antigen-binding domain comprising an HCVR/LCVR pair, or 6-CDR set, from the exemplary anti-MET antibody H4H13321P2. Additional examples of MET×MET bispecific antibodies provided herein are described in Example 4 of U.S. Patent Publication No. 2018-0134794.

In some embodiments, the binding protein is a MET×MET bispecific antigen binding molecule comprising a D1 antigen-binding domain and a D2 antigen-binding domain, wherein the D1 antigen binding domain comprises an HCVR/LCVR amino acid sequence pair of SEQ ID NOs: 58/138, or a substantially similar sequence thereof having at least 90%, at least 95%, at least 98% or at least 99% sequence identity, or a set of heavy and light chain CDRs (HCDR1-HCDR2-HCDR3-LCDR1-LCDR2-LCDR3) comprising SEQ ID NOs: 60-62-64-140-142-144, or a substantially similar sequence thereof having at least 90%, at least 95%, at least 98% or at least 99% sequence identity, and wherein the D2 antigen-binding domain comprises an HCVR/LCVR amino acid sequence pair of SEQ ID NOs: 82/138, or a substantially similar sequence thereof having at least 90%, at least 95%, at least 98% or at least 99% sequence identity, or a set of heavy and light chain CDRs (HCDR1-HCDR2-HCDR3-LCDR1-LCDR2-LCDR3) comprising SEQ ID NOs: 84-86-88-140-142-144, or a substantially similar sequence thereof having at least 90%, at least 95%, at least 98% or at least 99% sequence identity.

In some embodiments, the binding protein is a MET×MET bispecific antigen binding molecule comprising a D1 antigen-binding domain and a D2 antigen-binding domain, wherein the D1 antigen binding domain comprises an HCVR/LCVR amino acid sequence pair of SEQ ID NOs: 18/138, or a substantially similar sequence thereof having at least 90%, at least 95%, at least 98% or at least 99% sequence identity, or a set of heavy and light chain CDRs (HCDR1-HCDR2-HCDR3-LCDR1-LCDR2-LCDR3) comprising SEQ ID NOs: 20-22-24-140-142-144, or a substantially similar sequence thereof having at least 90%, at least 95%, at least 98% or at least 99% sequence identity, and wherein the D2 antigen-binding domain comprises an HCVR/LCVR amino acid sequence pair of SEQ ID NOs: 82/138, or a substantially similar sequence thereof having at least 90%, at least 95%, at least 98% or at least 99% sequence identity, or a set of heavy and light chain CDRs (HCDR1-HCDR2-HCDR3-LCDR1-LCDR2-LCDR3) comprising SEQ ID NOs: 84-86-88-140-142-144, or a substantially similar sequence thereof having at least 90%, at least 95%, at least 98% or at least 99% sequence identity.

In some embodiments, the binding protein is a MET×MET bispecific antigen binding molecule comprising a D1 antigen-binding domain and a D2 antigen-binding domain, wherein the D1 antigen binding domain comprises an HCVR/LCVR amino acid sequence pair of SEQ ID NOs: 58/138, or a set of heavy and light chain CDRs (HCDR1-HCDR2-HCDR3-LCDR1-LCDR2-LCDR3) comprising SEQ ID NOs: 60-62-64-140-142-144, and wherein the D2 antigen-binding domain comprises an HCVR/LCVR amino acid sequence pair of SEQ ID NOs: 82/138, or a set of heavy and light chain CDRs (HCDR1-HCDR2-HCDR3-LCDR1-LCDR2-LCDR3) comprising SEQ ID NOs: 84-86-88-140-142-144. An exemplary MET×MET bispecific antibody having these sequence characteristics is the bispecific antibody designated H4H14639D, also referred to as bispecific antibody No. 122, which comprises a D1 derived from H4H13306P2 and a D2 derived from H4H13312P2 (see Table 2 herein).

In some embodiments, the binding protein is a MET×MET bispecific antigen binding molecule comprising a D1 antigen-binding domain and a D2 antigen-binding domain, wherein the D1 antigen binding domain comprises an HCVR/LCVR amino acid sequence pair of SEQ ID NOs: 18/138, or a set of heavy and light chain CDRs (HCDR1-HCDR2-HCDR3-LCDR1-LCDR2-LCDR3) comprising SEQ ID NOs: 20-22-24-140-142-144, and wherein the D2 antigen-binding domain comprises an HCVR/LCVR amino acid sequence pair of SEQ ID NOs: 82/138, or a set of heavy and light chain CDRs (HCDR1-HCDR2-HCDR3-LCDR1-LCDR2-LCDR3) comprising SEQ ID NOs: 84-86-88-140-142-144. An exemplary MET×MET bispecific antibody having these sequence characteristics is the bispecific antibody designated H4H14635D, also referred to as bispecific antibody No. 42, which comprises a D1 derived from H4H13295P2 and a D2 derived from H4H13312P2 (see Table 2 herein).

The bispecific antigen-binding molecules useful herein may also comprise one or more multimerizing component(s). The multimerizing components can function to maintain the association between the antigen-binding domains (D1 and D2). As used herein, a "multimerizing component" is any macromolecule, protein, polypeptide, peptide, or amino acid that has the ability to associate with a second multimerizing component of the same or similar structure or constitution. For example, a multimerizing component may be a polypeptide comprising an immunoglobulin $C_H3$ domain. A non-limiting example of a multimerizing component is an Fc portion of an immunoglobulin, e.g., an Fc domain of an IgG selected from the isotypes IgG1, IgG2, IgG3, and IgG4, as well as any allotype within each isotype group. In certain embodiments, the multimerizing component is an Fc fragment or an amino acid sequence of 1 to about 200 amino acids in length containing at least one cysteine residues. In other embodiments, the multimerizing component is a cysteine residue, or a short cysteine-containing peptide. Other multimerizing domains include peptides or polypeptides comprising or consisting of a leucine zipper, a helix-loop motif, or a coiled-coil motif.

In certain embodiments, the bispecific antigen-binding molecules useful herein comprise two multimerizing domains, M1 and M2, wherein D1 is attached to M1 and D2 is attached to M2, and wherein the association of M1 with M2 facilitates the physical linkage of D1 and D2 to one another in a single bispecific antigen-binding molecule. In certain embodiments, M1 and M2 are identical to one another. For example, M1 can be an Fc domain having a particular amino acid sequence, and M2 is an Fc domain with the same amino acid sequence as M1. Alternatively, M1 and M2 may differ from one another at one or more amino acid position. For example, M1 may comprise a first immunoglobulin (Ig) $CH^3$ domain and M2 may comprise a second Ig $C_H3$ domain, wherein the first and second Ig $CH^3$ domains differ from one another by at least one amino acid, and wherein at least one amino acid difference reduces binding of the targeting construct to Protein A as compared to a reference construct having identical M1 and M2 sequences. In one embodiment, the Ig $CH^3$ domain of M1 binds Protein A and the Ig $C_H3$ domain of M2 contains a mutation that reduces or abolishes Protein A binding such as an H95R modification (by IMGT exon numbering; H435R by EU numbering). The $C_H3$ of M2 may further comprise a Y96F modification (by IMGT; Y436F by EU). Further modifications that may be found within the $C_H3$ of M2 include: D16E, L18M, N44S, K52N, V57M, and V82I (by IMGT; D356E, L358M, N384S, K392N, V397M, and V422I by EU) in the case of an IgG1 Fc domain; N44S, K52N, and V82I (IMGT; N384S, K392N, and V422I by EU) in the case of an IgG2 Fc domain; and Q15R, N44S, K52N, V57M, R69K, E79Q, and V82I (by IMGT; Q355R, N384S, K392N, V397M, R409K, E419Q, and V422I by EU) in the case of an IgG4 Fc domain.

In some embodiments, the binding protein may be "isolated." An "isolated bispecific antigen-binding molecule," as used herein, means a bispecific antigen-binding molecule that has been identified and separated and/or recovered from at least one component of its natural environment. For example, a bispecific antibody that has been separated or removed from at least one component of an organism, or from a tissue or cell in which the antibody is produced, is an "isolated bispecific antibody" for purposes of the present disclosure. An isolated bispecific antigen-binding molecule also includes molecules in situ within a recombinant cell. Isolated bispecific antigen-binding molecules are molecules that have been subjected to at least one purification or isolation step. According to certain embodiments, an isolated bispecific antigen-binding molecule may be substantially free of other cellular material and/or chemicals.

The bispecific antigen-binding molecules useful herein, or the antigen-binding domains thereof (D1 and/or D2) may comprise one or more amino acid substitutions, insertions and/or deletions in the framework and/or CDR regions of the heavy and light chain variable domains as compared to the corresponding germline sequences from which the antigen-binding proteins or antigen-binding domains were derived. Such mutations can be readily ascertained by comparing the amino acid sequences of Table 1 to germline sequences available from, for example, public antibody sequence databases. The bispecific antigen-binding molecules useful herein, or the antigen-binding domains thereof (D1 and/or D2), which are derived from any of the amino acid sequences shown in Tables 1 and 2, can comprise one or more amino acids within one or more framework and/or CDR regions that are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations").

A person of ordinary skill in the art, starting with the heavy and light chain variable region sequences of Tables 1 and 2, can easily produce numerous bispecific antigen-binding molecules, or antigen-binding domains thereof (D1 and/or D2), which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived).

In some embodiments, the binding protein may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. For example, bispecific antigen-binding molecules, or the antigen-binding domains thereof (D1 and/or D2), that contain one or more germline mutations can be easily tested for one or more desired property such as, improved binding specificity, increased binding affinity, improved or enhanced antagonistic or agonistic biological properties (as the case may be), reduced immunogenicity, etc. Bispecific antigen-binding molecules, or the antigen-binding domains thereof (D1 and/or D2), obtained in this general manner are encompassed within the present disclosure.

In some embodiments, the binding protein is an anti-MET antibody or bispecific antigen-binding molecule comprising variants of any of the HCVR, LCVR, and/or CDR amino acid sequences provided in Tables 1 and 2. Exemplary variants included within this aspect include variants of any of the HCVR, LCVR, and/or CDR amino acid sequences of Tables 1 and 2 having one or more conservative substitutions. For example, binding proteins useful herein include anti-MET antibodies and MET×MET bispecific antigen-binding molecules having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 1 herein.

Exemplary variants also include variants having substantial sequence identity to any of the HCVR, LCVR, and/or CDR amino acid sequences of the antibodies provided in Table 1. As used herein in the context of amino acid sequences, the term "substantial identity" or "substantially identical" means that two amino acid sequences, when optimally aligned, such as by the programs GAP or BESTFIT using default gap weights, share at least 95%, 98% or 99% sequence identity. In certain embodiments, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence identity between two different amino acid sequences is typically measured using sequence analysis software. Sequence analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence provided herein to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

In some embodiments, the binding protein is an anti-MET antibody or MET×MET bispecific antigen binding protein comprising an Fc domain comprising one or more mutations which enhance or diminish antibody binding to the FcRn receptor, e.g., at acidic pH as compared to neutral pH. For example, anti-MET antibodies and MET×MET bispecific antigen binding proteins can comprise a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0).

Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the binding protein can be anti-MET antibodies and MET×MET bispecific antigen binding proteins comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains useful herein, are contemplated within the scope of the present disclosure.

In some embodiments, the binding proteins are antibodies and antigen-binding fragments thereof that cross-compete for binding to MET with a reference antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

Binding Protein Characteristics

In some embodiments, the binding protein is an isolated antibody or antigen-binding fragment that binds monomeric human MET with high affinity. For example, binding proteins useful herein include anti-MET antibodies that bind monomeric human MET (e.g., hMET.mmh) with a $K_D$ of less than about 230 nM as measured by surface plasmon resonance at 25° C. or 37° C., e.g., using an assay format as defined in Example 3 of U.S. Patent Publication No. 2018-0134794, or a substantially similar assay. According to certain embodiments, anti-MET antibodies useful herein bind monomeric human MET at 37° C. with a $K_D$ of less than about 230 nM, less than about 200 nM, less than about 150 nM, less than about 100 nM, less than about 50 nM, less than about 25 nM, less than about 20 nM, less than about 10 nM, less than about 8 nM, less than about 6 nM, less than about 5 nM, less than about 4 nM, or less than about 3 nM, as measured by surface plasmon resonance, e.g., using an assay format as defined in Example 3 of U.S. Patent Publication No. 2018-0134794, or a substantially similar assay.

In some embodiments, the binding protein is an antibody or antigen-binding fragment thereof that binds monomeric human MET (e.g., hMET.mmh) with a dissociative half-life (t½) of greater than about 1 minute as measured by surface plasmon resonance at 25° C. or 37° C., e.g., using an assay format as defined in Example 3 of U.S. Patent Publication No. 2018-0134794, or a substantially similar assay. According to certain embodiments, such anti-MET antibodies bind monomeric human MET at 37° C. with a t½ of greater than about 1 minute, greater than about 2 minutes, greater than about 4 minutes, greater than about 6 minutes, greater than about 8 minutes, greater than about 10 minutes, greater than about 12 minutes, greater than about 14 minutes, greater than about 16 minutes, greater than about 18 minutes, or greater than about 20 minutes, or longer, as measured by surface plasmon resonance, e.g., using an assay format as defined in Example 3 of U.S. Patent Publication No. 2018-0134794, or a substantially similar assay.

In some embodiments, the binding protein is an antibody or antigen-binding fragment thereof that binds dimeric human MET (e.g., hMET.mFc) with high affinity. For example, such anti-MET antibodies bind dimeric human MET with a $K_D$ of less than about 3 nM as measured by surface plasmon resonance at 25° C. or 37° C., e.g., using an assay format as defined in Example 3 of U.S. Patent Publication No. 2018-0134794, or a substantially similar assay. Anti-MET antibodies useful herein can bind dimeric human MET at 37° C. with a $K_D$ of less than about 3 nM, less than about 2 nM, less than about 1 nM, less than about 0.9 nM, less than about 0.8 nM, less than about 0.7 nM, less than about 0.6 nM, less than about 0.5 nM, less than about 0.4 nM, less than about 0.3 nM, or less than about 0.25 nM, as measured by surface plasmon resonance, e.g., using an assay format as defined in Example 3 of U.S. Patent Publication No. 2018-0134794, or a substantially similar assay.

In some embodiments, the binding protein is an antibody or antigen-binding fragment thereof that binds dimeric human MET (e.g., hMET.mFc) with a dissociative half-life (t½) of greater than about 4 minutes as measured by surface plasmon resonance at 25° C. or 37° C., e.g., using an assay format as defined in Example 3 of U.S. Patent Publication No. 2018-0134794, or a substantially similar assay. According to certain embodiments, anti-MET antibodies useful herein bind dimeric human MET at 37° C. with a t½ of greater than about 4 minutes, greater than about 5 minutes, greater than about 10 minutes, greater than about 20 minutes, greater than about 30 minutes, greater than about 40 minutes, greater than about 50 minutes, greater than about 60 minutes, greater than about 70 minutes, greater than about 80 minutes, greater than about 90 minutes, greater than about 100 minutes, greater than about 105 minutes, or longer, as measured by surface plasmon resonance, e.g., using an assay format as defined in Example 3 of U.S. Patent Publication No. 2018-0134794, or a substantially similar assay.

In some embodiments, the binding protein is an antibody or antigen-binding fragment thereof that binds dimeric human MET (e.g., hMET.mFc) with a dissociative half-life (t½) of greater than about 10 minutes as measured by surface plasmon resonance at 25° C. or 37° C., e.g., using an assay format as defined in Example 5 of U.S. Patent Publication No. 2018-0134794, or a substantially similar assay. According to certain embodiments, a MET×MET bispecific antigen-binding protein useful herein binds dimeric human MET at 37° C. with a t½ of greater than about 10 minutes, greater than about 20 minutes, greater than about 30 minutes, greater than about 40 minutes, greater than about 50 minutes, greater than about 60 minutes, greater than about 70 minutes, greater than about 80 minutes, greater than about 90 minutes, greater than about 100 minutes, greater than about 200 minutes, greater than about 300 minutes, greater than about 400 minutes, greater than about 500 minutes, greater than about 600 minutes, greater than about 700 minutes, greater than about 800 minutes, greater than about 900 minutes, greater than about 1000 minutes, greater than about 1100 minutes, or longer, as measured by surface plasmon resonance, e.g., using an assay format as defined in Example 5 of U.S. Patent Publication No. 2018-0134794, or a substantially similar assay.

In some embodiments, the binding protein is an antibody or antigen-binding fragment thereof, for example, a MET×MET bispecific antigen-binding protein, that blocks the interaction between HGF and MET, e.g., in an in vitro ligand-binding assay. A MET×MET bispecific antigen-binding protein useful herein can block HGF binding to cells expressing human MET, and induce minimal or no MET activation in the absence of HGF signaling. For example, useful herein are MET×MET bispecific antigen-binding proteins that exhibit a degree of MET agonist activity in a cell-based MET activity reporter assay that is less than 50%, less than 40%, less than 30%, less than 20%, less than 10%, less than 5%, less than 3%, less than 2% or less than 1% of the MET agonist activity observed in an equivalent activity reporter assay using a monospecific antibody comprising D1 or D2 alone.

In one embodiment, the antibody or fragment thereof is a human monoclonal antibody or antigen-binding fragment thereof that binds to MET, wherein the antibody or fragment thereof exhibits one or more of the following characteristics: (i) comprises a HCVR having an amino acid sequence selected from the group consisting of SEQ ID NO: 2, 10, 18, 26, 34, 42, 50, 58, 66, 74, 82, 90, 98, 106, 114, 122, and 130, or a substantially similar sequence thereof having at least 90%, at least 95%, at least 98% or at least 99% sequence identity; (ii) comprises a LCVR having an amino acid sequence of SEQ ID NO: 138, or a substantially similar sequence thereof having at least 90%, at least 95%, at least 98% or at least 99% sequence identity; (iii) comprises a HCDR3 domain having an amino acid sequence selected from the group consisting of SEQ ID NO: 8, 16, 24, 32, 40, 48, 56, 64, 72, 80, 88, 96, 104, 112, 120, 128 and 136, or a substantially similar sequence thereof having at least 90%, at least 95%, at least 98% or at least 99% sequence identity; and a LCDR3 domain having an amino acid sequence of SEQ ID NO: 144, or a substantially similar sequence thereof having at least 90%, at least 95%, at least 98% or at least 99% sequence identity; (iv) comprises a HCDR1 domain having an amino acid sequence selected from the group consisting of SEQ ID NO: 4, 12, 20, 28, 36, 44, 52, 60, 68, 76, 84, 92, 100, 108, 116, 124, and 132, or a substantially similar sequence thereof having at least 90%, at least 95%, at least 98% or at least 99% sequence identity; a HCDR2 domain having an amino acid sequence selected from the group consisting of SEQ ID NO: 6, 14, 22, 30, 38, 46, 54, 62, 70, 78, 86, 94, 102, 110, 118, 126, and 134, or a substantially similar sequence thereof having at least 90%, at least 95%, at least 98% or at least 99% sequence identity; a LCDR1 domain having an amino acid sequence of SEQ ID NO: 140, or a substantially similar sequence thereof having at least 90%, at least 95%, at least 98% or at least 99% sequence identity; and a LCDR2 domain having an amino acid sequence of SEQ ID NO: 142, or a substantially similar sequence thereof having at least 90%, at least 95%, at least 98% or at least 99% sequence identity; (v) is a multi-specific antigen-binding molecule comprising a first binding specificity to MET and a second binding specificity to a tumor specific antigen; (vi) is a multi-specific antigen-binding molecule comprising a first binding specificity to one epitope of MET and a second binding specificity to a second epitope of MET; (vii) binds to monomeric human MET (e.g., hMET.mmh) with a $K_D$ of less than about 230 nM as measured by surface plasmon resonance at 25° C. or 37° C.; (viii) binds to dimeric human MET with a $K_D$ of less than about 3 nM as measured by surface plasmon resonance at 25° C. or 37° C.; (ix) blocks the binding of HGF to MET; and (x) suppresses tumor growth and increases survival in subjects with cancer.

In one embodiment, the antibody or fragment thereof is a human monoclonal antibody or antigen-binding fragment thereof that blocks HGF binding to MET, wherein the antibody or fragment thereof exhibits one or more of the following characteristics: (i) comprises a HCVR having an amino acid sequence selected from the group consisting of SEQ ID NO: 2, 10, 18, 26, 34, 42, 50, 58, 66, 74, 82, 90, 98, 106, 114, 122, and 130, or a substantially similar sequence thereof having at least 90%, at least 95%, at least 98% or at least 99% sequence identity; (ii) comprises a LCVR having an amino acid sequence of SEQ ID NO: 138, or a substantially similar sequence thereof having at least 90%, at least 95%, at least 98% or at least 99% sequence identity; (iii) comprises a HCDR3 domain having an amino acid sequence selected from the group consisting of SEQ ID NO: 8, 16, 24, 32, 40, 48, 56, 64, 72, 80, 88, 96, 104, 112, 120, 128 and 136, or a substantially similar sequence thereof having at least 90%, at least 95%, at least 98% or at least 99% sequence identity; and a LCDR3 domain having an amino acid sequence of SEQ ID NO: 144, or a substantially similar sequence thereof having at least 90%, at least 95%, at least 98% or at least 99% sequence identity; (iv) comprises a HCDR1 domain having an amino acid sequence selected from the group consisting of SEQ ID NO: 4, 12, 20, 28, 36, 44, 52, 60, 68, 76, 84, 92, 100, 108, 116, 124, and 132, or a substantially similar sequence thereof having at least 90%, at least 95%, at least 98% or at least 99% sequence identity; a HCDR2 domain having an amino acid sequence selected from the group consisting of SEQ ID NO: 6, 14, 22, 30, 38, 46, 54, 62, 70, 78, 86, 94, 102, 110, 118, 126, and 134, or a substantially similar sequence thereof having at least 90%, at least 95%, at least 98% or at least 99% sequence identity; a LCDR1 domain having an amino acid sequence of SEQ ID NO: 140, or a substantially similar sequence thereof having at least 90%, at least 95%, at least 98% or at least 99% sequence identity; and a LCDR2 domain having an amino acid sequence of SEQ ID NO: 142, or a substantially similar sequence thereof having at least 90%, at least 95%, at least 98% or at least 99% sequence identity; (v) is a multi-specific antigen-binding molecule comprising a first binding specificity to MET and a second binding specificity to a tumor specific antigen; (vi) is a multi-specific antigen-binding molecule comprising a first binding specificity to one epitope of MET and a second binding specificity to a second epitope of MET; (vii) binds to monomeric human MET (e.g., hMET.mmh) with a $K_D$ of less than about 230 nM as measured by surface plasmon resonance at 25° C. or 37° C.; (viii) binds to dimeric human MET with a $K_D$ of less than about 3 nM as measured by surface plasmon resonance at 25° C. or 37° C.; and (ix) suppresses tumor growth and increases survival in subjects with cancer.

In certain embodiments, the binding protein is a MET×MET bispecific antibody or antigen-binding fragment thereof, wherein a first antigen-binding domain (D1) binds a first epitope of human MET and a second antigen-binding domain (D2) binds a second epitope of human MET, either in natural form, or recombinantly produced, or to a fragment thereof. In some aspects, D1 and D2 do not compete with one another for binding to human MET. In some embodiments, the binding protein exhibits minimal agonist activity in a cell-based MET activity reporter assay. In some embodiments, the bispecific antigen-binding molecule exhibits a degree of MET agonist activity in a cell-based MET activity reporter assay that is less than 10% of the MET agonist activity of a monovalent antigen-binding molecule comprising D1 or D2 alone. In some embodiments, the bispecific antigen-binding molecule promotes degradation of cell surface-expressed MET. In some embodiments, the bispecific antigen-binding molecule inhibits the growth or promotes tumor regression of tumors harboring MET genetic alterations. In some embodiments, the bispecific antigen-binding molecule inhibits the growth or promotes tumor regression of tumors whose growth is driven by autocrine HGF signaling.

In some embodiments, anti-MET antibodies or MET×MET bispecific antibodies useful herein bind to the same epitope, or a portion of the epitope, as any of the specific exemplary antibodies described herein in Table 1 or Table 2, or an antibody having the CDR sequences of any of the exemplary antibodies described in Table 1 or Table 2. Likewise, suitable binding proteins also include anti-MET antibodies or MET×MET bispecific antibodies that compete for binding to MET or a MET fragment with any of the specific exemplary antibodies described herein in Table 1 or Table 2, or an antibody having the CDR sequences of any of the exemplary antibodies described in Table 1 or Table 2. For example, suitable binding proteins include anti-MET antibodies and MET×MET bispecific antibodies that cross-compete for binding to MET with one or more antibodies as defined in U.S. Patent Publication No. 2018-0134794, or cross-compete for binding to MET with one or more antibodies as defined in U.S. Patent Publication No. 2018-0134794.

The antibodies and antigen-binding fragments described herein specifically bind to MET and modulate the interaction of MET with HGF. The MET×MET bispecific antibodies may bind to MET with high affinity or with low affinity. In certain embodiments, the antibodies are blocking antibodies wherein the antibodies bind to MET and block the interaction of MET with HGF. In some embodiments, the blocking antibodies of the disclosure block the binding of HGF to MET. In some embodiments, the blocking antibodies are useful for treating a subject suffering from cancer. They may be used to inhibit the growth of tumor cells in a subject. They may be used alone or as adjunct therapy with other therapeutic moieties or modalities known in the art for treating cancer. In certain embodiments, the MET×MET bispecific antibodies that bind to MET with a low affinity are used as multi-specific antigen-binding molecules wherein the first binding specificity binds to MET with a low affinity and the second binding specificity binds to a different epitope of MET or a tumor specific antigen.

Certain anti-MET antibodies and MET×MET bispecific antibodies of the present disclosure are able to bind to and neutralize the activity of MET, as determined by in vitro or in vivo assays. The ability of the antibodies of the disclosure to bind to and neutralize the activity of MET may be measured using any standard method known to those skilled in the art, including binding assays, or activity assays, as described herein.

Non-limiting, exemplary in vitro assays for measuring binding activity are illustrated in Examples 3 and 6 of US-2018-0134794 A1. In Example 6, the binding affinities and kinetic constants of human MET×MET bispecific antibodies for human MET were determined by surface plasmon resonance and the measurements were conducted on a T200 Biacore instrument. In Example 7 US-2018-0134794, blocking assays were used to determine the ability of the anti-MET antibodies and MET×MET bispecific antibodies to block MET-binding ability of HGF. In Example 4 of US-2018-0134794, blocking assays were used to determine cross-competition between different anti-MET antibodies. Example 8 of US-2018-0134794 describes the growth inhibition of cells overexpressing MET by anti-MET antibodies and MET×MET bispecific antibodies. In Example 10 of US-2018-0134794, a MET×MET bispecific antibody is shown to induce MET degradation and inhibit both MET and ERK phosphorylation. US-2018-0134794 also provides several examples demonstrating tumor growth inhibition or tumor regression, both in vivo and in vitro, induced by a MET×MET bispecific antibody.

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to specifically bind to MET. An antibody fragment may include a Fab fragment, a $F(ab')_2$ fragment, a Fv fragment, a dAb fragment, a fragment containing a CDR, or an isolated CDR. In certain embodiments, the term "antigen-binding fragment" refers to a polypeptide or fragment thereof of a multi-specific antigen-binding molecule. In such embodiments, the term "antigen-binding fragment" includes, e.g., an extracellular domain of HGF which binds specifically to MET. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-CL; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present disclosure using routine techniques available in the art.

The anti-MET antibodies and MET×MET bispecific antibodies and antibody fragments useful herein encompass proteins having amino acid sequences that vary from those of the described antibodies, but that retain the ability to bind MET. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present disclosure encompass sequences that comprise one or more additions, deletions, or substitutions of nucleotides when compared to the disclosed sequence, but that encode an antibody or antibody fragment that is essentially bioequivalent to an antibody or antibody fragment of the disclosure.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, or potency.

In one embodiment, two antigen-binding proteins are bioequivalent if a subject can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the disclosure may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Anti-MET antibodies and MET×MET bispecific antibodies useful herein can comprise an Fc domain comprising one or more mutations which enhance or diminish antibody binding to the FcRn receptor, e.g., at acidic pH as compared to neutral pH. For example, the present disclosure includes MET×MET bispecific antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, useful herein are anti-MET antibodies and MET×MET bispecific antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F). In one embodiment, the present disclosure includes MET×MET bispecific antibodies comprising an Fc domain comprising a S108P mutation in the hinge region of IgG4 to promote dimer stabilization. All possible combinations of the foregoing Fc domain mutations, and other mutations within the antibody variable domains provided herein in Table 1, are contemplated within the scope of the present disclosure.

Anti-MET antibodies and MET×MET bispecific antibodies useful herein can comprise a chimeric heavy chain constant ($C_H$) region, wherein the chimeric $C_H$ region comprises segments derived from the $C_H$ regions of more than one immunoglobulin isotype. For example, the antibodies may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies may comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., U.S. Ser. No. 14/170,166, filed Jan. 31, 2014, the disclosure of which is hereby incorporated by reference in its entirety).

B. Positron Emitters and Chelating Moieties

Suitable positron emitters include, but are not limited to, those that form stable complexes with the chelating moiety and have physical half-lives suitable for immuno-PET imaging purposes. Illustrative positron emitters include, but are not limited to, $^{89}$Zr, $^{68}$Ga, $^{64}$Cu, $^{44}$Sc, and $^{86}$Y. Suitable positron emitters also include those that directly bond with the MET binding protein, including, but not limited to, $^{76}$Br and $^{124}$I, and those that are introduced via prosthetic group, e.g., $^{18}$F, The chelating moieties described herein are chemical moieties that are covalently linked to the MET binding protein, e.g., MET×MET bispecific antibody, and comprise a portion capable of chelating a positron emitter, i.e., capable of reacting with a positron emitter to form a coordinated chelate complex. Suitable moieties include those that allow efficient loading of the particular metal and form metal-chelator complexes that are sufficiently stable in vivo for diagnostic uses, e.g., immuno-PET imaging. Illustrative chelating moieties include those that minimize dissociation of the positron emitter and accumulation in mineral bone, plasma proteins, and/or bone marrow depositing to an extent suitable for diagnostic uses.

Examples of chelating moieties include, but are not limited to, those that form stable complexes with positron emitters $^{89}$Zr, $^{68}$Ga, $^{64}$Cu, $^{44}$Sc, and/or $^{86}$Y. Illustrative chelating moieties include, but are not limited to, those described in Nature Protocols, 5(4): 739, 2010; *Bioconjugate Chem.*, 26(12): 2579 (2015); *Chem Commun* (Camb), 51(12): 2301 (2015); *Mol. Pharmaceutics,* 12: 2142 (2015); *Mol. Imaging Biol.*, 18: 344 (2015); *Eur. J. Nucl. Med. Mol. Imaging,* 37:250 (2010); *Eur. J. Nucl. Med. Mol. Imaging* (2016). doi:10.1007/s00259-016-3499-x; Bioconjugate Chem., 26(12): 2579 (2015); WO 2015/140212A1; and U.S. Pat. No. 5,639,879, incorporated by reference in their entireties.

Illustrative chelating moieties also include, but are not limited to, those that comprise desferrioxamine (DFO) (also known as deferoxamine), 1,4,7,10-tetraacetic acid (DOTA), diethylenetriaminepentaacetic acid (DTPA), ethylenediaminetetraacetic acid (EDTA), (1,4,7,10-Tetraazacyclododecane-1,4,7,10-tetra(methylene phosphonic) acid (DOTP), 1R, 4R, 7R, 10R)-α'α"α'"-Tetramethyl-1,4,7,10-tetraazacyclododecane-1,4,7,10-tetraacetic acid (DOTMA), 1,4,8,11-Tetraazacyclotetradecane-1,4,8, 11-tetraacetic acid (TETA), $H_4$octapa, $H_6$phospa, $H_2$dedpa, $H_5$decapa, $H_2$azapa, HOPO, DO2A, 1,4,7,10-Tetrakis(carbamoylmethyl)-1,4,7,10-tetraazacyclododecane (DOTAM), 1,4,7-triazacyclononane-N, N',N"-triacetic acid (NOTA), 1,4,7,10-Tetrakis(carbamoylmethyl)-1,4,7,10-tetraazacyclododecane (DOTAM), 1,4,8, 11-tetraazabicyclo[6.6.2]hexadecane-4, 11-dicetic acid (CB-TE2A), 1,4,7,10-Tetraazacyclododecane (Cyclen), 1,4,8,11-Tetraazacyclotetradecane (Cyclam), octadentate chelators, hexadentate chelators, phosphonate-based chelators, macrocyclic chelators, chelators comprising macrocyclic terephthalamide ligands, bifunctional chelators, fusarinine C and fusarinine C derivative chelators, triacetylfusarinine C (TAFC), ferrioxamine E (FOXE), ferrioxamine B (FOXB), ferrichrome A (FCHA), and the like.

In some embodiments, the chelating moieties are covalently bonded to the MET binding protein, e.g., antibody or antigen binding fragment thereof, via a linker moiety, which covalently attaches the chelating portion of the chelating moiety to the binding protein. In some embodiments, these linker moieties are formed from a reaction between a reactive moiety of the MET binding protein, e.g., cysteine or lysine of an antibody, and reactive moiety that is attached to a chelator, including, for example, a p-isothiocyanatobenyl group and the reactive moieties provided in the conjugation methods below. In addition, such linker moieties optionally comprise chemical groups used for purposes of adjusting polarity, solubility, steric interactions, rigidity, and/or the length between the chelating portion and MET binding protein.

C. Preparation of Radiolabeled MET Binding Protein Conjugates

The radiolabeled anti-MET antibody or MET×MET bispecific antibody conjugates can be prepared by (1) reacting a MET binding protein, e.g., a MET×MET bispecific antibody, with a molecule comprising a positron emitter chelator and a moiety reactive to the desirable conjugation site of the MET binding protein and (2) loading the desirable positron emitter.

Suitable conjugation sites include, but are not limited to, lysine and cysteine, both of which can be, for example, native or engineered, and can be, for example, present on the heavy or light chain of an antibody. Cysteine conjugation sites include, but are not limited to, those obtained from mutation, insertion, or reduction of antibody disulfide bonds. Methods for making cysteine engineered antibodies include, but are not limited to, those disclosed in WO2011/056983. Site-specific conjugation methods can also be used to direct the conjugation reaction to specific sites of an antibody, achieve desirable stoichiometry, and/or achieve desirable drug-to-antibody (DAR) ratios. Such conjugation methods are known to those of ordinary skill in the art and include, but are not limited to cysteine engineering and enzymatic and chemo-enzymatic methods, including, but not limited to, glutamine conjugation, Q295 conjugation, and transglutaminase-mediated conjugation, as well as those described in *J. Clin. Immunol.,* 36: 100 (2016), incorporated herein by reference in its entirety. Suitable moieties reactive to the desirable conjugation site generally enable efficient and facile coupling of the MET binding protein, e.g., antibody and positron emitter chelator. Moieties reactive to lysine and cysteine sites include electrophilic groups, which are known to those of ordinary skill. In certain aspects, when the desired conjugation site is lysine, the reactive moiety is an isothiocyanate, e.g., p-isothiocyanatobenyl group or reactive ester. In certain aspects, when the desired conjugation site is cysteine, the reactive moiety is a maleimide.

When the chelator is desferrioxamine (DFO) (also known as deferoxamine), suitable reactive moieties include, but are not limited to, an isothiocyantatobenzyl group, an n-hydroxysuccinimide ester,2,3,5,6 tetraflurorphenol ester, n-succinimidyl-S-acetylthioacetate, and those described in *BioMed Research International*, Vol 2014, Article ID 203601, incorporated herein by reference in its entirety. In certain embodiments, the MET binding protein is an antibody and the molecule comprising a positron emitter chelator and moiety reactive to the conjugation site is p-isothiocyantatobenzyl-desferrioxamine (p-SCN-Bn-DFO):

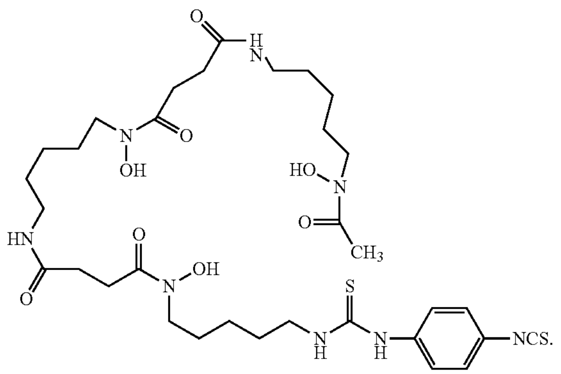

Positron emitter loading is accomplished by incubating the MET binding protein chelator conjugate with the positron emitter for a time sufficient to allow coordination of said positron emitter to the chelator, e.g., by performing the methods described in the examples provided herein, or substantially similar method.

D. Illustrative Embodiments of Conjugates

Included in the instant disclosure are radiolabeled antibody conjugates comprising an antibody or antigen binding fragment thereof that binds human MET, e.g. an anti-MET antibody or a MET×MET bispecific antibody, and a positron emitter. Also included in the instant disclosure are radiolabeled antibody conjugates comprising an anti-MET antibody or a MET×MET bispecific antibody, a chelating moiety, and a positron emitter.

In some embodiments, the chelating moiety comprises a chelator capable of forming a complex with $^{89}$Zr. In certain embodiments, the chelating moiety comprises desferrioxamine. In certain embodiments, the chelating moiety is p-isothiocyanatobenzyl-desferrioxamine.

In some embodiments, the positron emitter is $^{89}$Zr. In some embodiments, less than 1.0% of the MET binding protein is conjugated with the positron emitter, less than 0.9% of the MET binding protein is conjugated with the positron emitter, less than 0.8% of the MET binding protein is conjugated with the positron emitter, less than 0.7% of the MET binding protein is conjugated with the positron emitter, less than 0.6% of the MET binding protein is conjugated with the positron emitter, less than 0.5% of the MET binding protein is conjugated with the positron emitter, less than 0.4% of the MET binding protein is conjugated with the positron emitter, less than 0.3% of the MET binding protein is conjugated with the positron emitter, less than 0.2% of the MET binding protein is conjugated with the positron emitter, or less than 0.1% of the MET binding protein is conjugated with the positron emitter.

In some embodiments, the chelating moiety-to-antibody ratio of the conjugate is from 1 to 2. As used herein, "chelating moiety-to-antibody ratio" is the average chelator moiety to antibody ratio and is a measure of chelator load per antibody. This ratio is analogous to "DAR", i.e., drug-antibody ratio, which is used by those skilled in the art to measure drug load per antibody for antibody-drug conjugates (ADCs); in the context of the conjugates described herein for iPET imaging, the chelating moiety-to-antibody ratio can be ascertained using methods described herein and others known in the art for the determination of DAR, e.g. those described in Wang et al., Antibody-Drug Conjugates, The 21$^{st}$ Century Magic Bullets for Cancer (2015). In some embodiments, the chelating moiety-to-antibody ratio is from 1.0 to 4.0, or about 1.0 to 3.0, or about 1.0 to 2.0. In some embodiments, the chelating moiety-to-antibody ratio is about 1.26, for example, about 1.3.

In a particular embodiment, chelating moiety is p-isothiocyanatobenzyl-desferrioxamine and the positron emitter is $^{89}$Zr. In another particular embodiment, the chelating moiety is p-isothiocyanatobenzyl-desferrioxamine and the positron emitter is $^{89}$Zr, and the chelating moiety-to-antibody ratio of the conjugate is from 1 to 2.

In some embodiments, provided herein are antigen-binding proteins that bind MET, wherein said antigen-binding proteins that bind MET are covalently bonded to one or more moieties having the following structure:

$$\text{-L-M}_z$$

wherein L is a chelating moiety; M is a positron emitter; and z, independently at each occurrence, is 0 or 1; and wherein at least one of z is 1. In certain embodiments, the radiolabeled antigen-binding protein is a compound of Formula (I):

M-L-A-[L-$M_z$]$_k$ (I)

A is a protein that binds MET; L is a chelating moiety; M is a positron emitter; z is 0 or 1; and k is an integer from 0-30. In some embodiments, k is 1. In some embodiments, k is 2.

In some embodiments, L is:

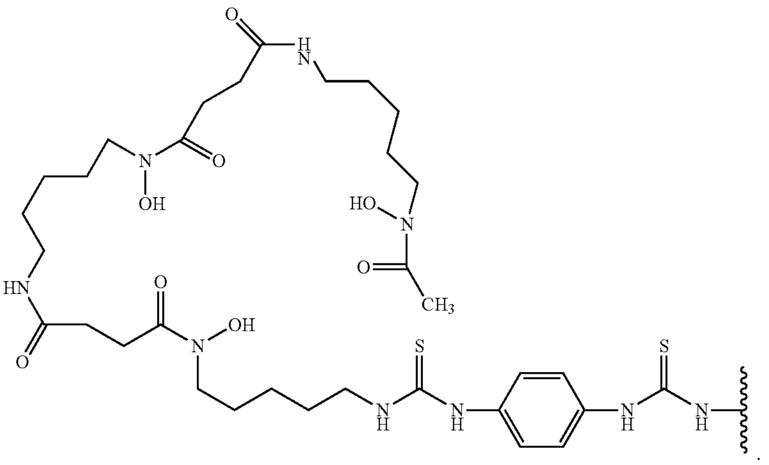 [SMILES: *NC(=S)Nc1ccc(NC(=S)NCCCCCN(O)C(=O)CCC(=O)NCCCCCN(O)C(=O)CCC(=O)NCCCCCN(O)C(C)=O)cc1]

In some embodiments, M is $^{89}$Zr.

In some embodiments, k is an integer from 1 to 2. In some embodiments, k is 1. In some embodiments, k is 2.

In some embodiments, -L-M is

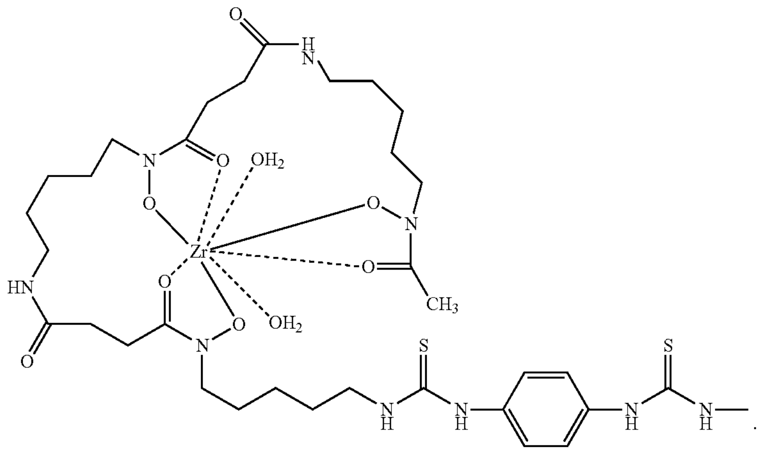

Included in the instant disclosure are also methods of synthesizing a radiolabeled antibody conjugates comprising contacting a compound of Formula (III):

(III)

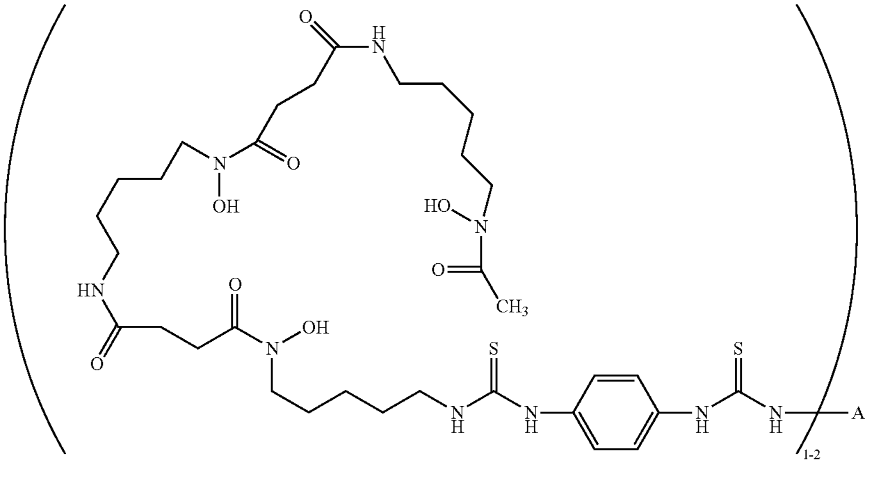

with $^{89}Zr$, wherein A is an antibody or antigen-binding fragment thereof that binds MET. In certain embodiments, the compound of Formula (III) is synthesized by contacting an antibody, or antigen binding fragment thereof, that binds MET, with p-SCN-Bn-DFO.

Provided herein is also the product of the reaction between a compound of Formula (III) with $^{89}Zr$.

Provided herein are compounds of Formula (III):

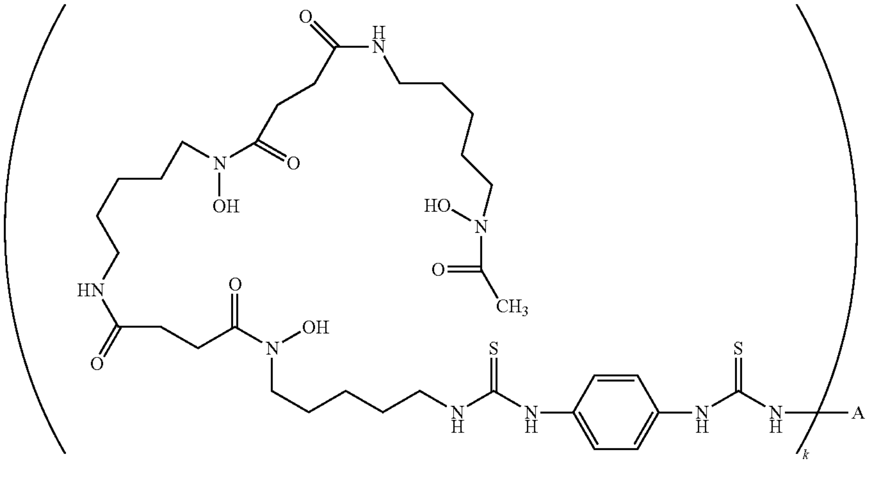

wherein A is an antibody or antigen binding fragment thereof that binds MET and k is an integer from 1-30. In some embodiments, k is 1 or 2.

Provided herein are antibody conjugates comprising (i) an antibody or antigen-binding fragment thereof that binds MET and (ii) one or more chelating moieties.

In some embodiments, the chelating moiety comprises:

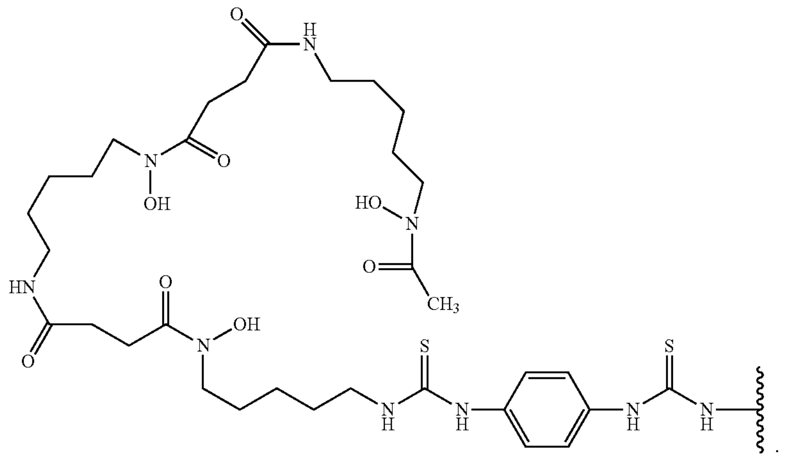 [SMILES: *NC(=S)Nc1ccc(NC(=S)NCCCCCN(O)C(=O)CCC(=O)NCCCCCN(O)C(=O)CCC(=O)NCCCCCN(O)C(C)=O)cc1]

 is a covalent bond to the antibody or antigen-binding fragment thereof.

In some aspects, the antibody conjugate has a chelating moiety-to-antibody ratio of from about 1.0 to about 2.0. In some aspects, the antibody conjugate has a chelating moiety-to-antibody ratio of about 1.3.

In some embodiments, provided herein are compositions comprising a conjugate having the following structure:

$A-L_k$ wherein A is a protein that binds MET; L is a chelating moiety; and k is an integer from 1-30; wherein the conjugate is chelated with a positron emitter in an amount sufficient to provide a specific activity suitable for clinical PET imaging. In some embodiments, the amount of chelated positron emitter is an amount sufficient to provide a specific activity of about 1 to about 50 mCi per 1-50 mg of the protein that binds MET.

In some embodiments, the amount of chelated positron emitter is an amount sufficient to provide a specific activity of up to 25 mCi, up to 20 mCi, up to 15 mCi, up to 12 mCi, or up to 10 mCi per 1-50 mg of the protein that binds MET, for example, in a range of about 3 to about 25 mCi, about 10 to about 25 mCi, about 1 to about 15 mCi, about 3 to about 15 mCi, about 5 to about 25 mCi, about 15 to about 25 mCi, or about 3 to about 10 mCi, or about 12 mCi, or about 21 mCi.

In some embodiments, the antibody or antigen-binding fragment thereof binds monomeric human MET with a binding dissociation equilibrium constant ($K_D$) of less than about 230 nM as measured in a surface plasmon resonance assay at 25° C. or 37° C.

In some embodiments, the antibody or antigen-binding fragment thereof binds dimeric human MET with a $K_D$ less than about 3 nM in a surface plasmon resonance assay at 25° C. or 37° C.

In some embodiments, the antibody or antigen-binding fragment thereof competes for binding to human MET with a reference antibody comprising the complementarity determining regions (CDRs) of a HCVR, wherein the HCVR has an amino acid sequence selected from the group consisting of HCVR sequences listed in Table 1; and the CDRs of a LCVR, wherein the LCVR has an amino acid sequence shown in Table 1. In some embodiments, the reference antibody or antigen-binding fragment thereof comprises an HCVR/LCVR amino acid sequence pair as set forth in Table 1. In some embodiments, the reference antibody comprises an HCVR/LCVR amino acid sequence pair selected from the group consisting of SEQ ID NOs: 2/138, 10/138, 18/138, 26/138, 34/138, 42/138, 50/138, 58/138, 66/138, 74/138, 82/138, 90/138, 98/138, 106/138, 114/138, 122/138 and 130/138.

In some embodiments, the antibody or antigen binding fragment thereof blocks HGF binding to MET. In some embodiments, the antibody or antigen binding fragment thereof do not increase or decrease MET binding to its ligands.

In some embodiments, the antibody or antigen-binding fragment thereof comprises the complementarity determining regions (CDRs) of a HCVR, wherein the HCVR has an amino acid sequence selected from the group consisting of SEQ ID NOs: 2, 10, 18, 26, 34, 42, 50, 58, 66, 74, 82, 90, 98, 106, 114, 122 and 130; and the CDRs of a LCVR, wherein the LCVR has an amino acid sequence of SEQ ID NO: 138. In certain embodiments, the isolated antibody comprises an HCVR/LCVR amino acid sequence pair selected from the group consisting of SEQ ID NOs: 2/138, 10/138, 18/138, 26/138, 34/138, 42/138, 50/138, 58/138, 66/138, 74/138, 82/138, 90/138, 98/138, 106/138, 114/138, 122/138 and 130/138.

In some embodiments, the antibody is a human monoclonal antibody or antigen-binding fragment thereof that binds specifically to human MET, wherein the antibody or antigen-binding fragment thereof comprises a heavy chain variable region (HCVR) having an amino acid sequence selected from the group consisting of HCVR sequences listed in Table 1.

In some embodiments, the antibody is a human monoclonal antibody or antigen-binding fragment thereof that binds specifically to human MET, wherein the antibody or antigen-binding fragment thereof comprises a light chain variable region (LCVR) having an amino acid sequence as shown in Table 1.

In some embodiments, the antibody a human monoclonal antibody or antigen-binding fragment thereof that binds specifically to human MET, wherein the antibody or antigen-binding fragment thereof comprises (a) a HCVR having an amino acid sequence selected from the group consisting of HCVR sequences listed in Table 1; and (b) a LCVR having an amino acid sequence as shown in Table 1.

In some embodiments, the antibody or antigen-binding fragment thereof comprises three heavy chain complementarity determining regions (CDRs) (HCDR1, HCDR2 and HCDR3) contained within any one of the heavy chain variable region (HCVR) sequences listed in Table 1; and three light chain CDRs (LCDR1, LCDR2 and LCDR3) contained within the light chain variable region (LCVR) sequence shown in Table 1.

In some embodiments, the antibody or antigen-binding fragment thereof comprises:

(a) a HCDR1 domain having an amino acid sequence selected from the group consisting of SEQ ID NOs: 4, 12, 20, 28, 36, 44, 52, 60, 68, 76, 84, 92, 100, 108, 116, 124 and 132;
(b) a HCDR2 domain having an amino acid sequence selected from the group consisting of SEQ ID NOs: 6, 14, 22, 30, 38, 46, 54, 62, 70, 78, 86, 94, 102, 110, 118, 126, and 134;
(c) a HCDR3 domain having an amino acid sequence selected from the group consisting of SEQ ID NOs: 8, 16, 24, 32, 40, 48, 56, 64, 72, 80, 88, 96, 104, 112, 120, 128 and 136;
(d) a LCDR1 domain having an amino acid sequence of SEQ ID NO: 140;
(e) a LCDR2 domain having an amino acid sequence of SEQ ID NO: 142; and
(f) a LCDR3 domain having an amino acid sequence of SEQ ID NO: 144.

In some embodiments, the antibody or antigen-binding fragment comprises a HCVR/LCVR amino acid sequence pair selected from the group consisting of SEQ ID NOs: 2/138, 10/138, 18/138, 26/138, 34/138, 42/138, 50/138, 58/138, 66/138, 74/138, 82/138, 90/138, 98/138, 106/138, 114/138, 122/138, and 130/138.

In some embodiments, the antibody or antigen-binding fragment thereof comprises the CDRs of a HCVR, wherein the HCVR has an amino acid sequence selected from the group consisting of SEQ ID NOs: 2, 10, 18, 26, 34, 42, 50, 58, 66, 74, 82, 90, 98, 106, 114, 122 and 130; and the CDRs of a LCVR, wherein the LCVR has an amino acid sequence of SEQ ID NO: 138.

In some embodiments, the antibody or antigen-binding fragment thereof is an anti-MET antibody comprising the CDRs within the HCVR/LCVR amino acid sequence pair of SEQ ID NOs: 82/138. In some embodiments, antibody or antigen-binding fragment thereof is an anti-MET antibody comprising the HCVR amino acid sequence of SEQ ID NO: 82 and the LCVR amino acid sequence of SEQ ID NO: 138.

In some embodiments, the antibody or antigen-binding fragment thereof is an anti-MET antibody comprising the CDRs within the HCVR/LCVR amino acid sequence pair of SEQ ID NOs: 18/138. In some embodiments, antibody or antigen-binding fragment thereof is an anti-MET antibody comprising the HCVR amino acid sequence of SEQ ID NO: 18 and the LCVR amino acid sequence of SEQ ID NO: 138.

In some embodiments, the antibody or antigen-binding fragment thereof is an anti-MET antibody comprising the CDRs within the HCVR/LCVR amino acid sequence pair of SEQ ID NOs: 58/138. In some embodiments, antibody or antigen-binding fragment thereof is an anti-MET antibody comprising the HCVR amino acid sequence of SEQ ID NO: 58 and the LCVR amino acid sequence of SEQ ID NO: 138.

In some embodiments, the antibody or antigen-binding fragment thereof is a MET×MET bispecific antigen-binding protein comprising the CDRs within the D1-HCVR amino acid sequence of SEQ ID NO: 58 and the CDRs within the D2-HCVR amino acid sequence of SEQ ID NO: 82. In some aspects, the MET×MET bispecific antigen-binding protein further comprises the CDRs within the LCVR amino acid sequence of SEQ ID NO: 138. In some embodiments, the antibody or antigen-binding fragment thereof is a MET×MET bispecific antigen-binding protein comprising the D1-HCVR amino acid sequence of SEQ ID NO: 58 and the D2-HCVR amino acid sequence of SEQ ID NO: 82. In some aspects, the MET×MET bispecific antigen-binding protein further comprises the LCVR amino acid sequence of SEQ ID NO: 138.

In some embodiments, the antibody or antigen-binding fragment thereof is a MET×MET bispecific antigen-binding protein comprising the CDRs within the D1-HCVR amino acid sequence of SEQ ID NO: 18 and the CDRs within the D2-HCVR amino acid sequence of SEQ ID NO: 82. In some aspects, the MET×MET bispecific antigen-binding protein further comprises the CDRs within the LCVR amino acid sequence of SEQ ID NO: 138. In some embodiments, the antibody or antigen-binding fragment thereof is a MET×MET bispecific antigen-binding protein comprising the D1-HCVR amino acid sequence of SEQ ID NO: 18 and the D2-HCVR amino acid sequence of SEQ ID NO: 82.

In some embodiments, the radiolabeled antibody conjugate comprises an antibody or antigen binding fragment thereof that binds MET, a chelating moiety, and a positron emitter, wherein the antibody or antigen-binding fragment thereof that binds MET comprises the CDRs within the D1-HCVR amino acid sequence of SEQ ID NO: 58, the CDRs within the D2-HCVR amino acid sequence of SEQ ID NO: 82, and the CDRs within the LCVR amino acid sequence of SEQ ID NO: 138, the chelating moiety is desferrioxamine, and the positron emitter is $^{89}$Zr.

In some embodiments, the radiolabeled antibody conjugate comprises an antibody or antigen binding fragment thereof that binds MET, a chelating moiety, and a positron emitter, wherein the antibody or antigen-binding fragment thereof that binds MET comprises the D1-HCVR amino acid sequence of SEQ ID NO: 58, the D2-HCVR amino acid sequence of SEQ ID NO: 82, and the LCVR amino acid sequence of SEQ ID NO: 138, the chelating moiety is desferrioxamine, and the positron emitter is $^{89}$Zr.

III. Methods of Using Radiolabeled Immunoconjugates

In certain aspects, the present disclosure provides diagnostic and therapeutic methods of use of the radiolabeled antibody conjugates of the present disclosure.

According to one aspect, the present disclosure provides methods of detecting MET in a tissue, the methods comprising administering a radiolabeled antibody conjugate of the provided herein to the tissue; and visualizing the MET expression by positron emission tomography (PET) imaging. In certain embodiments, the tissue comprises cells or cell lines. In certain embodiments, the tissue is present in a subject, wherein the subject is a mammal. In certain embodiments, the subject is a human subject. In certain embodiments, the subject has cancer.

According to one aspect, the present disclosure provides methods of imaging a tissue that expresses MET comprising administering a radiolabeled antibody conjugate of the present disclosure to the tissue; and visualizing the MET expression by positron emission tomography (PET) imaging. In one embodiment, the tissue is comprised in a tumor. In one embodiment, the tissue is comprised in a tumor cell culture or tumor cell line. In one embodiment, the tissue is comprised in a tumor lesion in a subject.

According to one aspect, the present disclosure provides methods for measuring response to an anti-MET therapy in a subject having cancer, wherein the response to therapy is measured by the change in MET expression relative to MET expression prior to therapy. The methods, according to this aspect, comprise administering a radiolabeled antibody conjugate provided herein to a subject in need thereof and visualizing the MET expression by positron emission tomography (PET) imaging. A decrease in MET expression, relative to MET expression prior to therapy, correlates to a positive response to anti-MET therapy.

According to one aspect, the present disclosure provides methods for determining if a subject with a solid tumor is suitable for anti-tumor therapy comprising an inhibitor of the HGF/MET signaling pathway, the methods comprising administering a radiolabeled antibody conjugate of the present disclosure to the subject, and localizing the administered radiolabeled antibody conjugate in the tumor by PET imaging wherein presence of the radiolabeled antibody conjugate in the tumor identifies the subject as suitable for anti-tumor therapy comprising an inhibitor of the HGF/MET signaling pathway.

Anti-tumor therapy useful according to the methods disclosed herein can be any therapeutically useful inhibitor of the HGF/MET signaling pathway, i.e. an inhibitor of HGF, an inhibitor of MET, or an inhibitor of EKR or any other downstream protein in the HGF/MET signaling pathway. In some aspects, the anti-tumor therapy comprises an anti-MET antibody or antigen-binding fragment thereof, for example, any one or more of the antibodies listed in Table 1. In some aspects, the anti-tumor therapy comprises any one or more of the MET×Met bispecific antibodies, for example, any one of the bispecific antibodies listed in Table 2. In some aspects, antibody, bispecific antibody, or antigen-binding fragment thereof is conjugated to a drug (i.e. an ADC) useful for treating cancer. Exemplary anti-MET ADCs are disclosed in US-2018-0134794 A1.

According to one aspect, the present disclosure provides methods for identifying a candidate subject for anti-tumor therapy comprising an inhibitor of the HGF/MET signaling pathway, the methods comprising administering a radiolabeled antibody conjugate of the present disclosure to a subject having a tumor, and localizing the administered radiolabeled antibody conjugate in the tumor by PET imaging wherein presence of the radiolabeled antibody conjugate in the tumor identifies the subject as suitable for anti-tumor therapy comprising an inhibitor of the HGF/MET signaling pathway.

According to one aspect, the present disclosure provides methods for predicting response of a subject to an anti-tumor therapy, the methods comprising determining if the tumor is MET-positive, wherein if the tumor is MET positive it predicts a positive response of the subject to an anti-tumor therapy. In certain embodiments, the tumor is determined positive by administering a radiolabeled antibody conjugate of the present disclosure and localizing the radiolabeled antibody conjugate in the tumor by PET imaging wherein presence of the radiolabeled antibody conjugate in the tumor indicates that the tumor is MET-positive.

According to one aspect, the present disclosure provides methods for predicting response of a subject having a solid tumor to an anti-tumor therapy, the methods comprising determining if the tumor is MET positive, wherein a positive response of the subject is predicted if the tumor is MET positive. In certain embodiments, the tumor is determined positive by administering a radiolabeled antibody conjugate of the present disclosure and localizing the radiolabeled antibody conjugate in the tumor by PET imaging wherein presence of the radiolabeled antibody conjugate in the tumor indicates that the tumor is MET positive.

According to one aspect, the present disclosure provides methods for detecting a MET-positive tumor in a subject. The methods, according to this aspect, comprise administering a radiolabeled antibody conjugate of the present disclosure to the subject; and determining localization of the radiolabeled antibody conjugate by PET imaging, wherein presence of the radiolabeled antibody conjugate in a tumor indicates that the tumor is MET-positive. In some aspects, the method for detecting identifies the location of the tumor. In some aspects, the method for detecting permits monitoring progress of anti-tumor treatment, for example, whether the tumor regresses or stops growing.

According to one aspect, the present disclosure provides methods for determining the size of a MET-positive tumor in a subject. The methods, according to this aspect, comprise administering a radiolabeled antibody conjugate of the present disclosure to the subject; and visualizing the radiolabeled antibody conjugate by PET imaging, wherein the size of the tumor can be determined.

Provided herein are also methods for determining the presence of MET expressing cells in a subject. The methods comprise administering a radiolabeled anti-MET antibody conjugate or MET×MET bispecific antibody conjugate described herein to the subject and visualizing MET expression by PET imaging.

Provided herein are methods for diagnosing and treating a subject with a tumor, the methods comprising administering a radiolabeled conjugate described herein to the subject wherein localization of the radiolabeled antibody conjugate is imaged via PET imaging to determine if the tumor is MET-positive; diagnosing the subject with a MET-positive tumor; and administering to the subject an anti-tumor therapy comprising an inhibitor of the HGF/MET signaling pathway.

Provided herein are methods for diagnosing a subject having a MET expressing tumor, the methods comprising administering a radiolabeled anti-MET antibody conjugate or MET×MET bispecific antibody conjugate described herein to the subject; visualizing MET expression by PET imaging; and diagnosing the subject with a MET expressing tumor when MET expression is visualized by PET imaging.

As used herein, the expression “a subject in need thereof” means a human or non-human mammal that exhibits one or more symptoms or indications of cancer, and/or who has been diagnosed with cancer, including a solid tumor and who needs treatment for the same. In many embodiments, the term “subject” may be interchangeably used with the term “patient”. For example, a human subject may be diagnosed with a primary or a metastatic tumor and/or with one or more symptoms or indications including, but not limited to, unexplained weight loss, general weakness, persistent fatigue, loss of appetite, fever, night sweats, bone pain, shortness of breath, swollen abdomen, chest pain/pressure, enlargement of spleen, and elevation in the level of a cancer-related biomarker (e.g., CA125). The expression includes subjects with primary or established tumors. In specific embodiments, the expression includes human subjects that have and/or need treatment for a solid tumor, e.g., colon cancer, breast cancer, lung cancer, prostate cancer, skin cancer, liver cancer, bone cancer, ovarian cancer, cervical cancer, pancreatic cancer, head and neck cancer, and brain cancer. The term includes subjects with primary or metastatic tumors (advanced malignancies). In certain embodiments, the expression "a subject in need thereof" includes patients with a solid tumor that is resistant to or refractory to or is inadequately controlled by prior therapy (e.g., treatment with an anti-cancer agent). For example, the expression includes subjects who have been treated with one or more lines of prior therapy such as treatment with chemotherapy (e.g., carboplatin or docetaxel). In certain embodiments, the expression "a subject in need thereof" includes patients with a solid tumor which has been treated with one or more lines of prior therapy but which has subsequently relapsed or metastasized.

In certain embodiments, the methods of the present disclosure are used in a subject with a solid tumor. The terms "tumor", "cancer" and "malignancy" are interchangeably used herein. As used herein, the term "solid tumor" refers to an abnormal mass of tissue that usually does not contain cysts or liquid areas. Solid tumors may be benign (not cancer) or malignant (cancer). For the purposes of the present disclosure, the term "solid tumor" means malignant solid tumors. The term includes different types of solid tumors named for the cell types that form them, viz. sarcomas, carcinomas and lymphomas. In certain embodiments, the term "solid tumor" includes cancers including, but not limited to, colorectal cancer, ovarian cancer, prostate cancer, breast cancer, brain cancer, cervical cancer, bladder cancer, anal cancer, uterine cancer, colon cancer, liver cancer, pancreatic cancer, lung cancer, endometrial cancer, bone cancer, testicular cancer, skin cancer, kidney cancer, stomach cancer, esophageal cancer, head and neck cancer, salivary gland cancer, and myeloma.

In some aspects, the tumor is selected from the group consisting of acute myelogenous leukemia, adult T-cell leukemia, astrocytomas, cholangiocarcinoma, chronic myeloid leukemia, gastric cancer (e.g., gastric cancer with MET amplification), glioblastomata, head and neck cancer (e.g., head and neck squamous cell carcinoma [HNSCC]), Kaposi's sarcoma, leiomyosarcomas, lung cancer (e.g., non-small cell lung cancer [NSCLC]), lymphomas, malignant gliomas, malignant mesothelioma, melanoma, mesothelioma, MFH/fibrosarcoma, multiple myeloma, nasopharyngeal cancer, osteosarcoma, pancreatic carcinoma, prostate cancer, renal cell carcinoma, rhabdomyosarcoma, small cell lung cancer, synovial sarcoma, thyroid cancer, and Wilms' tumor.

According to one aspect, the present disclosure provides methods of treating a tumor in a subject. The methods, according to this aspect, comprise determining that the tumor is MET-positive; and administering one or more doses of an inhibitor of the HGF/MET signaling pathway. In some aspects, the inhibitor is an anti-MET antibody, a MET×MET bispecific antibody, or a drug conjugate thereof. In certain embodiments, the tumor is determined to be MET-positive by administering a radiolabeled antibody conjugate of the present disclosure to the subject; and visualizing the radiolabeled antibody conjugate in the tumor by PET imaging. Presence of the radiolabeled antibody conjugate in the tumor indicates that the tumor is MET-positive. In some embodiments, the cancer is lung cancer. In some embodiments, the cancer is non-small cell lung cancer. In some embodiments, the cancer is gastric cancer.

As used herein, the terms "treat", "treating", or the like, mean to alleviate symptoms, eliminate the causation of symptoms either on a temporary or permanent basis, to delay or inhibit tumor growth, to reduce tumor cell load or tumor burden, to promote tumor regression, to cause tumor shrinkage, necrosis and/or disappearance, to prevent tumor recurrence, to prevent or inhibit metastasis, to inhibit metastatic tumor growth, and/or to increase duration of survival of the subject.

According to one aspect, the present disclosure provides methods for monitoring the efficacy of an anti-tumor therapy in a subject undergoing treatment for cancer, wherein the methods comprise administering a radiolabeled antibody conjugate of the present disclosure to the subject; imaging the localization of the administered radiolabeled conjugate in the tumor by PET imaging; and determining tumor growth, wherein a decrease from the baseline in radiolabeled signal indicates tumor regression and efficacy of the anti-tumor therapy. In certain embodiments, the anti-tumor therapy comprises an inhibitor of the HGF/MET signaling pathway (e.g., a MET×MET bispecific antibody).

As used herein, the term "baseline," with respect to the MET expression in the tumor, means the numerical value of uptake of the radiolabeled conjugate for a subject prior to or at the time of administration of a dose of anti-tumor therapy. The uptake of the radiolabeled conjugate is determined using methods known in the art (see, for example, Oosting et al 2015, J. Nucl. Med. 56: 63-69). In certain embodiments, the anti-tumor therapy comprises an inhibitor of the HGF/MET signaling pathway.

To determine whether there is tumor regression, the uptake of the radiolabeled conjugate is quantified at baseline and at one or more time points after administration of the inhibitor of the HGF/MET signaling pathway (e.g., a MET×MET bispecific antibody). For example, the uptake of the administered radiolabeled antibody conjugate (e.g., radiolabeled MET×MET bispecific antibody conjugate) may be measured at day 2, day 3, day 4, day 5, day 6, day 7, day 8, day 9, day 10, day 11, day 12, day 14, day 15, day 22, day 25, day 29, day 36, day 43, day 50, day 57, day 64, day 71, day 85; or at the end of week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, week 24, or longer, after the initial treatment with the inhibitor of the HGF/MET signaling pathway (e.g., a MET×MET bispecific antibody). The difference between the value of the uptake at a particular time point following initiation of treatment and the value of the uptake at baseline is used to establish whether there has been a difference in amount of tumor tissue (tumor regression or progression). For example, a decrease from baseline in the uptake upon treatment with at least one dose of the inhibitor of the HGF/MET signaling pathway means tumor regression and indicates efficacy of the anti-tumor therapy.

In certain embodiments, the radiolabeled antibody conjugate is administered intravenously or subcutaneously to the subject. In certain embodiments, the radiolabeled antibody conjugate is administered intra-tumorally. Upon administration, the radiolabeled antibody conjugate is localized in the tumor. The localized radiolabeled antibody conjugate is imaged by PET imaging and the uptake of the radiolabeled antibody conjugate by the tumor is measured by methods known in the art. In certain embodiments, the imaging is carried out 1, 2, 3, 4, 5, 6 or 7 days after administration of the radiolabeled conjugate. In certain embodiments, the imaging is carried out on the same day upon administration of the radiolabeled antibody conjugate.

In certain embodiments, the radiolabeled anti-MET conjugate can be administered at a dose of about 0.1 mg/kg of body weight to about 100 mg/kg of body weight of the subject, for example, about 0.1 mg/kg to about 50 mg/kg, or about 0.5 mg/kg to about 25 mg/kg, or about 0.1 mg/kg to about 1.0 mg/kg of body weight.

IV. EXAMPLES

Certain embodiments of the disclosure are illustrated by the following non-limiting examples.

Example 1: Generation of Human Antibodies to MET

Human anti-MET antibodies, including those listed in Table 1, were prepared and characterized as described in US-2018-0134794, which is incorporated herein by reference in its entirety. In brief, human antibodies to MET were generated using an immunogen comprising recombinant human MET extracellular domain fused to human Fc (R&D Systems, Catalog #358-MT, Minneapolis, MN). The mice used for the immunizations express a "universal light chain." That is, the antibodies produced in this mouse have different heavy chain variable regions but essentially identical light chain variable domains.

The antibody immune response was monitored by a MET-specific immunoassay. When a desired immune response was achieved splenocytes were harvested and fused with mouse myeloma cells to preserve their viability and form hybridoma cell lines. The hybridoma cell lines were screened and selected to identify cell lines that produce MET-specific antibodies. Using this technique, and the immunogen described above, several anti-MET chimeric antibodies (i.e., antibodies possessing human variable domains and mouse constant domains) were obtained. In addition, several fully human anti-MET antibodies were isolated directly from antigen-positive B cells without fusion to myeloma cells, as described in U.S. 2007/0280945. Exemplary antibodies generated in this manner were designated as H4H13290P2, H4H13291P2, H4H13295P2, H4H13299P2, H4H13300P2, H4H13301P2, H4H13302P2, H4H13306P2, H4H13309P2, H4H13311P2, H4H13312P2, H4H13313P2, H4H13316P2, H4H13318P2, H4H13319P2, H4H13325P2, and H4H13331P2; sequences for these antibodies are shown in Table 1, above.

MET×MET bispecific antibodies were constructed from the anti-MET antibodies of Table 1. All anti-MET antibodies described herein comprise the same ("common") light chain (comprising the light chain variable region [LCVR] amino acid sequence of SEQ ID NO: 138, and light chain CDR [LCDR1, LCDR2 and LCDR3] amino acid sequences of SEQ ID NOs: 140, 142 and 144). In addition, all of the bispecific antibodies illustrated in this Example contain a "D2" arm derived from the exemplary anti-MET antibody H4H13312P2. Thus, both antigen-binding domains (D1 and D2) of all of the bispecific antibodies described in this example comprise this common light chain variable region, and all D2 binding arms comprise the heavy chain variable region from H4H13312P2; however, the bispecific antibodies differ from one another in terms of their D1 heavy chain variable regions (HCVRs) and heavy chain CDRs (HCDRs). Exemplary antibodies generated in this manner were designated as H4H14634D, H4H14635D, H4H14636D, H4H14637D, H4H14638D, H4H14639D, H4H14640D, H4H14641D, H4H16445D, H4H16446D, H4H16447D, H4H16448D, and H4H16449D; sequences for these antibodies are shown in Table 2, above. For example, the MET×MET bispecific antibody H4H14639D comprises D1-HCVR (SEQ ID NO: 58) from the anti-MET antibody of H4H13306 and D2-HCVR (SEQ ID NO: 82) from the anti-MET antibody of H4H13312P2.

Example 2: Conjugation of a MET×MET Bispecific Antibody H4H14639D with p-SCN-Bn-DFO To modify the parental MET×MET bispecific antibody, H4H14639D, and an isotype control antibody to be suitable for ImmunoPET studies with radiolabeling, a chelator, p-SCN-bn-Deferoxamine (DFO, aka desferrioxamine; Macrocylics, Cat #: B-705), was attached to the antibodies.

For the modification, 100 mg of 26.1 mg/mL H4H14639D was split into four aliquots and buffer exchanged into conjugation buffer (150 mM NaCl, 50 mM sodium carbonate, pH 9.0; Sigma-Aldrich, Cat. #: S6297-1 KG and Gibco, Cat. #: 24740-011, respectively) via four pre-equilibrated PD-10 desalting columns (GE Healthcare, Cat. #: 17-0851-01), as per the manufacturer's instructions. The elution products were combined, and the concentration was determined by UV absorption spectroscopy (Thermo Scientific NanoDrop 2000c, Cat. #: ND-2000c-US-CAN) measured at 280 nm and calculated from the primary-sequence-based extinction coefficient. This elution product was further diluted to 10.4 mg/mL with the conjugation buffer. In a separate vial, p-SCN-Bn-DFO was prepared in neat anhydrous dimethyl sulfoxide (DMSO; Sigma-Aldrich, Cat #: 276855-100ML) at a concentration of 13.8 mM. The p-SCN-Bn-DFO solution was added to the diluted elution product in ¼ increments, mixed by gentle pipetting, such that the final reaction solution makeup was 10 mg/mL bispecific antibody in conjugation buffer, 2% DMSO and 4-fold mole-to-mole excess of p-SCN-Bn-DFO to bispecific antibody. This solution was allowed to incubate in a 37° C. water bath with no additional agitation. After 30 minutes at 37° C., the reaction solution was split into four aliquots and promptly passed through four PD-10 desalting columns pre-equilibrated with a buffer containing 50 mM sodium acetate at pH 5.0 (formulation buffer; Sigma-Aldrich, Cat #32319-1KG-R). The final elution solutions were combined and sterile-filtered via a syringe filter (Acrodisc 13 mm syringe filter, Pall Corporation, Cat #: 4602) and referred to as the DFO-Ab immunoconjugate, DFO-H4H14639D immunoconjugate.

The concentration and DFO-to-Antibody Ratio (DAR, i.e. chelator-to-antibody ratio) was subsequently measured by UV absorption spectroscopy. For the absorbance measurement, the DFO-conjugated antibody was measured against the formulation buffer at 252 nm (A252), 280 nm (A280) and 600 nm (A600); see Tables 3 and 4. For the calculation, the background was corrected at each absorbance value using the equation:

$$A'_\lambda = A_\lambda - A_{600}$$

The antibody concentration, conjugate concentration, and DAR were calculated using the equations below: MW=144950 g $mol^{-1}$, $\varepsilon_{280}$=207729 $M^{-1}$ $cm^{-1}$, $\varepsilon_{252}$=79048 $M^{-1}$ $cm^{-1}$.

Antibody Concentration Calculation $$Conc\ mAb\ (\text{mg/mL}) = \frac{A'_{280}}{\epsilon_{280}} * MW$$

Conjugate Concentration Calculation $$Conc\ \text{conjugate (mg/mL)} = \frac{A'_{252} - 1.53A'_{280}}{\epsilon_{252} - 1.53\epsilon_{280}} * MW$$

DAR Calculation $$DAR = \frac{\epsilon_{252}A'_{280} - \epsilon_{280}A'_{252}}{18800A'_{252} - 28700A'_{280}}$$

The final DFO-Ab immunoconjugate yield was 61 mg.

Figure 2:
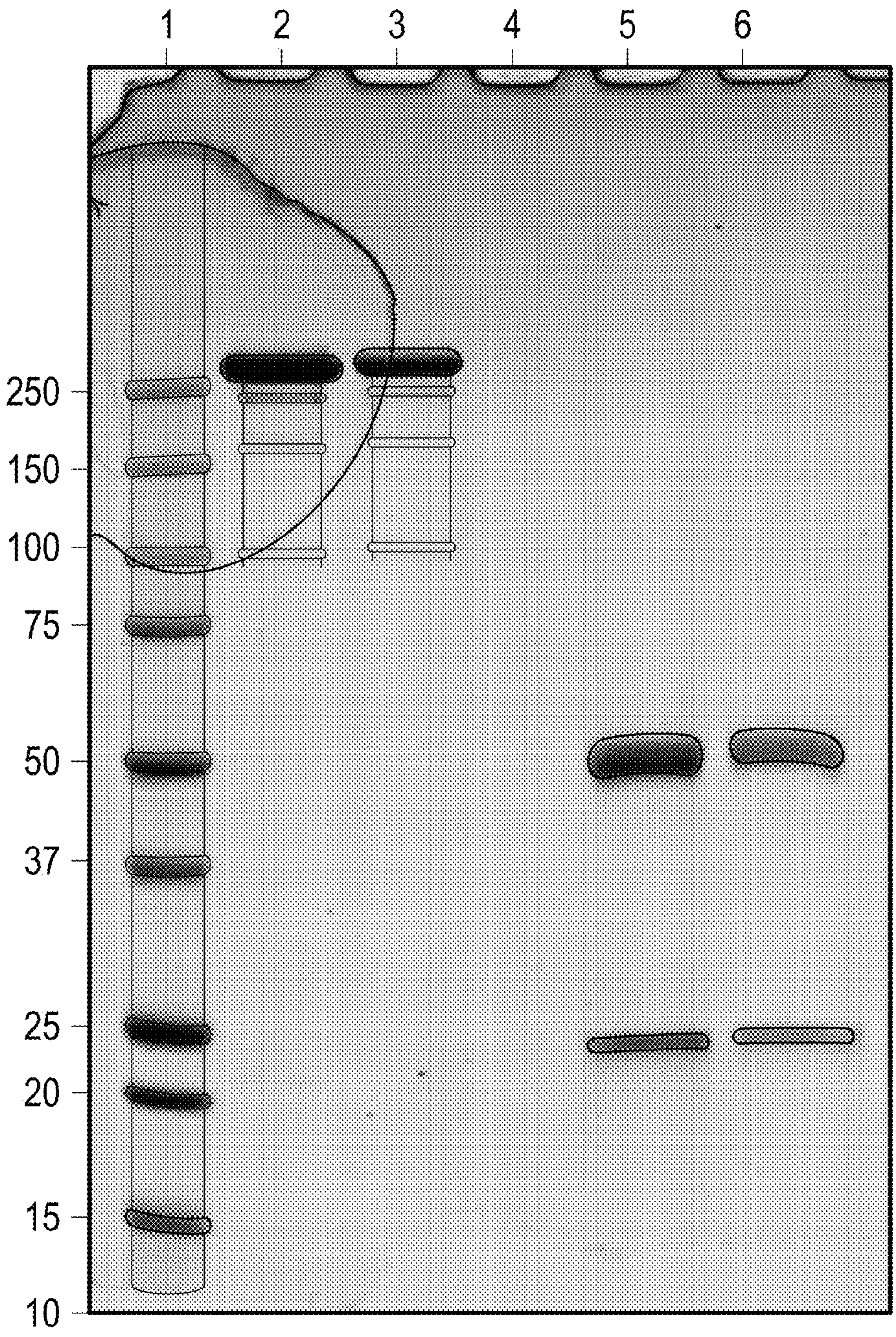
FIG. 2 depicts an image of SDS-PAGE of the DFO-MET×MET immunoconjugate. The gel demonstrates that the antibody integrity remains unchanged after DFO conjugation. Lanes are labeled as follows: 1) Standard ladder (BioRad, Cat. #: 161-0374), 2) bispecific antibody non-reduced, 3) DFO-Ab immunoconjugate non-reduced, 4) blank, 5) bispecific antibody reduced, 6) DFO-Ab immunoconjugate non-reduced. Each well was loaded with approximately 2 ug of protein. Note that non-reduced antibodies typically demonstrate less electrophoretic motility than expected as compared to the ladder for the standard SDS-PAGE setup.

The DFO-Ab immunoconjugate was assayed for monomeric purity with size-exclusion high performance liquid chromatography (SE-HPLC), using a Superdex 200 Increase 10/300 GL column (GE Healthcare, Cat. #: 28990944) with inline UV absorbance detector monitored at 280 nm and a PBS mobile phase at 0.75 mL/min (see FIG. 1). The main elution peak at approximately 15 minutes corresponds the monomeric species. The DFO-Ab immunoconjugate was also evaluated by sodium dodecyl sulfate polyacrylamide gel electrophoresis (SDS-PAGE; Invitrogen, Novex 4-20% Tris-Glycine Mini Gels, Cat. #: XP04200) against the unmodified bispecific antibody, H4H14639D, and executed as per manufacturer's instructions (see FIG. 2). Target binding equilibrium constant, i.e. $K_D$, of DFO-Ab immunoconjugate was assayed by SPR (GE Healthcare, Biacore 8k) and was determined to be within 10% of the bispecific antibody $K_D$.

TABLE 3

| DAR, Concentration, and Monomeric Purity of Conjugate | | | |
|---|---|---|---|
| Antibody | DAR | Concentration (mg/mL) | % Monomeric |
| H4H14639D | 1.26 | 6.76 | 99.6% |

TABLE 4

| Background-Subtracted UV Absorption Spectroscopy | | |
|---|---|---|
| Antibody | $A'_{280}$ | $A'_{252}$ |
| H4H14639D | 1.08 | 0.538 |

The bispecific antibody was successfully conjugated with p-SCN-Bn-DFO via primary amine chemistry as shown by UV absorption spectroscopy, SE-HPLC and SDS-PAGE. The calculated DAR of 1.26 was within the expected range of 1.0 to 2.0. SE-HPLC chromatogram demonstrated a highly monomeric product (99.6%) with no detectable lower molecular weight species. SDS-PAGE demonstrated bispecific antibody remains unchanged after DFO-conjugation.

Example 3: $^{89}Zr$ Chelation of DFO Conjugated Bispecific Antibodies

For use in ImmunoPET in vivo studies, the DFO-conjugated MET×MET bispecific antibody, H4H14639D, and a DFO-conjugated isotype control antibody were radiolabeled with $^{89}Zr$.

DFO-conjugated antibody (250 ug) was first brought to a total volume of 200 μL with 1 M HEPES, pH 7.4 (Teknova, Cat. #: H1030). Separately, approximately 5 mCi (<150 uL) $^{89}Zr$-oxalic acid solution (3D Imaging, Little Rock AR) was neutralized and buffered to pH 6.8 to 7.4 by bringing up to a total volume of 1000 uL of 1 M HEPES, pH 7.4. The DFO-Ab immunoconjugate and buffered $^{89}Zr$ solutions were combined, then gently mixed by pipet and incubated at room temperature for 45 minutes, quiescent. Upon completion, the reaction mixture was promptly buffer exchanged by a PD-10 column (GE Healthcare, Cat. #: 17-0851-01), preconditioned with 250 mM sodium acetate, pH 5.5 (Sigma-Aldrich, Cat. #: 32319-1 KG-R), as per manufacturer's instructions. The concentration of the elution product, now referred to as DFO-Ab radioimmunoconjugate, was determined by UV absorption spectroscopy (Thermo Scientific NanoDrop 2000c, Cat. #: ND-2000c-US-CAN) measured at 280 nm and calculated from the on DFO-contribution-adjusted, primary-sequence-based extinction coefficient using the equation:

$$\text{Concentration in mg/mL} = \text{Absorption at 280 nm in } AU \div 1.86\ \text{mL/mg 1/cm}$$

The DFO-Ab radioimmunoconjugate was sterile filtered and assayed for protein yield, specific activity (SA), radiochemical purity (RCP), protein purity and the target specific binding, i.e. immunoreactivity (IR). Data is reported in Table 5. The activity yield in mCi was measured using the dose calibrator (Capintec CRC-25R; Cat #: 5130-3215). The protein yield and specific activity of DFO-Ab radioimmunoconjugate was determined using the following equations:

a.

$$\text{protein yield in mg} = \text{concentration in mg/mL} \times \text{mass of solution in grams}$$

b.

$$SA\ \text{in mCi/mg} = \text{activity yield in mCi} \div \text{mass of conjugate in mg}$$

The RCP, unincorporated $^{89}Zr$, and protein purity were assayed by size-exclusion high performance liquid chromatography (SE-HPLC) using a Superdex 200 Increase 10/300 GL column (GE Healthcare, Cat. No. 28990944) with inline UV 280 absorption and gamma emission detector connected in series (Agilent Technologies, Model 1260 configured with Lablogic SCAN-RAM radiodetector) using PBS mobile phase at a flow rate of 0.75 mL/min. The percent protein purity was determined by comparing the relative integration of the high molecular weight (HMW) species peak (~10 to ~15 minutes) to the main peak (~15 to ~18 minutes) in the UV 280 chromatogram. Low molecular weight species (~18 to ~25 minutes) were not observed. The radio-chromatogram (gamma emission) was used to determine the radiochemical purity by relative comparison of the integration of the main to the unincorporated $^{89}Zr$ peak (~25 min) and % HMW species.

IR of the DFO-Ab radioimmunoconjugate was measured by a cell binding assay requiring two 500 uL aliquots, A and B, of EBC-1 cells (JCRB No. JCRB0820) at A at $2.0\times10^7$ cells/mL and B at $0.5\times10^7$ cells/mL. The DFO-Ab radioimmunoconjugate (20 ng) was added to aliquot A and allowed to incubate at 37° C., 5% $CO_2$ for 45 minutes. Both aliquots A and B were centrifuged (Eppendorf; Model #5504R) at 1500 rpm for 5 minutes. The supernatant from cell pellet B was discarded. The supernatant from cell pellet A was transferred to cell pellet B, followed by incubation and separation as above. Each cell pellet (A and B) was washed twice with 1 mL fresh cell culture media, centrifuging at 1500 rpm for 5 minutes between each wash. Supernatants from the washes were collected. The final activities for all components (each cell pellet resuspended in 500 uL of cell culture media, the supernatant and the four wash supernatants) were measured with a gamma counter (Perkin Elmer Wizard2; Model #2470-0020). IR was determined by sum of both pellets' activity divided by sum of the activity of all components, times 100%. This process was tested against a non-specific DFO-Ab radioimmunoconjugate (n=1) and the IR was determined to be 2.8%.

Figure 3:
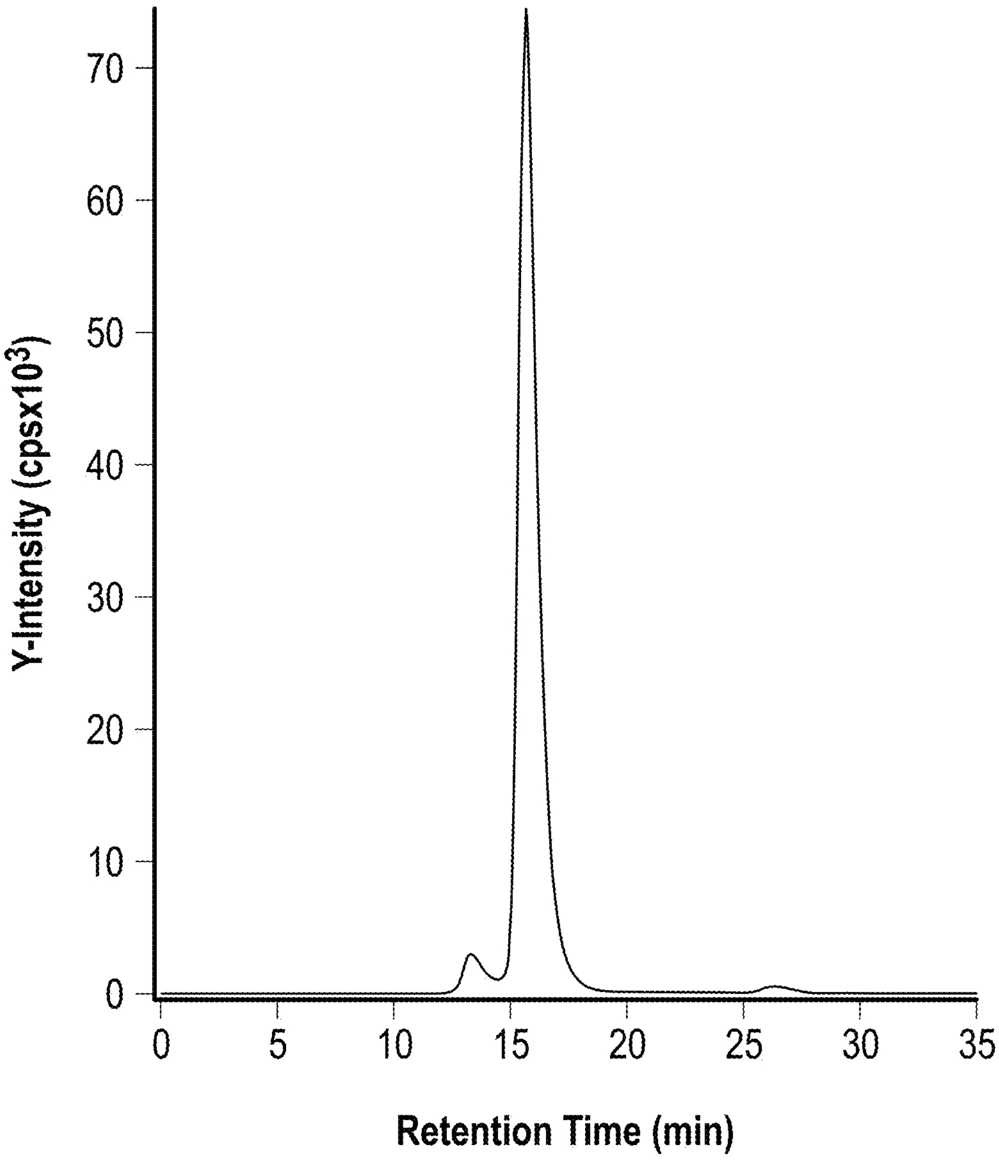
FIG. 3 depicts a representative SE-HPLC radiochromatogram of a 5 ug injection of a radioimmunoconjugate (DFO-MET×MET bispecific antibody) with gamma emission detection. The RCP of is greater than 95% while unincorporated $^{89}$Zr makes up less than 1% of total integrated activity.
Figure 4:
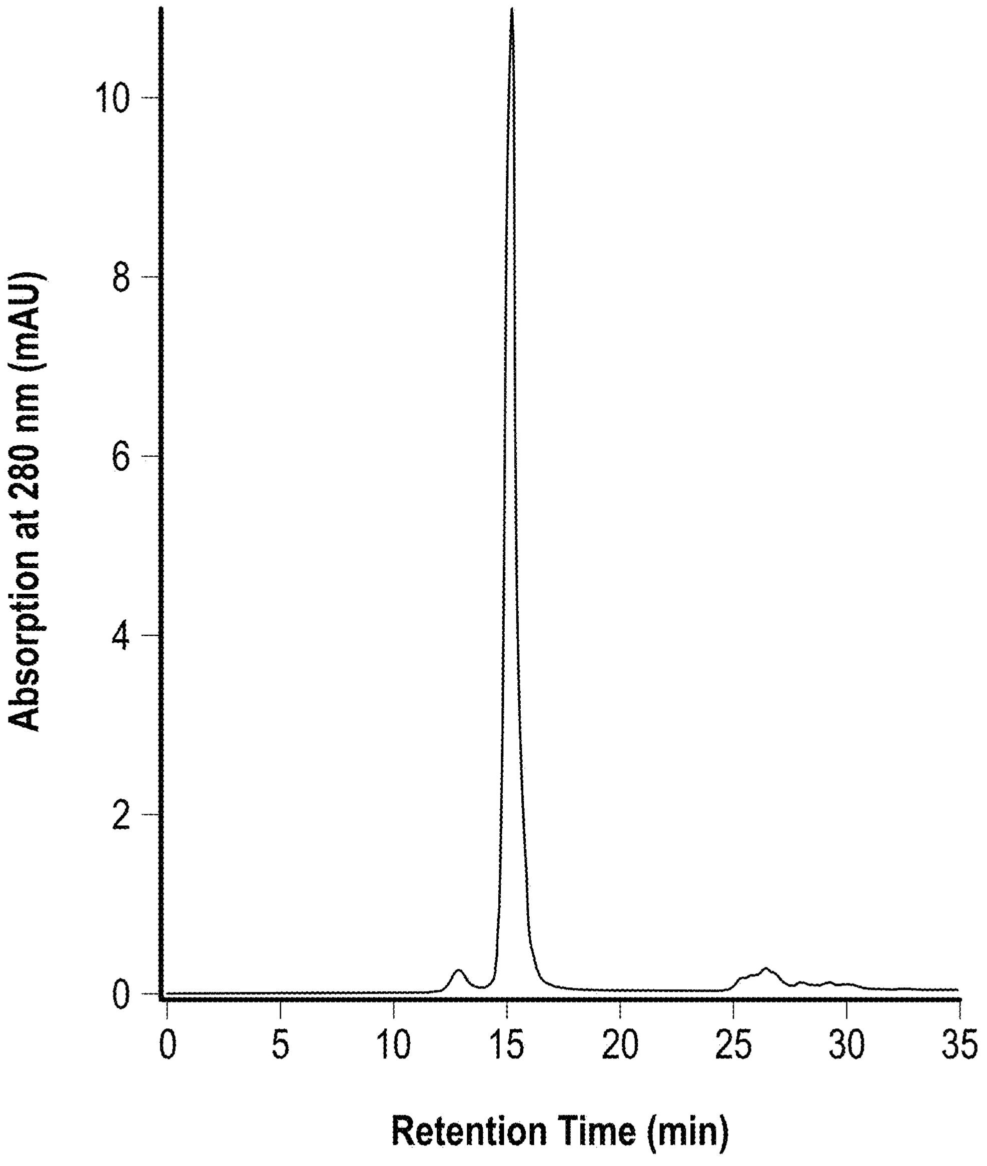
FIG. 4 depicts a representative SE-HPLC UV absorption chromatogram of a 5 ug injection of a radioimmunoconjugate (DFO-MET×MET bispecific antibody). Main (97.9%) and HMW (2.1%) species are indicated. The elution peaks between 25 and 31 minutes is a phenomenon of formulation buffer/mobile phase mixing and is deemed not proteinaceous in origin.

Assay results for the DFO-Ab radioimmunoconjugates generated above (n=5) are recorded in Table 5. Notably the average RCP was 94.6±1.2% with 2.7±1.9% unincorporated $^{89}Zr$ present and protein purity was 98.3±1.5%. Representative chromatograms are shown in FIGS. 3 and 4, respectively. The SA ranged from 11.9 to 21.3 mCi/mg and was appropriate for in vivo dosing. The average IR was 84±7% whereas a non-specific control was 2.8%.

TABLE 5

Summary of DFO-Ab radioimmunoconjugate for in vivo imaging and biodistribution studies

| Radio-labeling/ Study # | 1 | 2 | 3 | 4 | 5 | Average ± Stdev |
|---|---|---|---|---|---|---|
| Concentration (mg/mL) | 0.100 | 0.103 | 0.120 | 0.115 | 0.120 | 0.11 ± 0.01 |
| Protein yield (ug) | 171 | 168 | 203 | 196 | 209 | 189 ± 19 |
| SA (mCi/mg) | 16.0 | 11.9 | 21.3 | 12.8 | 17.2 | 15.8 ± 3.4 |
| RCP (%) | 94.6 | 92.3 | 94.8 | 95.7 | 95.4 | 94.6 ± 1.2 |
| Unincorporated $^{89}Zr$ | 5.4 | 4.6 | 1.1 | 1.4 | 0.8 | 2.7 ± 1.9 |
| Protein Purity (%) | ND | 98.2 | 95.9 | 99.5 | 99.5 | 98.3 ± 1.5 |
| Appearance | Clear | Clear | Clear | Clear | Clear | NA |
| IR (%) | 91 | ND | 85 | 78 | 86 | 84 ± 7 |

Stdev: standard deviation. NA: not applicable. ND: not determined. mAb: H4H14639D

Example 4: Binding Affinities and Kinetic Constants of MET×MET Bispecific and DFO-Conjugated MET×MET Bispecific Equilibrium dissociation constants ($K_D$ values) for hMET.mmh binding to purified anti-MET×MET bispecific mAb (H4H14639D) or anti-MET×MET bispecific mAb conjugated to DFO (H4H14639D-DFO) were determined using a real-time surface plasmon resonance biosensor using a Biacore T-200 instrument. The CM5 Biacore sensor surface was derivatized by amine coupling with a monoclonal mouse anti-human Fc antibody to capture purified H4H14639D or H4H14639D-DFO. This Biacore binding study was performed in a buffer composed of 0.01M HEPES pH 7.4, 0.15M NaCl, 0.05% v/v Surfactant P20 (HBS-P running buffer). Different concentrations of hMET with a C-terminal myc.myc hexahistidine tag prepared in HBS-ET running buffer were injected over the antibody captured surface at a flow rate of 50 μL/minute. Association of hMET.mmh to the captured monoclonal antibody was monitored for 5 minutes and the dissociation of hMET.mmh in HBS-ET running buffer was monitored for 10 minutes. All of the binding kinetics experiments were performed at 25° C. Kinetic association ($k_a$) and dissociation ($k_d$) rate constants were determined by fitting the real-time sensorgrams to a 1:1 binding model using Scrubber 2.0 c curve fitting software. Binding dissociation equilibrium constants ($K_D$) and dissociative half-lives (t½) were calculated from the kinetic rate constants as:

$$K_D(M) = k_d / k_a,$$

and $$t\frac{1}{2}\ (\text{min}) = 0.693 / k_d / 60$$

Binding kinetic parameters for human MET binding to purified antibodies at 25° C. are shown below in Table 6.

TABLE 6

Human MET Binding Kinetics to MET × MET Bispecific Antibody and DFO Conjugated MET × MET Bispecific Antibody at 25° C.

| Common Name | mab Captured (RU/nm) | Antigen Bound (RU/nm) | Antigen Conc (nM) | ka (1/Ms) | kd (1/s) | KD (M) | t½ (min) | Chi^2 | Theoretical Rmax (RU) | % Bound/ Theoretical Rmax |
|---|---|---|---|---|---|---|---|---|---|---|
| Non-binding isotype Control | 70.5 ± 13.1 | 0.25 | 90 | NB | NB | NB | NB | NB | NB | NB |
| H4H14639D (unconjugated) | 49.3 ± 1.0 | 26.35 | 90 | 3.25E+05 | 2.72E−03 | 8.36E−09 | 4.25 | 0.469 | 71.4 | 36.92 |
| H4H14639D-DFO DAR 0.59 | 49.1 ± 10.8 | 26.68 | 90 | 3.02E+05 | 2.39E−03 | 7.90E−09 | 4.84 | 0.422 | 71.1 | 37.54 |
| Non-binding isotype Control | 120.1 ± 3.3 | −1.46 | 90 | NB | NB | NB | NB | NB | NB | NB |
| H4H14639D-DFO DAR 1.02 | 82.3 ± 2.4 | 46.99 | 90 | 2.84E+05 | 1.83E−03 | 6.47E−09 | 6.30 | 0.656 | 119.1 | 39.44 |

TABLE 6-continued

Human MET Binding Kinetics to MET × MET Bispecific Antibody and DFO Conjugated MET × MET Bispecific Antibody at 25° C.

| Common Name | mab Captured (RU/nm) | Antigen Bound (RU/nm) | Antigen Conc (nM) | ka (1/Ms) | kd (1/s) | KD (M) | t½ (min) | Chi^ 2 | Theoretical Rmax (RU) | % Bound/ Theoretical Rmax |
|---|---|---|---|---|---|---|---|---|---|---|
| H4H14639D-DFO DAR 2.14 | 83.3 ± 1.8 | 48.39 | 90 | 3.69E+05 | 1.62E−03 | 4.38E−09 | 7.14 | 0.661 | 120.6 | 40.13 |

Example 5: In Vivo Biodistribution of Radiolabeled MET×MET Bispecific Antibody

Tumor xenografts that differ based on MET expression levels, EBC1 (MET high), NCI-H441 (MET moderate) and NCI-H358 (MET low), were selected for imaging in immunocompromised mice. SCID mice were implanted with $5\times10^6$ tumor cells and allowed to grow for 10-14 days. Mice were then dosed with 0.1 mg/kg $^{89}$Zr-DFO-H4H14639D and increasing amounts of unlabeled unconjugated antibody to achieve final protein doses of 0.1, 0.5 and 5 mg/kg. Control animals were dosed with 0.1 mg/kg $^{89}$Zr-DFO-Isotype Control Antibody and unlabeled unconjugated antibody to a final protein dose of 0.5 mg/kg. PET Imaging was conducted at Days 0, 1, 4 and 6. Biodistribution was performed at Day 6.

A Sofie Biosciences G8 PET/CT was used to acquire PET/CT images (Sofie Biosciences and Perkin Elmer). The instrument was pre-calibrated for detection of $^{89}$Zr prior to image acquisition. The energy window ranged from 150 to 650 keV with a reconstructed resolution of 1.4 mm at the center of the field of view. Mice underwent induction anesthesia using isoflurane and were kept under continuous flow of isoflurane during imaging. Static 10-minute images were acquired using the G8 acquisition software and subsequently reconstructed using the pre-configured settings. Image data was corrected for decay and other parameters. CT images were acquired following PET acquisition and subsequently co-registered with the PET images. Images were prepared using VivoQuant post-processing software (inviCRO Imaging Services).

For biodistribution studies, mice were euthanized at the final time-point (6 days post-$^{89}$Zr-DFO-H4H14639D administration) and blood was collected via cardiac puncture. Tumors and normal tissues were then excised, placed in counting tubes, and weighed. Count data for $^{89}$Zr in CPM was then collected by measuring samples on an automatic gamma counter (Wizard 2470, Perkin Elmer). The percent-injected dose per gram (% ID/g) was calculated for each sample using standards prepared from the injected material.

Figure 5:
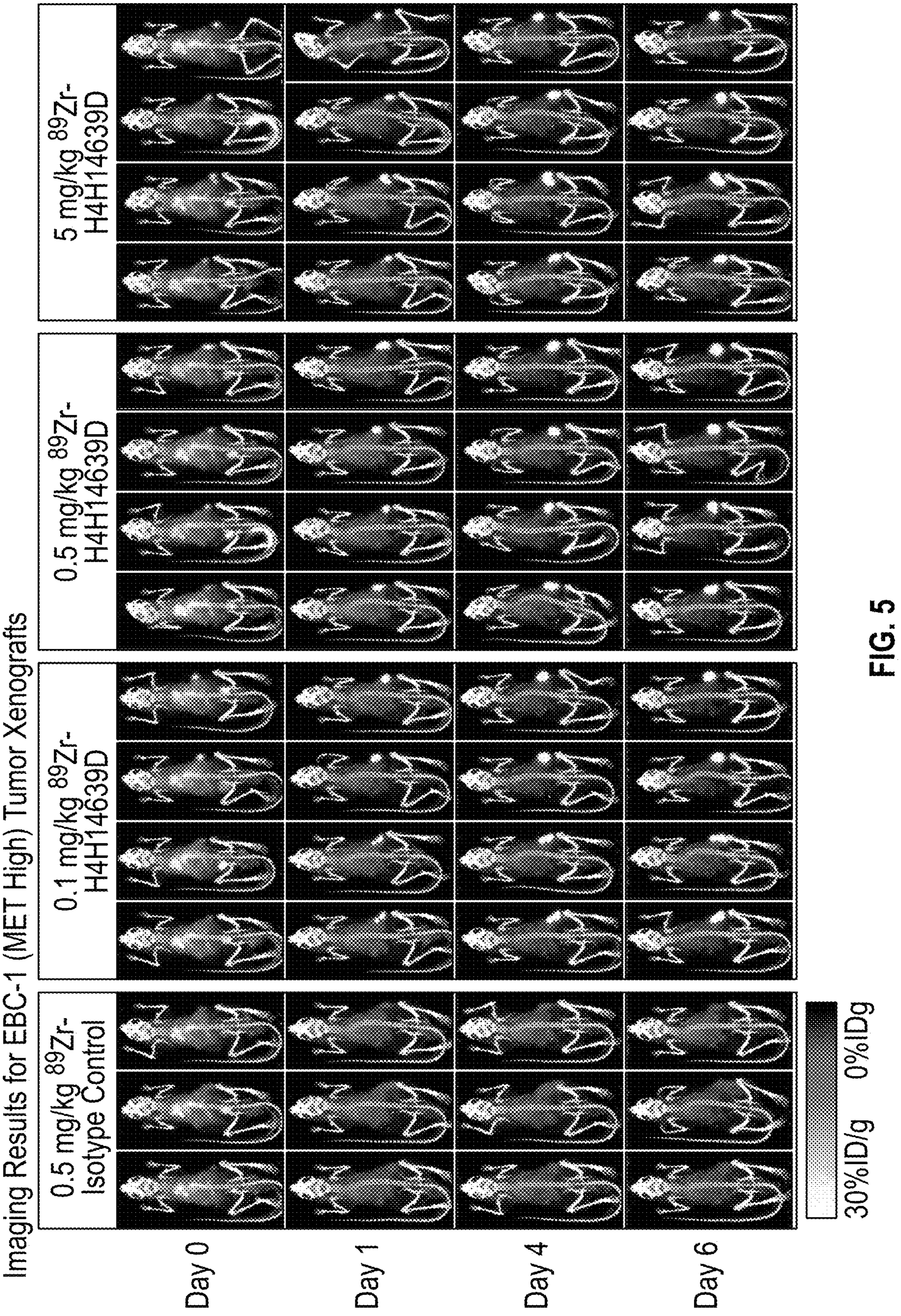
FIG. 5 depicts PET/CT images of EBC-1 tumor xenografts in mice. The mice were administered radiolabeled MET×MET bispecific antibody conjugate and over several days, the conjugate specifically localized to the MET expressing tumor xenografts.
Figure 6:
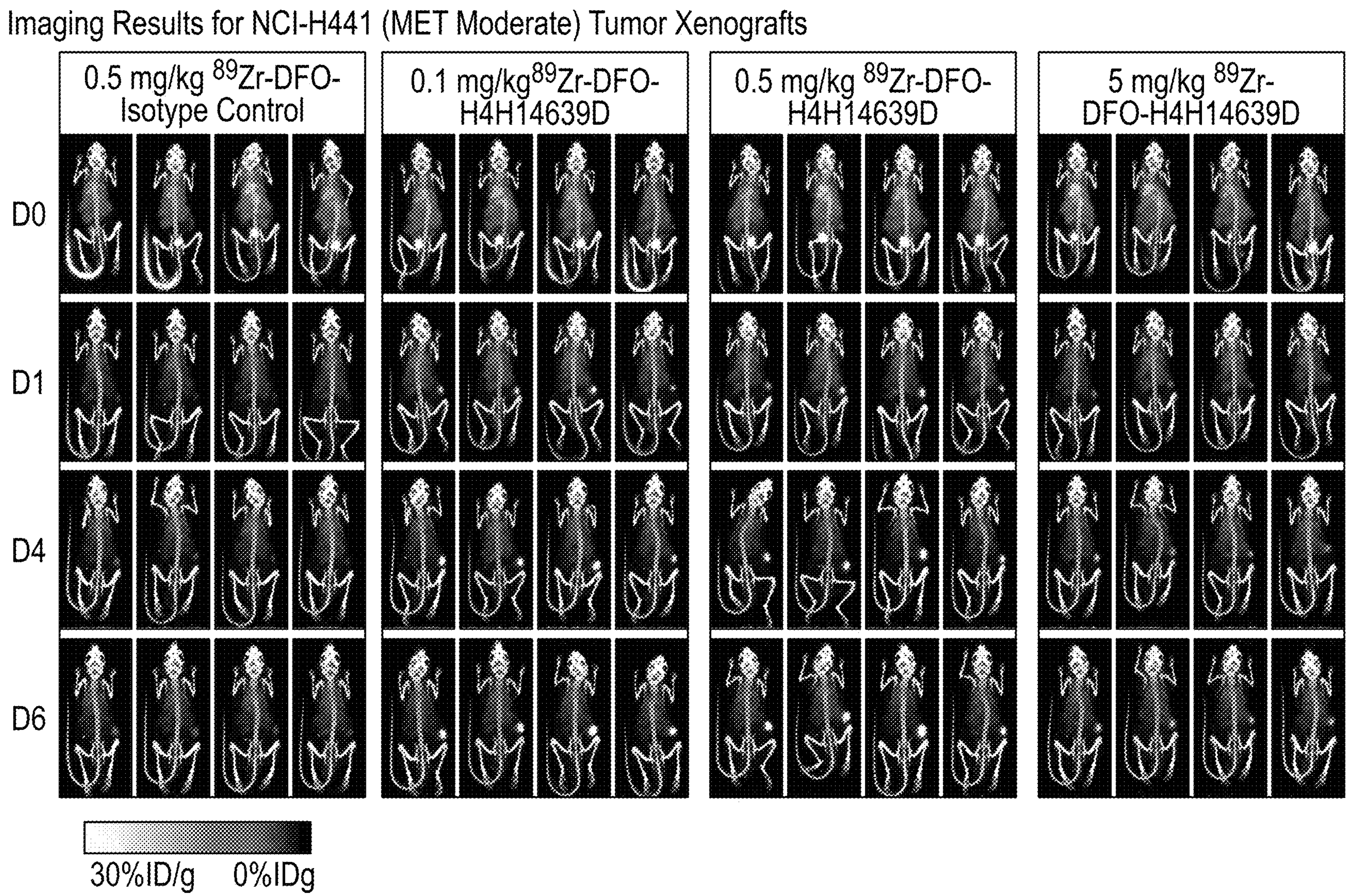
FIG. 6 depicts PET/CT images of NCI-H441 tumor xenografts in mice. The mice were administered radiolabeled MET×MET bispecific antibody conjugate and over several days, the conjugate specifically localized to the MET expressing tumor xenografts.
Figure 7:
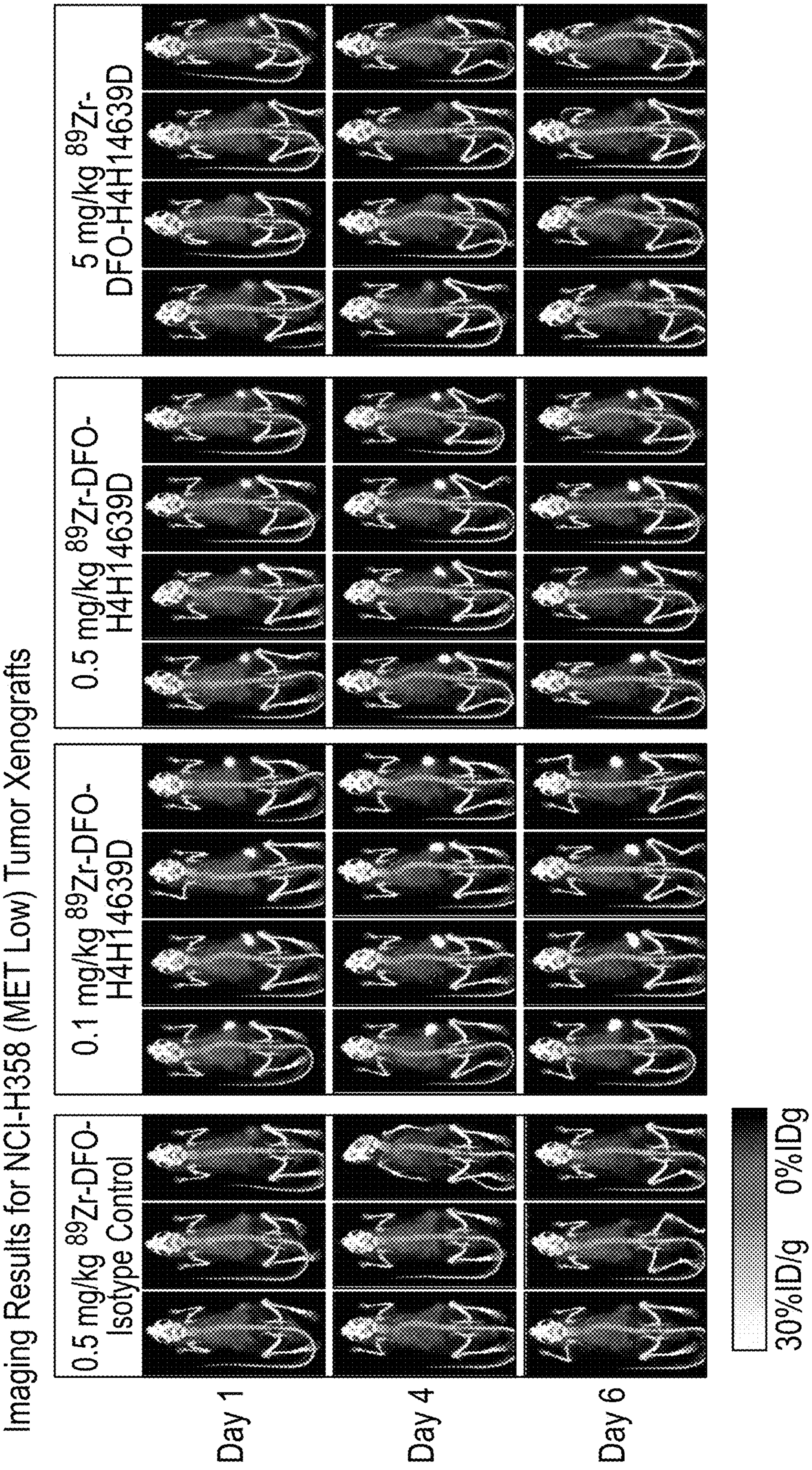
FIG. 7 depicts PET/CT images of NCI-H358 tumor xenografts in mice. The mice were administered radiolabeled MET×MET bispecific antibody conjugate and over several days, the conjugate specifically localized to the MET expressing tumor xenografts.
Figure 8A:
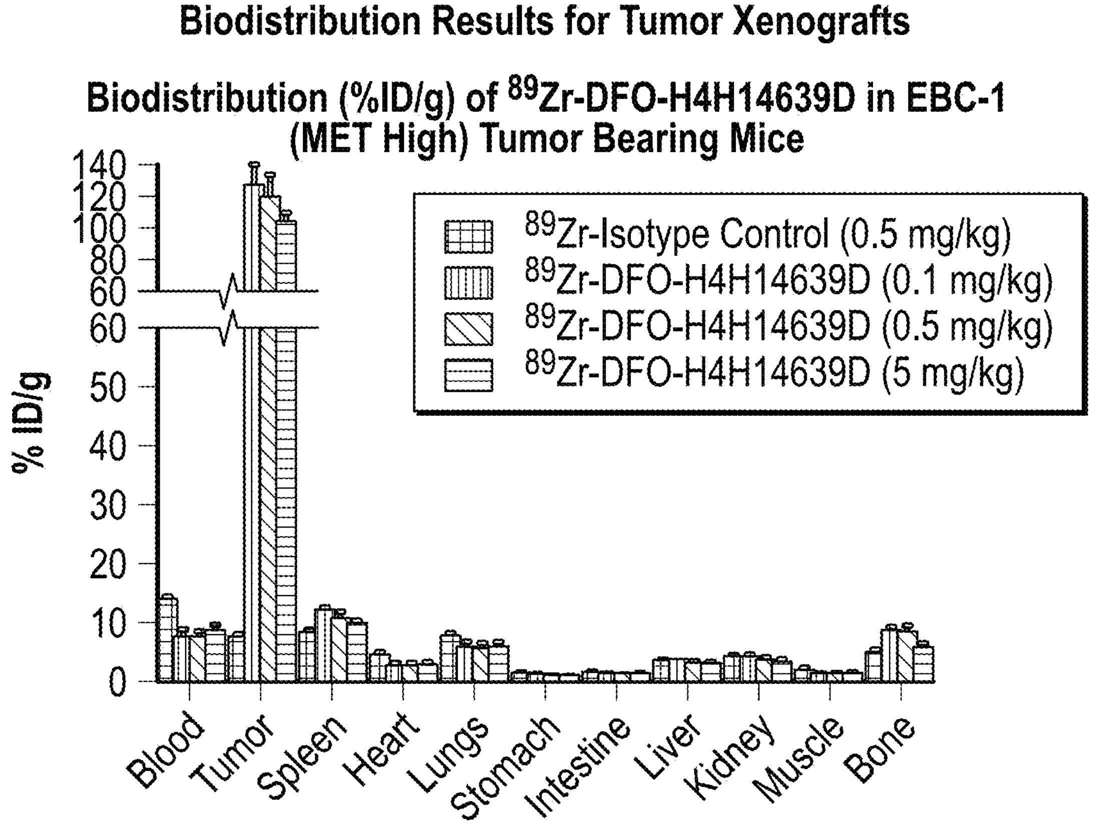
FIG. 8A, FIG. 8B, FIG. 8C, FIG. 8D, FIG. 8E, and FIG. 8F provide ex vivo biodistribution data for $^{89}$Zr-DFO-MET×MET bispecific antibody conjugate in SCID mice with tumor xenografts. Mice were administered a single IV dose 0.1 mg/kg, 0.5 mg/kg, or 5.0 mg/kg $^{89}$Zr-DFO-MET×MET bispecific antibody conjugate and were sacrificed 6 days later. Blood, collected via cardiac puncture, and the indicated harvested tissues were weighed and radioactivity was determined. The percent injected dose per gram (% ID/g) values for individual samples collected on day 6 were calculated relative to the radioactivity of a dose-standard from injected material ($^{89}$Zr-DFO-MET×MET bispecific antibody conjugate) and the weight of the individual samples. Data are plotted as mean±SD.
Figure 8B:
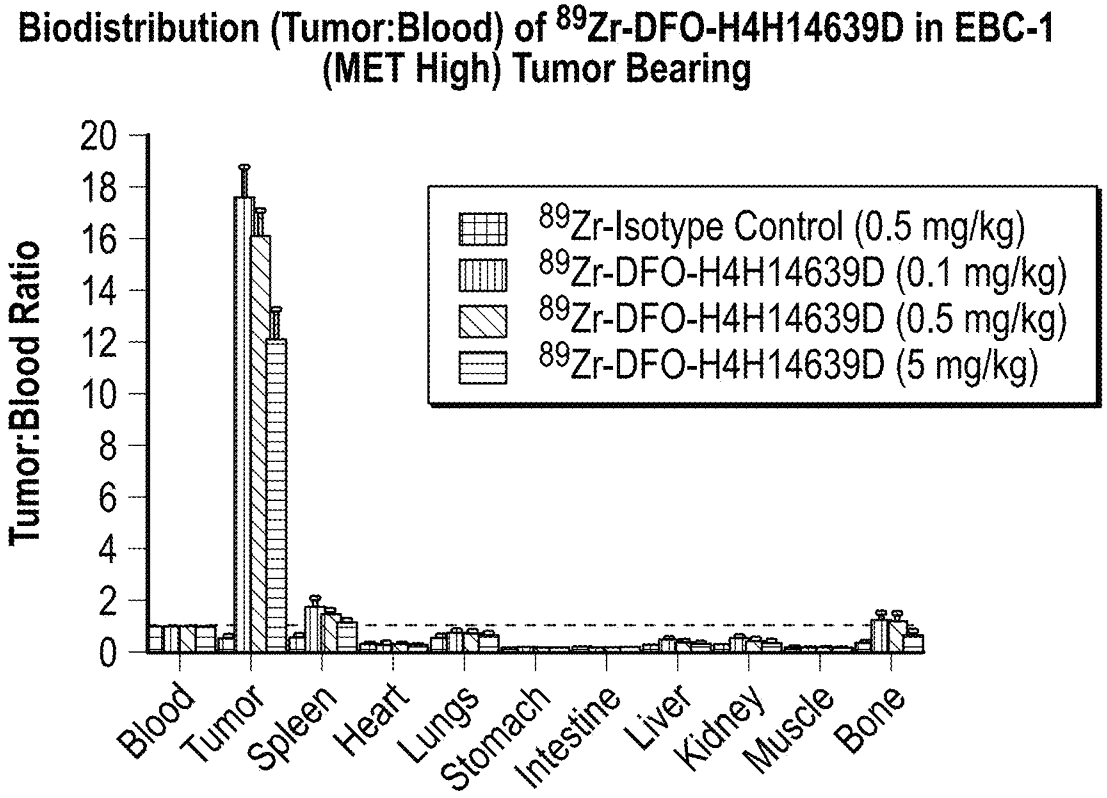
Figure 8C:
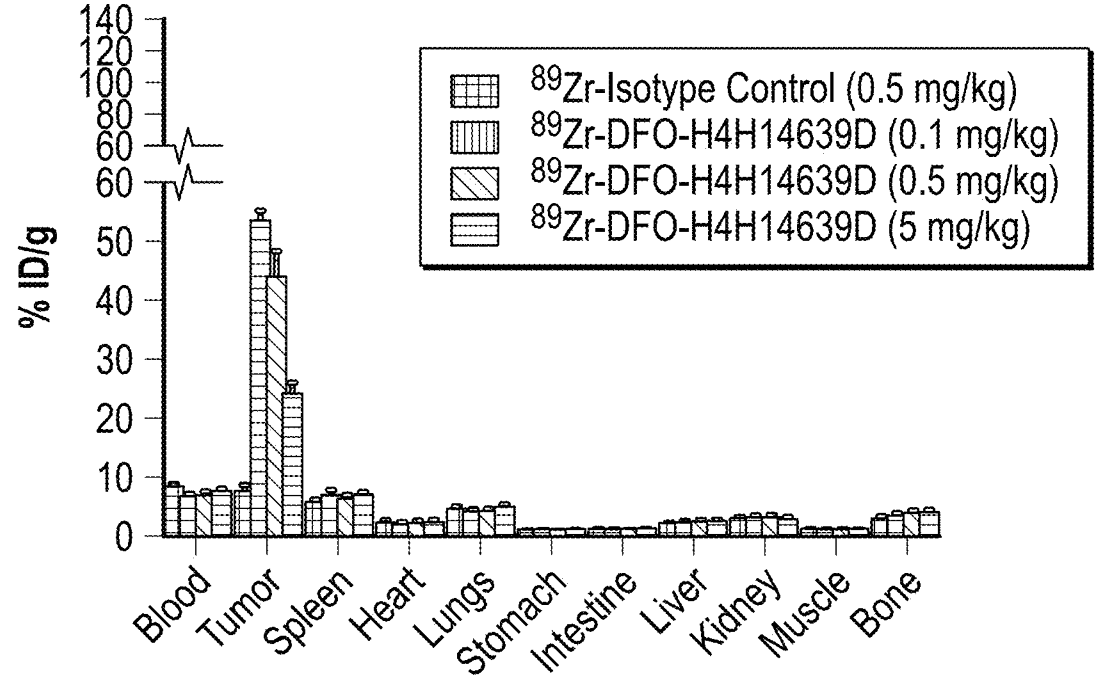
Figure 8D:
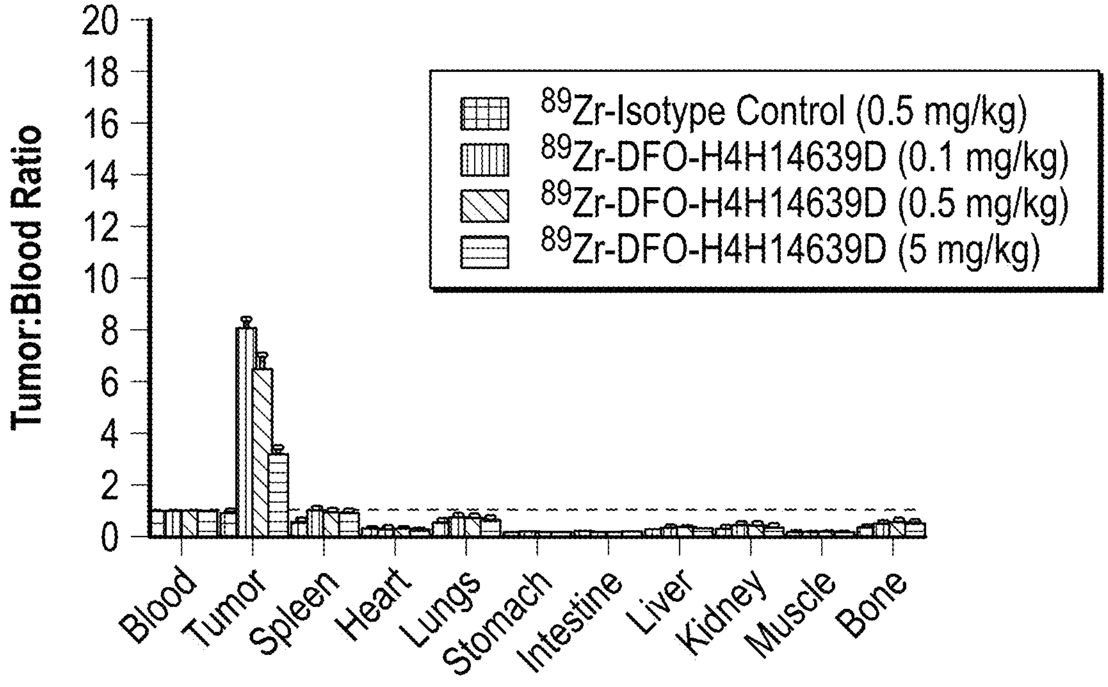
Figure 8E:
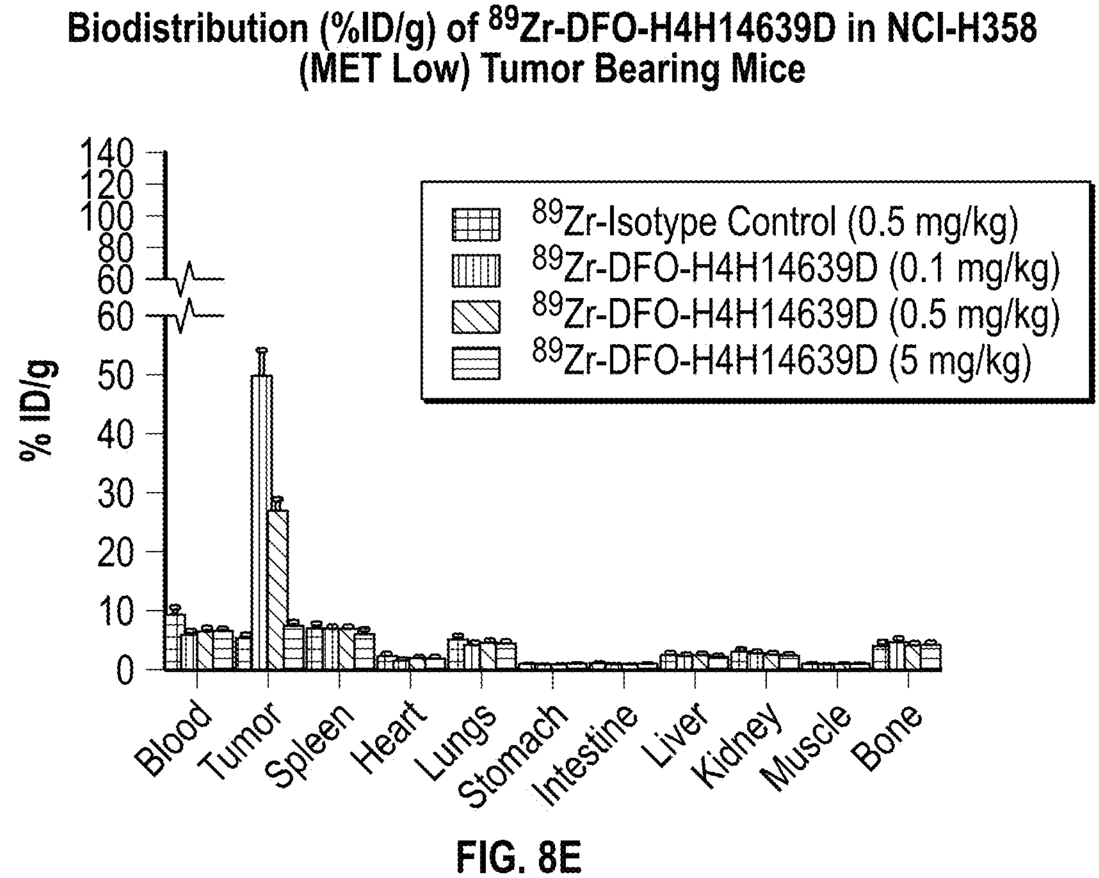
Figure 8F:
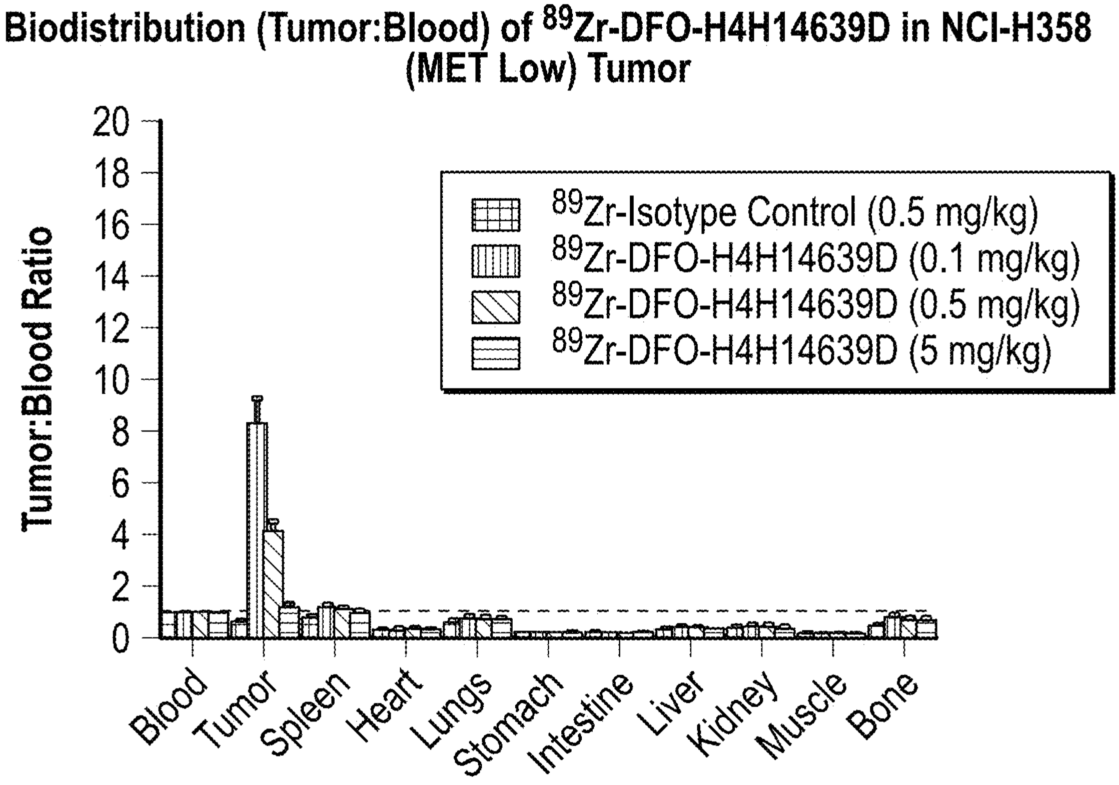
Figure 9:
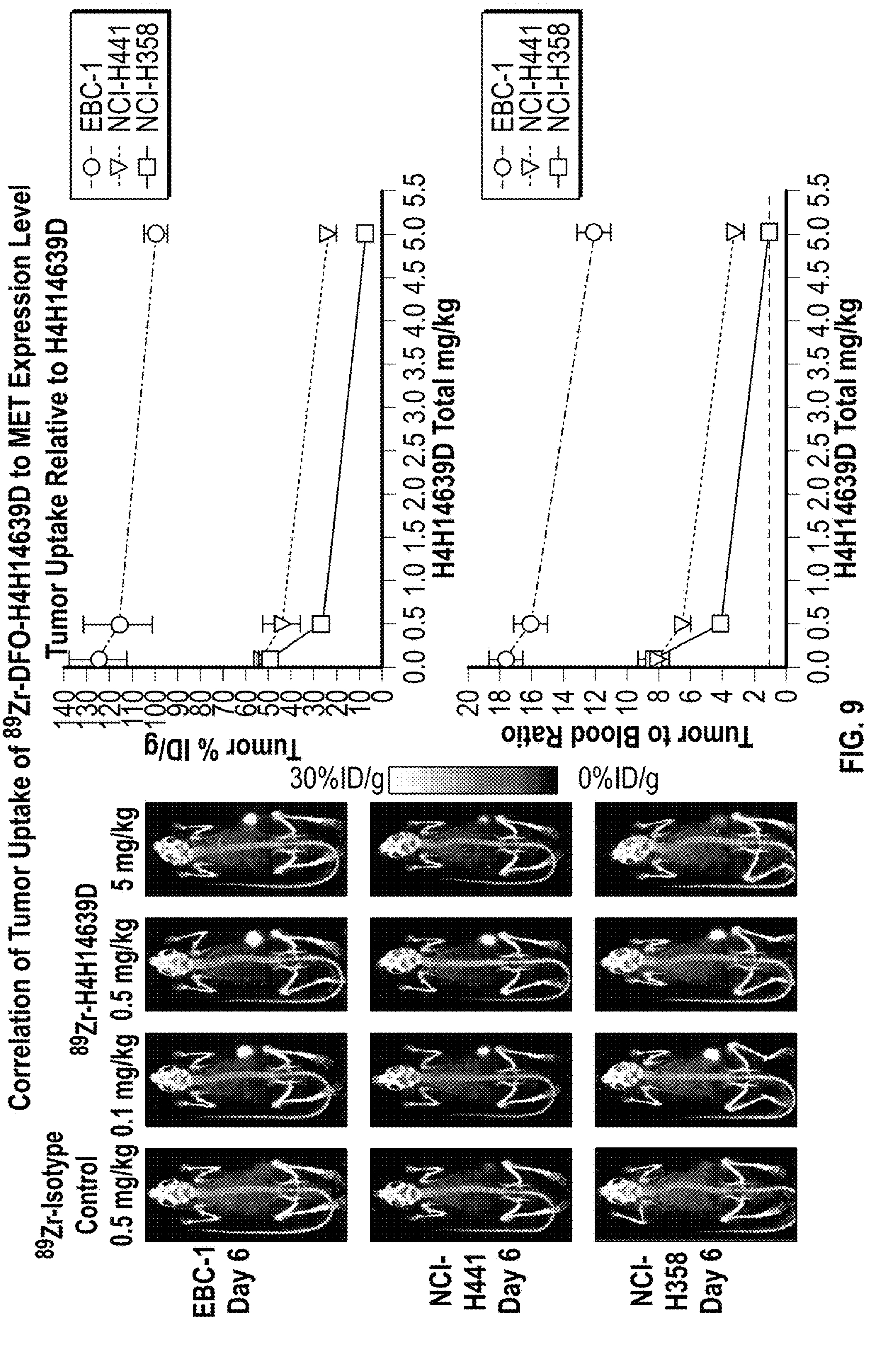
FIG. 9 shows the correlation between uptake of $^{89}$Zr-DFO-MET×MET bispecific antibody and MET expression level in the tumor xenografts from three MET expressing cell lines.

The imaging results demonstrate that $^{89}$Zr-DFO-H4H14639D specifically localizes to MET expressing tumor xenografts (FIGS. 5-7), which is further demonstrated by the biodistribution data. The blocking dose of 5 mg/kg $^{89}$Zr-DFO-H4H14639D showed increased blood uptake (% ID/g) and lower tumor uptake (% ID/g) in NCI-H441 (MET Moderate) and NCI-H358 (MET Low) tumors compared to the lower doses of 0.1 and 0.5 mg/kg $^{89}$Zr-DFO-H4H14639D (FIG. 8). Overall tumor uptake of $^{89}$Zr-DFO-H4H14639D in different tumor xenografts demonstrates a good correlation to relative MET expression (FIG. 9).

Example 6: MET×MET Bispecific Antibody Binding Capacity (ABC) by the Saturation Radioligand Binding Assay An Antibody Binding Capacity (ABC) assay was performed on the EBC-1, NCI-H441, NCI-H358 cell lines using $^{89}$Zr-DFO-anti-Met single-arm comparator antibody (Comp1; Onartuzumab, mentioned in U.S. 2016/0222115 and Martens et al., Clin Cancer Res 2006, 12(20): 6144-6152) and $^{89}$Zr-DFO-H4H14639D as the radioligands. Examples of radioligand preparation (the DFO antibody conjugation and subsequent $Zr^{89}$-radiolabeling) are described vide supra. All six experiments were performed in similar fashion with the aid of a Hamilton Starlet liquid handling system. In short, cells were first harvested, assayed for viability (>90% confirmed by trypan blue exclusion staining), and brought to 2 to $5\times10^6$ cells/mL in complete media. Next, 100 μL (0.2 to 0.5 million cells, $N_c$) was aliquoted along duplicate or quadruplicate rows of a V-bottom 96-well plate ("cell plate"). The cell plate was held at 4° C. until dosed with radiolabeled antibody in a later step. In a second V-bottom 96-well plate ("mAb plate"), 150 μL of radiolabeled antibody (0.10 to 0.12 mg/mL) was aliquoted across the rows of column 1 as well as a single well in column 12 as an internalization control. Columns 2-9 were then serial diluted by a factor 2.8 with cold media. Next, 50 μL of mAb plate was stamped into the cell plate. The cell plate was incubated with gentle agitation for 45 minutes at 4° C. After incubation, wells from columns 1 through 9 were first gently mixed by pipet to make a momentary cell suspension, then 30 μL (or 20% of total) was collected from each well into flip-cap tubes representing the total antibody dosed. The remaining cell plate was spun at 150 g for 5 minutes before removing the supernatants and discarding. The cell plate was then washed with 200 μL cold media, with five aspirate/dispense cycles before spinning the plate again, then removing the supernatants and discarding. This wash process was repeated two more times, before resuspending cells in 200 μL of cold buffer (10% FBS in PBS, v/v). Of the 200 μL, 180 μL from each well was collected and dispensed into flip-cap tubes, representing the cell-bound antibody. The activity of the total and bound antibody samples was measured using a gamma counter (Hidex Automatic Gamma Counter, Model #425-601). A calibration curve was generated from the total antibody dosed samples using counts detected vs total antibody dosed per well, T, based on the dilution series starting from the initial antibody concentration (divided by five because of sampling). The calibration curve was used to convert the bound fraction counts (multiplied by 1.38 because of sampling) to mass (or concentration) of bound antibody, B.

Internalization Control:

The radioligand internalization was also assayed at the highest dosed concentration at 4° C. for the 45 minutes. If significant, the fraction of internalized antibody was used to scale ABC accordingly. For the internalization control, the entire well contents (200 μL) of terminal column 12 was transferred to a 1.5 mL Eppendorf tube containing 1 mL low pH stripping buffer (50 mM glycine, 150 mM NaCl, pH 2.4) and left at room temperature for ten minutes. After the ten-minute incubation, the Eppendorf tube was spun at 150 g for 5 minutes. The supernatant was removed without disturbing the cell pellet and reserved for counting. The cell pellet was washed with 1 mL cold buffer (10% FBS in PBS, v/v) by aspirating 10 times, spinning, removing, and reserving the supernatant between washes. Activity of cell pellets, stripping supernatants, and wash supernatants were measured using a gamma counter. The fraction internalized, I, was calculated as the ratio of activity of the cell pellet over sum of the total activity of the cell pellet, stripping supernatant and wash supernatants.

ABC of Comp1:

Binding saturation data was fit using Equation 1 assuming the law of mass action under single-site conditions. The bound value was determined and converted to ABC via Equation 2. Under our binding/washing protocol, non-specific binding was determined to be a negligible component for all runs and was not considered as a part of the analysis. Internalization was determined to have a negligible contribution to the bound radioactivity and was also not considered as part of the analysis.

Equation 1 (for Comp1)

$$B = \frac{1}{2}\left(K_D + T_{Ag} + T - \sqrt{(K_D + T_{Ag} + T)^2 - 4T_{Ag}T}\right),$$

where, $K_D$ is the equilibrium disassociation constant in nM (fit parameter), $T_{Ag}$ is the total Ag present in nM (fit parameter), T is the total antibody dosed in nM (measured), B is the bound concentration in nM (measured).

$$ABC = \frac{N_A T_{Ag} V}{N_c 10^{15}}, \quad \text{Equation 2}$$

where $N_A$ is Avogadro's number, V is the well volume (150 μL), $N_c$ is the number cells per well (known).

ABC of H4H14639D:

Because there are multiple binding formats for H4H14639D, the data set was fit by the Hill-Langmuir equation (equation 3). The ABC was then calculated using equation 2. Non-specific binding was determined to be a negligible component for all runs was not considered as part of the analysis. The radioligand internalization was determined to have a non-negligible contribution to the bound radioactivity determination and therefore was compensated accordingly.

$$B = \frac{T_{Ag}(1 - I)}{1 + \left(\frac{K_I}{T}\right)^n} \quad \text{Equation 2 (for H4H14639D)}$$

where, B and $T_{Ag}$ as above, I is the fraction internalized (measured), $K_I$, n, and $T_{Ag}$ are fit parameters.

Figure 10A:
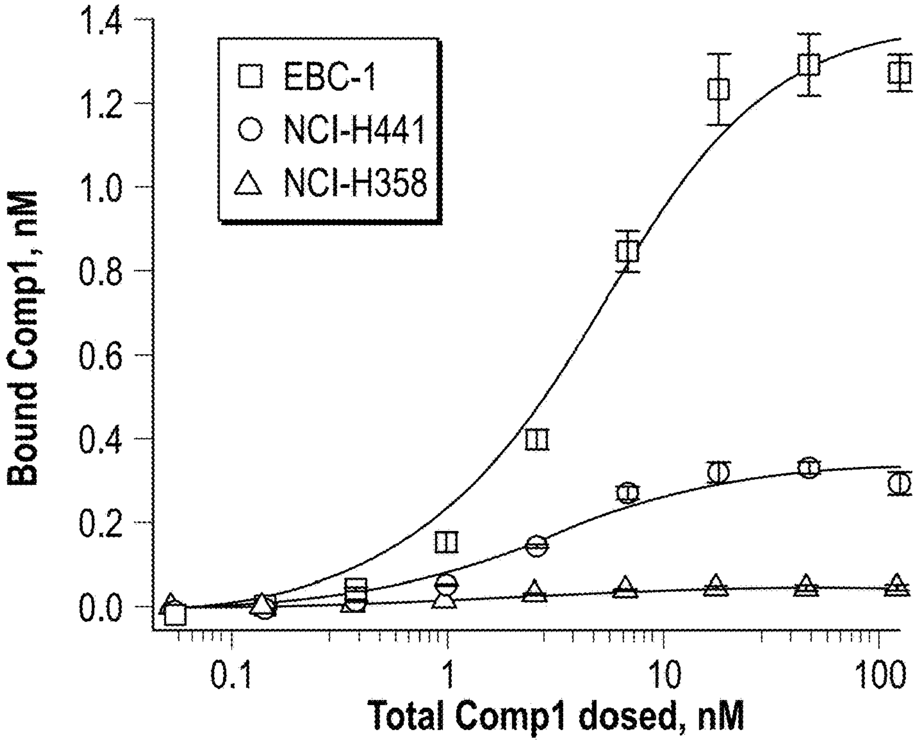
FIG. 10A and FIG. 10B show antibody saturation binding data for three MET expressing cell lines.
Figure 10B:
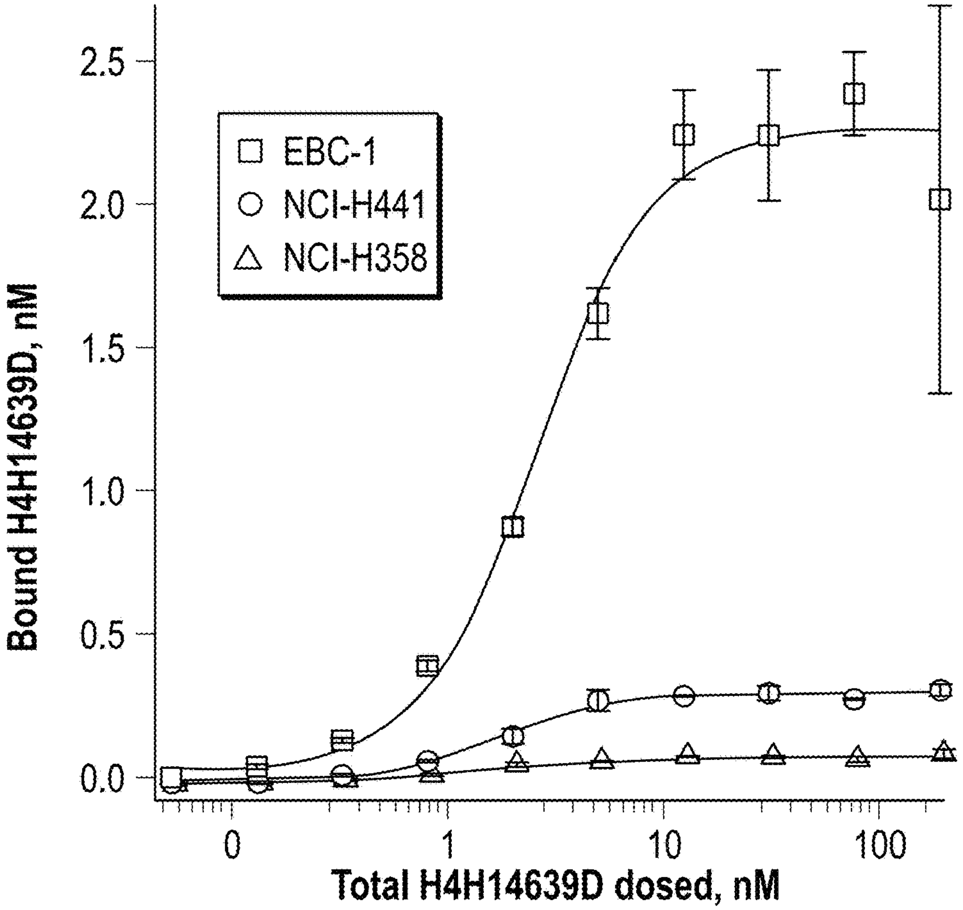

The ABC results are summarized in Tables 7 and 8 and shown in FIGS. 10A and 10B.

TABLE 7

ABC for Comp1 for three cell lines tested using equations 1 and 2. Fraction internalized at 4° C. was negligible.

| ABC/Cell line | EBC-1 | NCI-H441 | NCI-H358 |
|---|---|---|---|
| Average ± standard deviation × $10^3$, n | 250 ± 10, 4 | 62 ± 3, 4 | 21 ± 4, 2 |

TABLE 8

ABC for H4H14639D for three cell lines tested using equation 2 and 3.

| ABC/Cell line | EBC-1 | NCI-H441 | NCI-H358 |
|---|---|---|---|
| Average ± standard deviation × $10^3$, n | 310 ± 30, 4 | 46.25 ± 0.01, 2 | 37 ± 4, 2 |
| Fraction internalized under experimental conditions (4° C.) | 0.237 | 0.172 | 0.09 |

The ABC value using Comp1, an anti-Met, single-armed/mono-valent format antibody, is a reasonable estimate of the Met receptor copy number (i.e. 1-to-1 antibody to receptor). However, the ABC value using the antibody H4H14639D is not expected to represent the 1-to-1 Met receptor copy number a priori.

The embodiments and examples described above are intended to be merely illustrative and non-limiting. Those skilled in the art will recognize or will be able to ascertain using no more than routine experimentation, numerous equivalents of specific compounds, materials and procedures. All such equivalents are considered to be within the scope and are encompassed by the appended claims.

What is claimed is:

1. A method for making a radiolabeled anti-MET binding protein, the method comprising:

reacting an anti-MET binding protein with a chelating agent having a reactive moiety for conjugation to the anti-MET binding protein to generate a conjugate of anti-MET binding protein-chelating agent, and loading a radioactive positron emitter onto the conjugate, whereby the radioactive positron emitter and the chelating agent form a stable complex, thereby making the radiolabeled anti-MET binding protein;

wherein the anti-MET-binding protein comprises (i) three heavy chain complementarity determining regions (HCDRs) in a heavy chain variable region (HCVR) having an amino acid sequence selected from the group consisting of SEQ ID NO: 2, 10, 18, 26, 34, 42, 50, 58, 66, 74, 82, 90, 98, 106, 114, 122, and 130; and (ii) three light chain complementarity determining regions (LCDRs) in a light chain variable region (LCVR) having an amino acid sequence of SEQ ID NO: 138.

2. The method of claim 1, wherein the reactive moiety is selected from the group consisting of isothiocyantatobenzyl group, an n-hydroxysuccinimide ester, 2,3,5,6 tetraflurorphenol ester, and n-succinimidyl-S-acetylthioacetate.

3. The method of claim 1, wherein the chelating agent and the reactive moiety has the following formula:

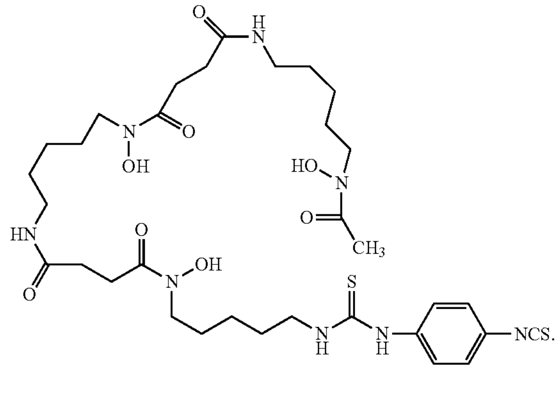

4. The method of claim 1, wherein the step of loading the radioactive positron emitter comprises incubating the anti-MET binding protein-chelating agent conjugate with the positron emitter to promote formation of a stable complex of the positron emitter and the anti-MET binding protein-chelating agent.

5. The method of claim 1, wherein the chelating agent is desferrioxamine.

6. The method of claim 1, wherein the chelating agent with a reactive moiety is p-isothiocyanatobenzyl-desferrioxamine.

7. The method of claim 1, wherein the positron emitter is $^{89}$Zr-oxalic acid or another salt thereof.

8. The method of claim 1, wherein the chelating agent-to-anti-MET-binding protein ratio is from about one to about four.

9. The method of claim 1, wherein the chelating agent-to-anti-MET-binding protein ratio is from about one to about two.

10. The method of claim 1, wherein the chelating agent-to-anti-MET-binding protein ratio is about 1.3.

11. The method of claim 1, wherein the conjugate of anti-MET binding protein-chelating agent has a formula:

(III)

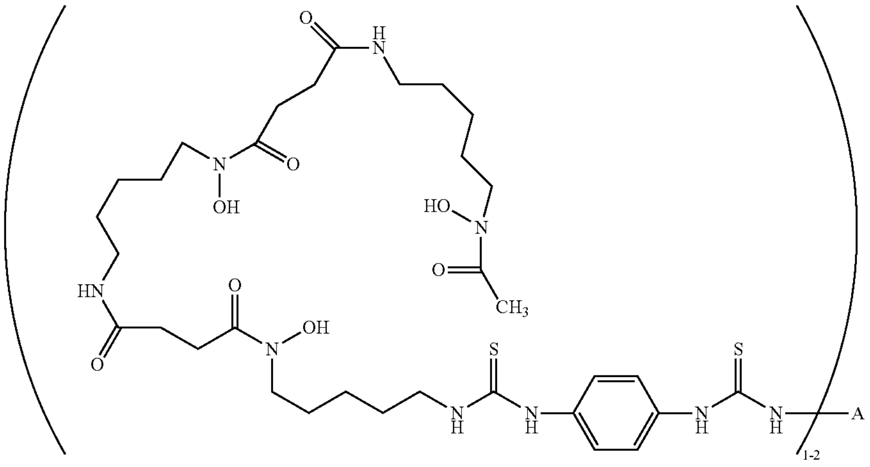

, or a salt thereof, wherein-A is the anti-MET binding protein.

12. The method of claim 1, comprising contacting the compound of Formula (III):

(III)

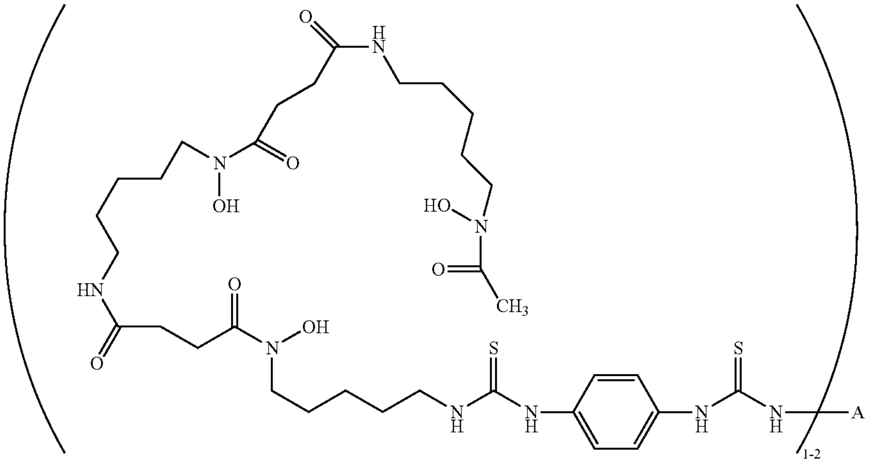

with $^{89}$Zr, wherein A is the anti-MET-binding protein.

13. The method of claim 1, wherein the radiolabeled anti-MET binding protein is

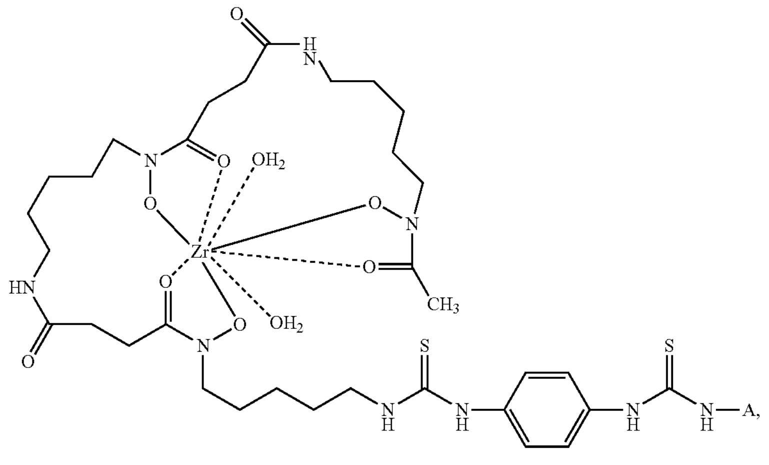

wherein A is the anti-MET-binding protein and Zr is the positron emitter $^{89}$Zr.

14. The method of claim 1, wherein the anti-MET-binding protein has one or more properties selected from the group consisting of:

(i) comprises an HCVR having an amino acid sequence selected from the group consisting of SEQ ID NOs: 2, 10, 18, 26, 34, 42, 50, 58, 66, 74, 82, 90, 98, 106, 114, 122, and 130;

(ii) comprises an LCVR having an amino acid sequence of SEQ ID NO: 138;

(iii) comprises an HCDR3 domain having an amino acid sequence selected from the group consisting of SEQ ID NOs: 8, 16, 24, 32, 40, 48, 56, 64, 72, 80, 88, 96, 104, 112, 120, 128 and 136; and an LCDR3 domain having an amino acid sequence of SEQ ID NO: 144;

(iv) comprises an HCDR1 domain having an amino acid sequence selected from the group consisting of SEQ ID NOs: 4, 12, 20, 28, 36, 44, 52, 60, 68, 76, 84, 92, 100, 108, 116, 124, and 132; an HCDR2 domain having an amino acid sequence selected from the group consisting of SEQ ID NOs: 6, 14, 22, 30, 38, 46, 54, 62, 70, 78, 86, 94, 102, 110, 118, 126, and 134; an LCDR1 domain having an amino acid sequence of SEQ ID NO: 140; and an LCDR2 domain having an amino acid sequence of SEQ ID NO: 142;

(v) is a multi-specific antigen-binding molecule comprising a first binding specificity to MET and a second binding specificity to a tumor specific antigen;

(vi) is a multi-specific antigen-binding molecule comprising a first binding specificity to one epitope of MET and a second binding specificity to a second epitope of MET;

(vii) binds to monomeric human MET with a KD of between 1 nM and 230 nM as measured by surface plasmon resonance at 25° C. or 37° C.;

(viii) binds to dimeric human MET with a KD of between 0.25 nM and 3 nM as measured by surface plasmon resonance at 25° C. or 37° C.;

(ix) blocks the binding of HGF to MET; and (x) suppresses tumor growth and increases survival in subjects with cancer.

15. The method of claim 1, wherein the anti-MET-binding protein is an anti-MET antibody or a MET×MET bispecific antibody.

16. The method of claim 1, wherein the anti-MET-binding protein thereof comprises three CDRs in an HCVR of SEQ ID NO: 18.

17. The method of claim 1, wherein the anti-MET-binding protein comprises three CDRs in an HCVR of SEQ ID NO: 58.

18. The method of claim 1, wherein the anti-MET-binding protein comprises three CDRs in an HCVR of SEQ ID NO: 82.

19. The method of claim 1, wherein the anti-MET-binding protein comprises three CDRs in an LCVR of SEQ ID NO: 138.

20. The method of claim 1, wherein the anti-MET-binding protein comprises an HCDR1 as set forth in SEQ ID NO: 20, an HCDR2 as set forth in SEQ ID NO: 22, and an HCDR3 as set forth in SEQ ID NO: 24.

21. The method of claim 1, wherein the anti-MET-binding protein comprises an HCDR1 as set forth in SEQ ID NO: 60, an HCDR2 as set forth in SEQ ID NO: 62, and an HCDR3 as set forth in SEQ ID NO: 64.

22. The method of claim 1, wherein the anti-MET-binding protein comprises an HCDR1 as set forth in SEQ ID NO: 84, an HCDR2 as set forth in SEQ ID NO: 86, and an HCDR3 as set forth in SEQ ID NO: 88.

23. The method of claim 1, wherein the anti-MET-binding protein comprises an LCDR1 as set forth in SEQ ID NO: 140, an LCDR2 as set forth in SEQ ID NO: 142, and an LCDR3 as set forth in SEQ ID NO: 144.

24. The method of claim 1, wherein the anti-MET-binding protein is a MET×MET bispecific antibody, and wherein the bispecific antibody comprises:

(i) a first antigen-binding domain (D1); and (ii) a second antigen-binding domain (D2);

wherein D1 specifically binds a first epitope of human MET; and wherein D2 specifically binds a second epitope of human MET.

25. The method of claim 24, wherein:

(i) D1 comprises three HCDRs within an HCVR amino acid sequence of SEQ ID NO: 58; and (ii) D2 comprises three HCDRs within an HCVR amino acid sequence of SEQ ID NO: 82.

26. The method of claim 24, wherein:

(i) D1 comprises a HCDR1-HCDR2-HCDR3-LCDR1-LCDR2-LCDR3 set of amino acid sequences of SEQ ID NOs: 60-62-64-140-142-144; and (ii) D2 comprises a HCDR1-HCDR2-HCDR3-LCDR1-LCDR2-LCDR3 set of amino acid sequences of SEQ ID NOs: 84-86-88-140-142-144.

27. The method of claim 24, wherein:

(i) D1 comprises three LCDRs within an LCVR amino acid sequence of SEQ ID NO: 138; and (ii) D2 comprises three LCDRs within an LCVR amino acid sequence of SEQ ID NO: 138.

28. A method for making a radiolabeled anti-MET binding protein, the method comprising:

loading a radioactive positron emitter onto a conjugate of an anti-MET binding protein-chelating agent, whereby the radioactive positron emitter and the chelating agent form a stable complex, thereby making the radiolabeled anti-MET binding protein;

wherein the anti-MET-binding protein comprises (i) three heavy chain complementarity determining regions (HCDRs) in a heavy chain variable region (HCVR) having an amino acid sequence selected from the group consisting of SEQ ID NO: 2, 10, 18, 26, 34, 42, 50, 58, 66, 74, 82, 90, 98, 106, 114, 122, and 130; and (ii) three light chain complementarity determining regions (LCDRs) in a light chain variable region (LCVR) having an amino acid sequence of SEQ ID NO: 138.

* * * * *